US010266498B2

United States Patent
Douce et al.

(10) Patent No.: US 10,266,498 B2
(45) Date of Patent: Apr. 23, 2019

(54) FAMILY OF DISCRIMINATING MOLECULES FOR NEUTRON AND GAMMA RAYS AND IONIC LIQUIDS

(71) Applicants: CENTRE NATIONAL DE LA RECHERCHE SCIENTIFIQUE (C.N.R.S), Paris (FR); Université de Strasbourg, Strasbourg (FR)

(72) Inventors: Laurent Douce, Strasbourg (FR); Louise Stuttge, Strasbourg (FR); Ezeddine Bouajila, Villeurbanne (FR); Julien Fouchet, Strasbourg (FR); Benoît Heinrich, Strasbourg (FR)

(73) Assignees: CENTRE NATIONAL DE LA RECHERCHE SCIENTIFIQUE (C.N.R.S.), Paris (FR); UNIVERSITE DE STRASBOURG, Strasbourg (FR)

( * ) Notice: Subject to any disclaimer, the term of this patent is extended or adjusted under 35 U.S.C. 154(b) by 450 days.

(21) Appl. No.: 14/777,660

(22) PCT Filed: Mar. 18, 2014

(86) PCT No.: PCT/EP2014/055428
§ 371 (c)(1),
(2) Date: Sep. 16, 2015

(87) PCT Pub. No.: WO2014/147078
PCT Pub. Date: Sep. 25, 2014

(65) Prior Publication Data
US 2016/0145214 A1 May 26, 2016

(30) Foreign Application Priority Data
Mar. 18, 2013 (FR) .................................. 13 52400

(51) Int. Cl.
| | | |
|---|---|---|
| G01T 7/00 | (2006.01) | |
| B01J 29/14 | (2006.01) | |
| C07D 233/58 | (2006.01) | |
| C07D 403/04 | (2006.01) | |
| C07C 311/48 | (2006.01) | |

(52) U.S. Cl.
CPC .......... C07D 233/58 (2013.01); B01J 29/146 (2013.01); C07C 311/48 (2013.01); C07D 403/04 (2013.01); G01T 7/00 (2013.01)

(58) Field of Classification Search
CPC ......... C07D 233/58; B01J 29/146; G01T 7/00
See application file for complete search history.

(56) References Cited

U.S. PATENT DOCUMENTS

| | | | | |
|---|---|---|---|---|
| 2005/0260441 A1* | 11/2005 | Thompson | .......... | C07F 15/0033 428/690 |
| 2006/0024522 A1* | 2/2006 | Thompson | .......... | C07F 15/0033 428/690 |
| 2011/0105761 A1 | 5/2011 | Strassner et al. | | |
| 2011/0303850 A1 | 12/2011 | Barillon et al. | | |
| 2014/0027646 A1 | 1/2014 | Zaitseva et al. | | |

OTHER PUBLICATIONS

Blackburn et al. "Intramolecular fluorescence quenching of anthracene by heterocyclic ligands" Journal of the Chemical Society, Perkin Transactions 2: Physical Organic Chemistry (1976), vol. 12, pp. 1452-1456.*
International Search Report for PCT/EP2014/055428 dated Mar. 31, 2014.
Dirk Meyer et al: "1,2,4-Triazole-Based Tunable Aryl/Alkyl Ionic Liquids", The Journal of Organic Chemistry, vol. 76, No. 1, (Jan. 7, 2011), pp. 305-308.
Xiaohong Cheng et al: "Self-Assembly of Imidazolium-Based Rod-like Ionic Liquid Crystals: Transition from Lamellar to Micellar Organization", Chemistry—A European Journal, vol. 16, No. 15, (Apr. 19, 2010), pp. 4588-4601.
Enrique Diez-Barra et al: "Reactivity of tetracyanoethylene oxide toward heteroaromatic compounds. Synthesis and structure of heterocyclic dicyanomethylides", The Journal of Organic Chemistry, vol. 47, No. 23, (Nov. 1, 1982), pp. 4409-4412.
Lijuan Shi et al: "Aggregation Behavior of Long-Chain N-Aryl Imidazolium Bromide in Aqueous Solution", Langmuir, vol. 27, No. 5, (Mar. 1, 2011), pp. 1618-1625.
Hiroto Yoshida et al: "Facile Synthesis of N-Alkyl-N'-arylimidazolium Salts via Addition of Imidazoles to Arynes", Organic Letters, vol. 4, No. 16, (Aug. 1, 2002) pp. 2767-2769.
G. Michael Blackburn et al: "Bonding of benzo[a]pyrene to nitrogen heterocycles by anodic oxidation", Journal of The Chemical Society, Chemical Communications, No. 2, (Jan. 1, 1974) p. 67.
Bjorn Wiegmann et al: "A New Framework of a Heteroleptic Iridium(III)-Carbene Complex as a Triplet Emitting Material", Organometallics, vol. 31, No. 15, (Aug. 13, 2012) pp. 5223-5226.
Michael Blackburn G et al: "Intramolecular fluorescence quenching of anthracene by heterocyclic ligands", Journal of The Chemical Society, Perkin Transactions 2, Chemical Society. Letchworth, GB, (Jan. 1, 1976) pp. 1452-1456.
Anupam Midya et al: "A new class of solid state ionic conductors for application in all solid state dye sensitized solar cells", Chemical Communications, vol. 46, No. 12, (Jan. 1, 2010) p. 2091.

* cited by examiner

Primary Examiner — Joseph R Kosack
(74) Attorney, Agent, or Firm — B. Aaron Schilman, Esq.; Stites & Harbison, PLLC

(57) ABSTRACT

The invention concerns a new family of discriminating molecules for neutron rays and gamma rays, and method for preparing the same. These molecules are also useful to detect radiation (X, gamma, electrons, protons, ions), and hence for the manufacture of instruments for radiation detection, industrial or medical dosimetry.

18 Claims, 13 Drawing Sheets

FAMILY OF DISCRIMINATING MOLECULES FOR NEUTRON AND GAMMA RAYS AND IONIC LIQUIDS

Figure 1:
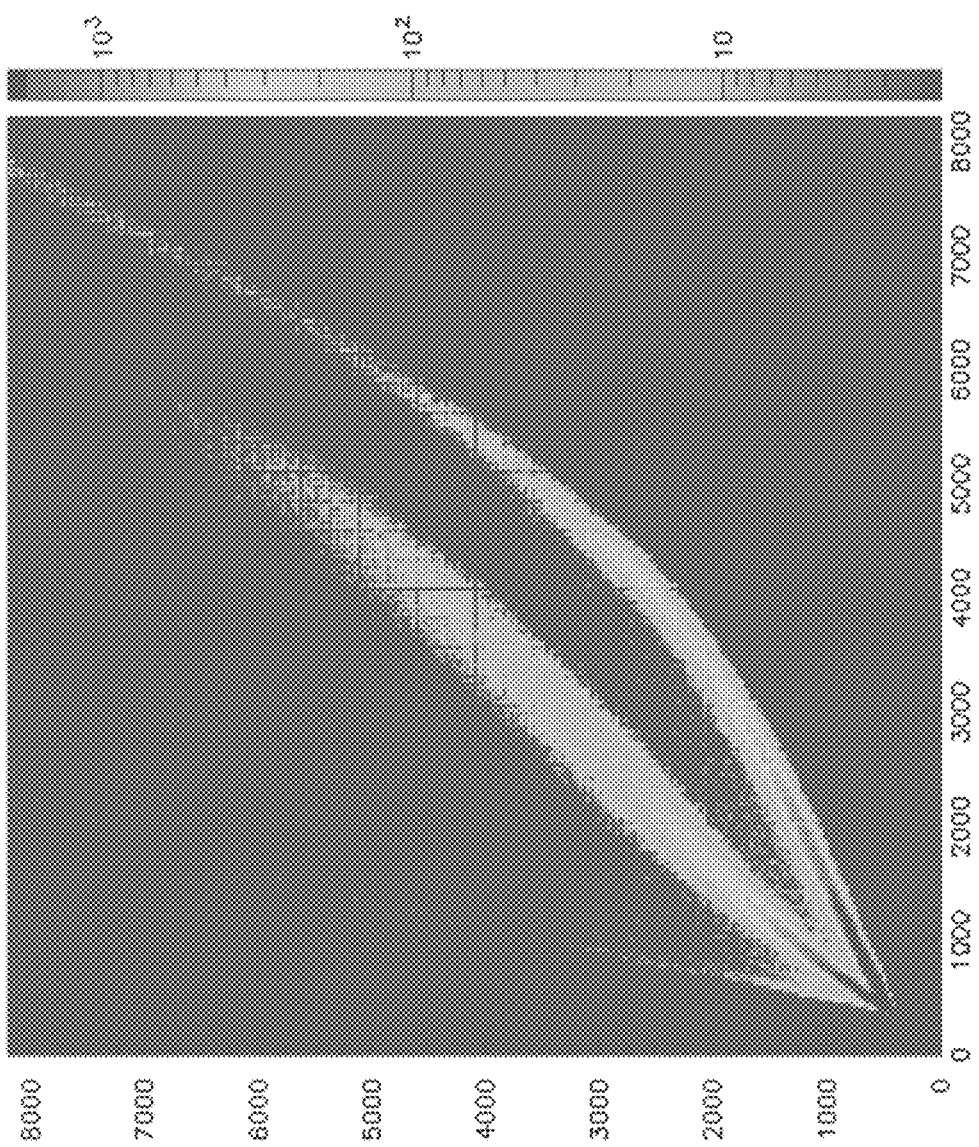

The present invention is directed towards a new family of discriminating molecules for neutron and gamma rays in particular, and the method for preparing the same. These molecules can be given particular use for the detection of nuclear radiation, in fundamental research or else in the fields of dosimetry and medical imaging.

As explained in application WO 2010/004228 (US 2011-0303850, EP 09784508), the production of electron-hole pairs by ionisation forms the first step, one of the fastest, for the relaxation of energy initially deposited by radiation in a medium. In the excited organic matter the formed pairs are generally composed of a quasi-free electron in the conduction band, geminate (electrically paired) with a much less mobile hole in the valence band.

Discrimination is based on the fact that the amount of energy dE deposited in a medium per unit of traveled distance, dx, by incident radiation differs according to whether this radiation is formed of photons or charged particles. With excitation by gamma photons derived from a radioactive source for example, the amount dE/dx is relatively low, which implies low ionisation densities and hence a relatively low production of electron-hole pairs. With excitation by neutrons different nuclear reactions occur, the most important being the (n,p) reaction during which a proton (p) is ejected from a nucleus by elastic collision with an incident neutron (n). This proton will naturally slow down in the medium via excitation and ionisation of the latter, producing geminate electron-hole pairs of same type as those produced with gamma radiation but with much stronger ionisation density.

The deferred recombination of the produced pairs being at the origin of fluorescence emission, this emission will be more intense when excited by neutrons (indirectly by protons) than by gamma photons. The comparison of fluorescence intensities emitted during the two types of excitation, photons and neutrons, therefore allows discrimination.

The discrimination between neutron and gamma radiation is generally performed using three types of methods:
  by measuring time-of-flight of gamma particles and neutrons;
  by using semiconductor detectors; or
  using scintillating molecules diluted in transparent plastic materials.

The method using measurements of times-of-flight is particularly complex to carry out at technical and operating level, in particular on account of the difficult access to a good time reference. It requires major technicality both for the material preparation of the experiment and for the conducting thereof. This technique, which nevertheless gives very accurate results, remains essentially dedicated to research laboratories and applications in scarcely harsh environments.

The method which, as active part, uses a detector in semiconductive material remains limited to strong fluences. In this field of application the main limitation to the use of conductive materials still lies in the fact that measurement is performed on the amount of charges produced or else on generated current. At all events, measurements remain little sensitive since the limit of current detection is in the region of one picoampere and therefore only corresponds to the production of about 10 million mobile charge carriers per second. The low sensitivity of this method is generally offset by an increase in detector sensing volume, but then new problems arise related to the overall decrease in conduction of the assembly and degradation of the detector's time response.

Measurements based on scintillation of dilute molecules are by far those most used.

When the irradiated medium contains luminescent molecules, the geminate recombination of electron-hole pairs resulting from primary ionisation leads, with defined yield, to differed fluorescence emission the intensity of which will be proportional to the density of the ionisation produced by radiation on its pathway. This intensity is stronger during the passing of a proton than during the passing of a photon due to higher loss of energy per unit distance traveled, dE/dx. Therefore with deferred fluorescence measurement it is possible to discriminate between fluorescence resulting from the passing of a proton [produced by a neutron during an (n,p) reaction] and fluorescence resulting from the passing of a photon. The comparison of the intensities of the two emitted fluorescence signals allows discrimination to be carried out. The difficulty of measurement essentially results from the fact that the fluorescence is only emitted during a very short time, a few hundred nanoseconds, after the passing of the primary radiation which therefore involves specific instrumentation operating with nanosecond time resolution. Since the intensity of fluorescence is globally weak, it can only be detected using photomultipliers. The fluorescence emission spectrum is independent of type of excitation and is only dependent on the type of chosen fluorophore. Detection sensitivity is much higher than could be expected from measurement of current since only a few thousand free charge carriers need to be produced in the media for detection to be possible.

Diluted scintillator molecules are generally oxazoles or oxadiazoles, even para-terphenyl or anthracene. All these molecules have nanosecond luminescence properties within a spectral domain ranging from 300 to 400 nm.

This method, based on recombination fluorescence after interception of the charges produced in the medium by the scintillator molecules, is by far the most rapid (nanosecond) and the most sensitive. In theory, the production of a single free charge in the medium is sufficient to produce detectable fluorescence and hence measurement. The method should therefore be 10 million times more sensitive than a method based on conduction. In current practice however, the fact that the dilution limit of a scintillator molecule in plastic is in the region of 0.01 mole/L, reduces sensitivity by a factor of 10 to 100. The other reducing factor of sensitivity is given by the solid angle of detection of light. It can be estimated at 100 to 1000. The use of a photomultiplier having a typical detection yield of 20% therefore reduces sensitivity by a factor of about 5. Overall, it can be estimated that fluorescence techniques are about 1000 times more sensitive than electrical techniques and that the main limitation is due to dilution of the fluorescent molecules. The use of aromatic fluorescent materials diluted in a liquid (benzene, xylene) or used in the pure solid state (p-terphenyl, anthracene) is possible.

The scintillators currently used for the detection of neutron radiation are essentially of three types:
  Liquid scintillators (NE213, BC501, BC501A): mixtures of xylene and naphthalene to which additives are added.
  Crystalline scintillators: organic and inorganic crystals (anthracene, stilbene, cerium-doped fluorophores) (see WO 20152/142365). This type of scintillator is difficult and costly to produce.

Scintillator plastics. The manufacture of these scintillators is low-cost.

Liquid and solid scintillators allow the detection and discrimination of neutrons and gamma rays whereas scintillator plastics can only detect the two types of radiation without discriminating between them except when using the time-of-flight technique. Also these scintillators can deform and become opacified over time (detection and discrimination give better results in a transparent material). However, all these scintillators have a major problem with regard to safety: they are flammable and the liquids are even explosive, toxic and harmful for the environment. The challenge is therefore to propose materials allowing discrimination between neutrons and gamma rays which meet standards of hygiene and safety so that their use can be envisaged in places such as nuclear plants, hospitals, airports, . . . where such scintillators are currently forbidden. In addition, it must be possible to place the new scintillators in a vacuum to prevent air from interfering with some radiation, which currently cannot be contemplated.

Application WO 2010/004228 describes a method allowing the preparation of solid, heat-stable materials (200° C.) having no measurable vapour pressure and able to discriminate between neutron and gamma rays. Oxazoles/imidazoliums have been synthesized and give good discrimination results. However the synthesis thereof requires seven to eight steps and their transparency is difficult to obtain.

OBJECTIVES OF THE INVENTION

It is therefore the objective of the invention to solve the above-cited technical problems whilst providing compounds of simple synthesis.

It is also the objective of the invention to provide novel molecules allowing improved detection of gamma, X, neutron and/or proton radiation.

A further objective of the present invention is to provide novel molecules allowing improved discrimination between proton/gamma, proton/X, neutron/gamma, neutron/X, alpha/gamma, alpha/X radiation.

A further objective of the invention is to provide instrumentation for radiation detection, industrial or medical dosimetry.

In particular, it is the objective of the invention to simplify the preparation of compounds previously synthesised using the method described in application WO 2010/004228.

DESCRIPTION OF THE INVENTION

The inventors have discovered a new family of discriminating molecules (or compounds). The synthesis method allows imidazoliums to be obtained in two or three steps starting from commercially available products. This synthesis method is universal since a large number of aryls or aromatic groups can be coupled.

Also, the properties of these new molecules are even further improved with regard to the detection and/or discrimination of the aforementioned radiation compared with those described in patent WO 2010/004228.

This new family of fluorescent molecules particularly allows the real-time and improved discrimination between neutron and gamma radiation.

Against all expectations, the compounds obtained first have fast fluorescence properties (nanosecond) emitting in the ultraviolet (400 nm), and secondly they have the properties of ionic liquids. When these molecules contain at least one fluorophore group, this imparts high fluorescence yields thereto similar to liquid scintillators but with numerous additional properties:

Non-measurable vapour pressure allowing use under a high vacuum;
Good thermal stability (up to 200° C.);
Non-flammability;
low toxicity;
liquid or solid state.

In addition to these properties, the customized preparation of molecules allows adjustment of the efficacy of initial interaction with radiation in order to increase energy loss (dE/dx) and hence the amount of emitted light. This can be obtained for example by adding a heavy atom (detection of photons), or by increasing the number of hydrogen atoms (detection of neutrons). Improved detection sensitivity is obtained, in pure and dilute media, insofar as the structure of the molecule and the parameters of interaction are better controlled. The luminescent molecules of the invention can therefore be used in scintillators.

According to the present invention, the term «fluorophore» designates a fluorescent group capable of absorbing energy at a specific wavelength and of re-emitting the energy at a different wavelength that is also specific. The amount and wavelength of re-emitted energy are dependent both on the fluorophore and on the chemical environment of the fluorophore.

Therefore a first subject of the invention concerns an imidazolium compound of formula (I):

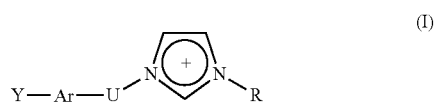

Where:

represents the imidazolium cation;

«Y—Ar—U» is a group comprising at least one $sp^3$ carbon atom;

«Y» necessarily present, is an «alkyl» or «O-alkyl» group, «alkyl» being defined as a saturated hydrocarbon radical optionally comprising one or more unsaturations, straight-chain or branched, having 1 to 30 carbon atoms, preferably 5 to 20 carbon atoms, optionally substituted;

«Ar» is optionally present and defined as an aromatic group, optionally substituted;

«U» is optionally present and defined as a saturated hydrocarbon radical, optionally comprising one or more unsaturations, straight-chain or branched having 1 to 30 carbon atoms, preferably 5 to 20 carbon atoms, optionally substituted;

«R» is a fluorophore aromatic group comprising at least one $sp^2$ carbon atom, optionally substituted;

wherein the imidazolium group is directly attached to the aromatic group «R» by a covalent bond between a nitrogen atom of the imidazolium group and an $sp^2$ carbon atom of the aromatic group, and wherein the imidazolium group is attached directly to the substituent «Y—Ar—U-» via a covalent bond between the other nitrogen atom of the imidazolium nucleus and a sp³ carbon atom of the said group «Y—Ar—U-».

In particular, the inventors have discovered that the molecules of the invention have luminescence properties. In the presence of a luminescent «R» group, these compounds allow most advantageous application to the detection and discrimination of radiation, in particular between neutrons and gamma rays.

The «R» group is an aromatic fluorophore group absorbing energy at a specific wavelength and re-emitting energy at a different wavelength that is also specific. The «R» group is fluorophore before being coupled to the imidazolium/imidazole portion of the compounds of the invention.

Advantageously the «R» group comprises at least one group or consists of a group selected from among: optionally substituted phenyl, optionally substituted naphthalene, optionally substituted fluorene, optionally substituted methylcarbazole and optionally substituted anthracene, optionally substituted pyrene, optionally substituted tetracene, a fluorescent protein e.g. GFP (green), YFP (yellow) and RFP (red), derivatives of xanthene such as: fluorescein, rhodamine, Oregon green, eosin and sulforhodamine 101 acid chloride (Texas red); cyanine or the derivatives thereof such as: indocarbocyanine, oxacarbocyanine, thiacarbocyanine and merocyanine; derivatives of naphthalene such as: 5-(dimethylamino)naphthalene-1-sulfonyl chloride(dansyl) and 1-[6-(Dimethylamino)-2-naphthalenyl]-1-propanone (prodan), a derivative of coumarin, a derivative of oxadiazole such as: pyridyloxazole, nitrobenzoxadiazole and benzoxadiazole; a derivative of pyrene such as: cascade Blue®, a derivative of oxazine such as: 9-diethylamino-5-benzo[a]phenoxazinone (Nile red), a derivative of benzophenoxazine, in particular a derivative of benzo[a]phenoxazine (Nile blue), a derivative of benzo[b]phenoxazine, (9-dimethylamino-10-methyl-benzo[a]phenoxazin-5-ylidene)ammonium chloride (cresyl violet), 5.9-Bis(ethylamino)-10-methylbenzo[a]phenoxazin-7-ium (oxazine 170); a derivative of acridin, such as: proflavin, N,N,N',N'-Tetramethylacridine-3.6-diamine (acridine orange), 3.6-diamino-2.7-dimethylacridine (acridine yellow); a derivative of arylmethin such as: auramine, cTris(4-(dimethylamino)phenyl)methylium chloride (crystal violet), 4-[(4-dimethylaminophenyl)phenyl-methyl]-N,N-dimethylaniline (malachite green); a derivative of tetrapyrrol such as: porphin, phtalocyanine, bilirubin, a 4.4-difluoro-4-bora-3a.4a-diaza-s-indacene (BODIPY), BODIPY FI, BODIPY TMR, BODIPY 581/591, BODIPY 630/650, BODIPY 650/665. According to one variant, «R» is a polyaromatic group, in particular a hydrocarbon polyaromatic group.

According to one variant, the compound is selected from among a compound of formula (Ia), (Ib), (Ic), (Id), (Ie) below:

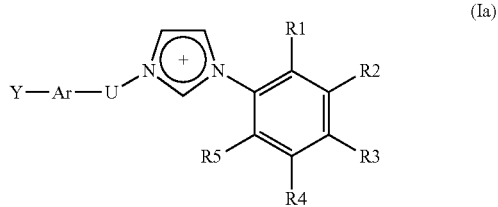

(Ia)

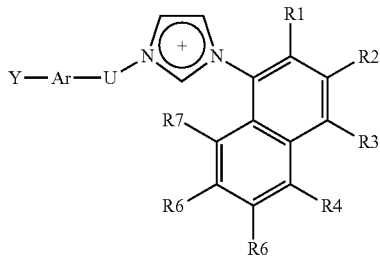

(Ib)

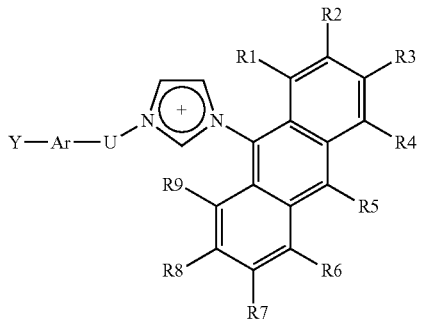

(Ic)

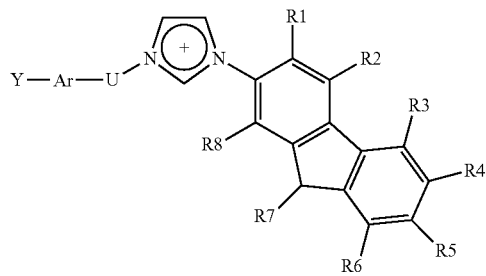

(Id)

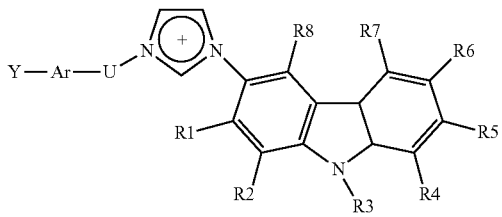

(Ie)

where:
«Y—Ar—U» is such as defined in the invention;
R1, R2, R3, R4, R5, R6, R7, R8 and R9 are each independently:
H,
F, Cl, Br, I,
$C_1$-$C_{30}$ alkyl group, $C_3$-$C_7$ cycloalkyl groups, $C_6$-$C_{10}$ aryl, heteroaryl, aralkyl, heteroarylalkyl groups wherein the said alkyl or aryl groups are optionally substituted by 1 to 3 $R^{20}$ groups,
$R^{20}$ being selected from among $OR^{22}$, $NR^{23}R^{24}$, NHOH, $NO_2$, CN, $CF_3$, $C_1$-$C_6$ alkyl, $C_2$-$C_6$ alkenyl $C_2$-$C_6$ alkynyl, $C_6$-$C_{10}$ aryl, aralkyl, =O, C(=O)$R^{22}$, $CO_2R^{22}$, OC(=O)$R^{22}$, C(=O)$NR^{23}R^{24}$, OC(=O)$NR^{23}R^{24}$, $NR^{21}$C(=S)$R^{22}$ or $S(O)_yR^{22}$;
$R^{22}$ on each occurrence is independently selected from among H, $C_1$-$C_{30}$, alkyl, preferably $C_5$-$C_{20}$, $C_6$-$C_{10}$ aryl and aralkyl;
$R^{23}$ and $R^{24}$ on each occurrence are independently selected from among H, $C_1$-$C_{30}$ alkyl, preferably $C_5$-$C_{20}$, and $C_6$-$C_{10}$ aryl, or else $R^{23}$ and $R^{24}$ together with the hydrogen atom to which they are attached form a heterocyclic group with 3 to 7 members.

According to one variant, one, two or three from among R1, R2, R3, R4, R5, R6, R7, R8 and R9 represent a $C_1$-$C_{30}$ alkyl group and preferably $C_5$-$C_{20}$, optionally substituted, or a $C_1$-$C_{30}$ O-alkyl group preferably $C_5$-$C_{20}$, optionally substituted in particular CH; the others each representing a hydrogen atom.

According to one variant, R1, R2, R3, R4, R5, R6, R7, R8 and R9 are each independently: a hydrogen atom, $C_1$-$C_{30}$ alkyl group, and preferably $C_5$-$C_{20}$, optionally substituted, or a $C_1$-$C_{30}$ O-alkyl group preferably $C_5$-$C_{20}$, optionally substituted. Among the preferred groups, mention can be made of the following groups: butyl, pentyl, hexyl, octyl, nonyl, decyl, dodecyl, hexadecyl, octadecyl, isopropyl, tert-butyl, 2-ethylhexyl, 2-methylbutyl, 2-methylpentyl, 1-methylpentyl and 3-methylheptyl.

Advantageously, the compound of the invention is associated with an «$A^-$» counter-anion.

Preferably, PC is an anion selected from among a halide, $P(R^4)_6^-$, $B(R^4)_4^-$, $SCN^-$, $(R^5SO_2)_2N^-$, $R^5OS_3^-$, $R^5SO_3^-$, carborane, carbonate, hydrogen carbonate, alcoholate, carboxylate, amide, phosphate, $SiF_6^-$, $SbF_6^-$, $I_3^-$, nitrate, halide oxide, silicate, sulfate, sulfonate, cyanide, carbanions, or metallate, where:

$R^4$ on each occurrence is a group independently selected from among a halogen atom, $C_1$-$C_6$ alkyl group, $C_6$-$C_{10}$ aryl group, aralkyl group;

$R^5$ on each occurrence is a group independently selected from among $C_1$-$C_{20}$ alkyl, $C_1$-$C_{20}$ haloalkyl, $C_6$-$C_{10}$ aryl, aralkyl. Further preferably, $A^-$ is selected from among $Br^-$, $I^-$, $PF_6^-$, $BF_4^-$, $(CF_3SO_2)_2N^-$, $C_{12}H_{25}OSO_3^-$, $C_{16}H_{33}OSO_3^-$, $CF_3SO_3^-$.

According to one advantageous variant, «U» is present and represents a $CH_2$ group, «Ar» is present and represents an aryl group, and «Y» represents a $CnH_{2n+1}$ or O—$CnH_{2n+1}$ alkyl group where n is a number ranging from 1 to 30 and preferably 5 to 20.

According to one embodiment, «Ar» and «U» are present and «U» represents a saturated, straight-chain hydrocarbon group having 1 to 30 carbon atoms, preferably 5 to 20 carbon atoms, optionally substituted.

According to one advantageous variant «U» is a $CH_2$ group.

According to another advantageous variant «Ar—U» is a benzyl group.

According to one advantageous variant, «Y» is a CnH2n+1 or O—CnH2n+1 alkyl group where is n is a number ranging from 1 to 30 and preferably 5 to 20.

According to another advantageous variant, «Y» is a CnH2n+1 or 0-CnH2n+1 alkyl group where n is a number ranging from 1 to 30 and preferably 5 to 20 and «U» and «Ar» are absent.

According to the variant in which «Ar» is absent, the compounds of the invention can be represented by general formula (I):

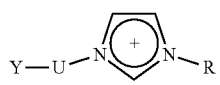

According to the variant where «Ar» and «U» are absent, the compounds of the invention can be represented by general formula (I)

According to the present invention, the alkyl radicals represent straight-chain or branched, saturated hydrocarbon radicals having 1 to 30 carbon atoms, preferably 5 to 20 carbon atoms. Preferably «Y» is selected from the group formed by the following radicals: methyl, ethyl, propyl, butyl, pentyl, hexyl, octyl, nonyl, decyl, dodecyl, tetradecyl, pentadecyl, hexadecyl, heptadecyl, octadecyl, isopropyl, tert-butyl, 2-ethylhexyl, 2-methylbutyl, 2-methylpentyl, 1-methylpentyl and 3-methylheptyl. When they are straight-chain particular mention can be made of the methyl, ethyl, propyl, butyl, pentyl, hexyl, octyl, nonyl, decyl, dodecyl, hexadecyl and octadecyl radicals.

When they are branched or substituted by one or more alkyl radicals, particular mention can be made of the isopropyl, tert-butyl, 2-ethylhexyl, 2-methylbutyl, 2-methylpentyl, 1-methylpentyl and 3-methylheptyl radicals.

Such as they are used in the entire description of the invention the following terms, unless otherwise indicated, are to be construed as having the following meanings.

The term «haloalkyl» designates an alkyl radical substituted by one or more halogen atoms. The haloalkyl radicals include the perhaloalkyl radicals and in particular the perfluoroalkyl radicals of formula $CnF_{2n+1}$.

The term «halogen» designates a chlorine, bromine, iodine or fluorine atom.

The term «cycloalkyl» means a mono- or multicyclic non-aromatic ring system with 3 to 10 carbon atoms, preferably 5 to 7 carbon atoms. As an example of monocyclic cycloalkyl particular mention can be made of cyclopentyl, cyclohexyl, cycloheptyl and the like. As an example of multicyclic cycloalkyl group particular mention can be made of 1-decaline, norbornyl or adamant-(1 or 2-)yl.

The term «alkenyl» designates an aliphatic hydrocarbon group containing a double carbon-carbon bond and which may be straight-chain or branched having 2 to 6 carbon atoms in the chain. Branched means that one, or more, lower alkyl groups, such as methyl, ethyl or propyl are linked to a straight alkenyl chain. As an example of an alkenyl group, particular mention can be made of ethenyl, propenyl, n-butenyl, i-butenyl, 3-methylbut-2-enyl or n-pentenyl.

The term «alkynyl» designates an aliphatic hydrocarbon group containing a triple carbon-carbon bond and which may be straight-chain or branched having 2 to 6 carbon atoms in the chain, preferably 2 to 4 carbon atoms. Branched means that one, or more, lower alkyl groups such as methyl, ethyl or propyl, are linked to a straight alkynyl chain. As examples of alkynyl groups, particular mention can be made of ethynyl, propynyl, n-butynyl, 2-butynyl, 3-methylbutynyl and n-pentynyl.

The term «aryl> designates an aromatic monocyclic or multicyclic ring system having 5 to 20 carbon atoms. As examples of aryl groups particular mention can be made of optionally substituted phenyl, optionally substituted naphthalene, optionally substituted fluorene, optionally substituted methylcarbazole and optionally substituted anthracene, optionally substituted pyrene, optionally substituted tetracene, bodipy, thiophene and polythiophene.

The term «substituted» designates a substitution of one hydrogen atom by one halogen atom or by a group from among alkyl, haloalkyl, cycloalkyl, alkenyl, alkynyl, aryl, a heterocyclic group such as a heterocycloalkyl, a heteroaryl.

The term «aralkyl» designates an aryl-alkyl- group wherein the aryl and alkyl are such as described in the present document. As examples of aralkyl groups, particular mention can be made of benzyl, 2-phenethyl and naphthienemethyl.

The term «heterocyclic group» designates a mono- or multicyclic, substituted or unsubstituted carbocyclic group wherein the cyclic part comprises at least one heteroatom such as O, N, S or B. The nitrogen and sulfur may optionally be oxidised, and the nitrogen may optionally be substituted in the aromatic rings. The heterocyclic groups comprise the heteroaryl groups and heterocycloalkyl groups.

The term «heterocycloalkyl» designates a cycloalkyl group wherein one or more ring carbon atoms are substituted by at least one atom selected from among O, N or S. As an example of heterocycloalkyl group, particular mention can be made of the following groups: pyrrolidinyl, pyrrolinyl, imidazolidinyl, imidazolinyl, pirazolidinyl, pirazolinyl, pyrazalinyl, piperidyl, piperazinyl, morpholinyl, thiomorpholinyl, tetrahydrofuranyl, dithiolyl, oxathiolyl, oxadiazolyl, oxathiazolyl, pyranyl, oxazinyl, oxathiazinyl and oxadiazinyl.

The term «heteroaryl» or «heteroaromatic» designates a group containing 5 to 10 carbon atoms wherein at least one ring carbon is replaced by at least one atom selected from among —O—, —N—, —S— or B. As example of a heteroaryl group particular mention can be made of pyrrolyl, furanyl, thienyl, pirazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl and quinoxalinyl. Also included in the definition of "heteroaryl" groups are the fused ring systems which particularly include the ring systems in which the aromatic ring is fused with a heterocycloalkyl ring. As an example of such fused ring systems particular mention can be made of phthalamide phthalic anhydride, indoline, isoindoline and tetrahydroisoquinoline.

The term «heteroarylalkyl» designates an aryl-heteroaryl-group in which the heteroaryl and the alkyl are such as described in the present document.

The terms «alkylene, cycloalkylene, heterocycloalkylene, arylene, heteroarylene» respectively designate bivalent alkyl, cycloalkyl, heterocycloalkyl aryl and heteroaryl groups, these groups being such as defined above.

Preferably, $X^-$ is an anion selected from among a halide, $P(R^4)^{6-}$, $B(R^4)^{4-}$, $SCN^-$, $(R^5SO_2)_2N^-$, $R^5OSO_3^-$, $R^5SO_3^-$, carborane, carbonate $(CO_3^{2-})$, hydrogen carbonate $(HCO_3^-)$, alcoholate $(R^4O^-)$, carboxylate $(R^4COO^-)$, amide $(NH_2^-)$, phosphate $(PO_4^-)$, $SiF_6^-$, $SbF_6^-$, $I_3^-$, nitrate $(NO_3^-)$, halide oxide, silicate, sulfate $(SO_4^-)$, sulfonate $(R^4SO_3^-)$, cyanide $(CN^-)$, carbanions, or metallate;
where:
$R^4$ on each occurrence is a group independently selected from among a halogen atom, $C_1$-$C_6$ alkyl group, $C_6$-$C_{10}$ aryl group, aralkyl group;
$R^5$ on each occurrence is a group independently selected from among $C_1$-$C_{20}$ alkyl, $C_1$-$C_{20}$ haloalkyl, $C_6$-$C_{10}$ aryl, aralkyl.

The term "metallate" designates an anionic complex containing a metal, in particular a transition metal complexed with several ligands, for example a chalcogen such as oxygen or cyanide group. Preferably, the metallate anion is a cyanometallate or oxometallate group.

The term "carborane" designates a molecule formed of boron, carbon and hydrogen atoms and carrying a negative charge. As an example, mention can be made of $CB_{11}H_{12}^-$.

The term "halide oxide" designates oxides of formula $HalO_x^-$ where Hal is Br, Cl or I and x is an integer between 1 and 4. As an example, mention can be made of $ClO_4^-$, $IO_3^-$. The term "carbanion" designates a compound comprising a carbon atom carrying a negative charge. As an example $(CF_3SO_2)_3C^-$ can be cited.

More preferably, $X^-$ is selected from among $Cl^-$, $Br^-$, $PF_6^-$, $BF_4^-$, $(CF_3SO_2)_2N^-$, $C_{12}H_{25}OSO_3^-$, $C_{16}H_{33}OSO_3^-$, $CF_3SO_3^-$. According to one variant, $X^-$ is $PF_6^-$. According to one variant, $X^-$ is $BF_4^-$.

A further subject of the invention concerns a material, in particular a transparent plastic material comprising or formed of a compound such as defined above.

The invention also concerns a fluorophore solid or liquid material comprising or formed of a fluorophore compound, the said fluorophore compound comprising an imidazolium group directly attached to an aromatic fluorophore group via a covalent bond between a nitrogen atom of the imidazolium group and a carbon atom of the said aromatic group. Advantageously, the solid or liquid fluorophore material is a transparent plastic material.

Preferably, the fluorophore compound is a compound such as defined in the invention including all variants and embodiments and the combinations thereof.

According to a second aspect the invention concerns the use of these molecules for their fluorophore properties. Therefore the invention concerns the use of a fluorophore compound comprising an imidazolium group directly attached to an aromatic fluorophore group via a covalent bond between a nitrogen atom of the imidazolium group and a $sp^2$ carbon atom of the said aromatic group, or a material such as defined in the invention for the detection of gamma, X, neutron, proton radiation.

According to one variant, the invention concerns the use for discrimination between proton/gamma, proton/X, neutron/gamma, neutron/X, alpha/gamma and alpha/X rays.

According to a further aspect the invention concerns the use of a fluorophore compound comprising an imidazolium group directly attached to an aromatic group via a covalent bond between a nitrogen atom of the imidazolium group and a $sp^2$ carbon atom of the said aromatic group, or a material such as defined in the invention, for the manufacture of an instrument for radiation detection, industrial or medical dosimetry. Preferably the compound is a compound such as defined in the invention including all variants and embodiments and the combinations thereof.

According to a third aspect, the invention also concerns a synthesis method with which to prepare ionic compounds of the invention with the desired group.

In particular, the invention concerns a method for preparing a compound comprising an imidazolium group directly attached to an aromatic group via a covalent bond between a nitrogen atom of the imidazolium group and a carbon atom of the said aromatic group, the said method comprising a coupling reaction between an aromatic group and an imidazole group through the creation of a covalent bond between a $sp^2$ carbon atom of the aromatic group and a nitrogen atom of the imidazole group, in the presence of a zeolite NaY comprising copper(II) and a base, preferably via Ullmann-type coupling.

According to one particular embodiment, the invention concerns the preparation of a formula (I) compound of the invention, the said method comprising:

(i) a coupling reaction of an aromatic group «R» with an imidazole group through the creation of a covalent bond between a sp² carbon atom of the aromatic group and a nitrogen atom of the imidazole group, in the presence of a zeolite NaY containing copper(II) and a base, preferably via coupling of Ullmann type; and (ii) a coupling reaction of a «Y—Ar—U» group comprising at least one sp³ carbon atom with an imidazole group through the creation of a covalent bond between the sp³ carbon atom of the «Y—Ar—U» group and a nitrogen atom of the imidazole group, preferably via nucleophilic substitution, preferably using a halogen-containing reactive «Y-Ar-U» group.

According to one variant, step (i) corresponds to the following reaction:

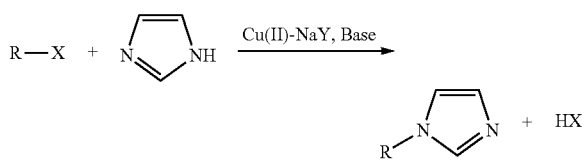

where X is a halogen atom, the reaction preferably being conducted in the presence of microwave radiation.

According to one particular embodiment, step (ii) corresponds to the following reaction:

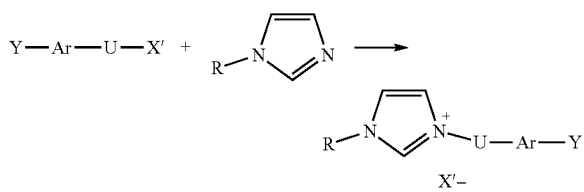

where X'- is a halogen atom and «-» is the negative charge of this atom.

Preferably the compound:

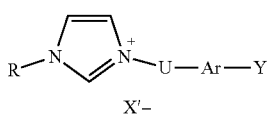

is caused to react with a salt of the desired A⁻ anion to obtain, via anion metathesis, the following compound:

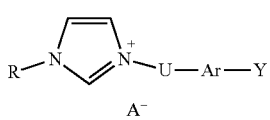

Preferably the salt of anion A⁻ is a lithium, sodium or potassium salt.

The catalyst is simple to prepare: the zeolite NaY is placed in the presence of copper sulfate dissolved in water and left under agitation for 24 hours. The zeolite impregnated with copper(II) is recovered by filtration, oven-dried (100° C.) and calcined at 550° C. for 4 hours. Particular reference can be made to the publication by M. L. Kantam, B. P. C. Rao, B. M. Choudrary, R. S. Reddy, Synlett, 2006, 14, 2195-2198. doi: 10.1055/s-2006-949615.

For coupling of Ullmann type (J. Hassan, M. Sevignon, C. Gozzi, E. Schulz, M. Lemaire, «Aryl-Aryl Bond Formation One Century after the Discovery of the Ullmann Reaction», Chemical Reviews, vol. 102, 2002, p. 1359-1470), the reagents are heated in a sealed tube for 72 hours for example at 180° C. using a sand bath. To collect the reaction product it is sufficient to re-dissolve in an organic solvent such as dichloromethane followed by filtration to remove the zeolite and base (potassium carbonate). The imidazole derivative thus obtained is purified using column chromatography for example.

Although no solvent or inert atmosphere are used, it is necessary to heat the reaction mixture for coupling of the imidazole and aryl, for example by heating to a temperature of 180° C. for 72 hours.

Advantageously, the reaction is conducted in the presence of microwave radiation. With this method the inventors were able to obtain a substantial reduction in reaction time. It is possible to reduce a reaction time of 72 hours (in a sealed tube heated with a sand bath) down to less than 3 hours with the same yields.

Microwaves are electromagnetic waves having a wavelength of between 30 cm (1 GHz) and 1 mm (300 GHz).

The base is preferably selected from among a potassium or caesium carbonate, potassium phosphate, caesium phosphate, LiOH, NaOH or KOH.

Advantageously, the method of the present invention does not require any solvent. In the prior art, the synthesis methods require the use of a solvent (dimethylformamide, dimethylsulfoxide, toluene . . . ), which is avoided in one embodiment of the present invention. However the invention covers the use of a solvent according to one variant.

With the present invention it is possible to avoid the use of amino ligands (carbene, phenanthroline, L-proline . . . ).

This method allows the use of solvents, inert atmosphere and costly ligands to be avoided and allows the compounds of the invention to be prepared in only two or three steps. In addition, with the method of the invention it is possible to use commercially available molecules.

Most advantageously, the use of microwave radiation for coupling of Ullmann type allows a significant reduction in reaction time. The reaction time can be shortened from 72 hours to less than 3 hours.

The first step of the synthesis is the performing of Ullmann-type coupling between an imidazole i.e. a molecule comprising an imidazole group, and a molecule carrying a halogen-containing aromatic group i.e. carrying a halogen atom on a carbon atom, this halogen atom to be later replaced by imidazole.

At the second step, the imidazole obtained is caused to react with a molecule defined by «Y-Ar-U» to create a covalent bond between the imidazole and a sp³ carbon atom of this molecule.

According to one variant, this second step is an N-alkylation step, i.e. the imidazole is reacted with an alkyl radical to create an N-alkyl bond between the alkyl radical and the nitrogen atom of the imidazole (a nitrogen atom not carrying the aromatic group grafted by Ullmann coupling).

At an optional third step, the halide anion is exchanged to obtain a fluorophore compound when the molecule comprising the aromatic group is fluorophore. This third step can be performed in a biphasic medium.

The potassium, lithium or sodium salt of the desired anion can be used.

Optionally the said method may also comprise the step to isolate the product obtained.

The method of the invention is of particular interest since it can be extrapolated to industrial scale on account of the low number of synthesis steps, the reagents used which are commercial reagents and the reaction equipment which can be used on a larger scale for industrial reactions.

It was observed that the luminescence properties are maintained for all the pure compounds in the solid or liquid state. This therefore allows advantageous use of materials in the solid or liquid state.

Therefore the invention also concerns solid or liquid materials comprising or formed of the compounds of the invention.

The compounds of the invention can replace organic scintillator liquids. Therefore the invention particularly covers the use of compounds of the invention, solid or liquid, for the detection and/or identification of fast and/or slow neutrons. By «fast neutrons» is meant neutrons having kinetic energy higher than 100 keV. By «slow neutrons» is meant neutrons having kinetic energy lower than 1 keV.

Thermogravimetric analyses showed that the compounds of the invention are stable up to 200° C., and it can therefore be envisaged that they meet all hygiene and safety rules.

In particular the invention covers devices comprising the compounds of the invention, adapted for use in nuclear plants, hospitals, airports or similar places.

Since the compounds of the invention do not have any measurable vapour pressure they can be used in a vacuum.

Among the applications of the compounds of the invention mention can be made of industrial dosimetry (radiation protection, dosimetry) and medical dosimetry, medical imaging and animal imaging, molecular electronics in particular for the preparation of light-emitting diodes or organic lasers, in biology in particular for coupling or with biological labels (medical diagnosis) or for molecular electronics. Particular reference is made to siRNA transfection (Mesomorphic Imidazolium salts: New vectors for efficient siRNA transfection, J. Am. Chem. Soc. 2009, 131, 13338-13346).

The specific applications of the compounds of the invention are dependent on the molecule under consideration and vary in relation to the type of anion, cation (starting imidazole) and aromatic group which in particular is to be used as fluorophore.

It is envisaged that the use of compounds of the invention allows lowering of the detection threshold and sensitivity of existing installations in fields such as nuclear safety (radiation protection, proliferation of nuclear waste or weapons, nuclear reactor) and fundamental research.

To characterize a product and verify the purity thereof conventional analysis methods exist such as nuclear magnetic resonance (NMR), infrared spectroscopy (IR), ultraviolet/visible (UV/Visible) spectroscopy and elementary analysis. Specific techniques have been developed to identify and characterize mesophases: Polarized Optical Microscopy (POM), thermal analysis (thermogravimetric analysis and differential scanning calorimetry), X-ray diffraction of the mesophase and dilatometry.

These techniques were used to characterize the synthesised compounds.

Advantageously the compounds of the invention can be used pure i.e. in the form of a material essentially formed of at least one compound of the invention. A strong concentration advantageously allows an increase in the efficacy of radiation detection accordingly. The previously described compounds U (NE213 or BC501) did not allow the use of strong concentrations since their radiation detection power decreased on and after a certain concentration. The invention therefore represents a significant improvement in this respect. The invention also covers the use of the compounds of the invention in dilute form as filler in polymer matrixes and as constituents of composite materials. The concentration of the compounds of the invention can range from 1 to 80% by weight in a polymer or in a solvent.

FIGURES

FIG. 1: neutrons/gamma discrimination of NE213 via a study of light pulse shapes (PSD method). This characterization is used in the analysis in the form of signals delivered by a detector such as DEMON formed of NE213 and irradiated by an AmBe source: integration of the charge of the total signal (Qtot) compared with the charge of the slow component (Qslow) allows discrimination between neutrons and gamma rays. It is to be pointed out that since a neutron is a neutral particle it cannot be detected directly but must first be converted to a charged particle (e.g. a proton) by nuclear reaction and it is the secondary particle which interacts with the detection material.

Figure 2:
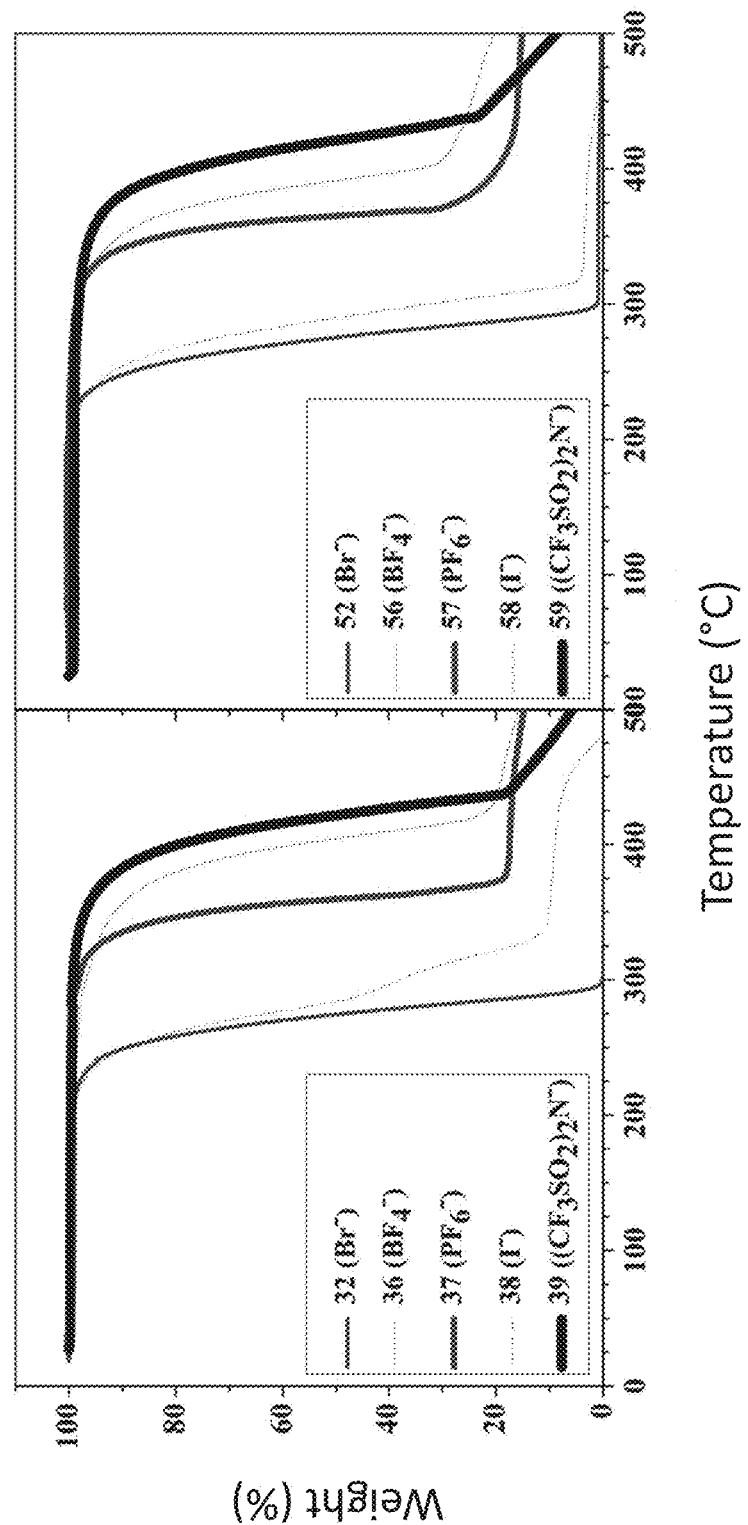

FIG. 2: Thermogravimetric analysis of compounds 32, 36 to 39, 52 and 56 to 59. Note: concerning the X-axis (temperature): 500 in the left-hand graph corresponds to 0 in the right-hand graph.

Figure 3:
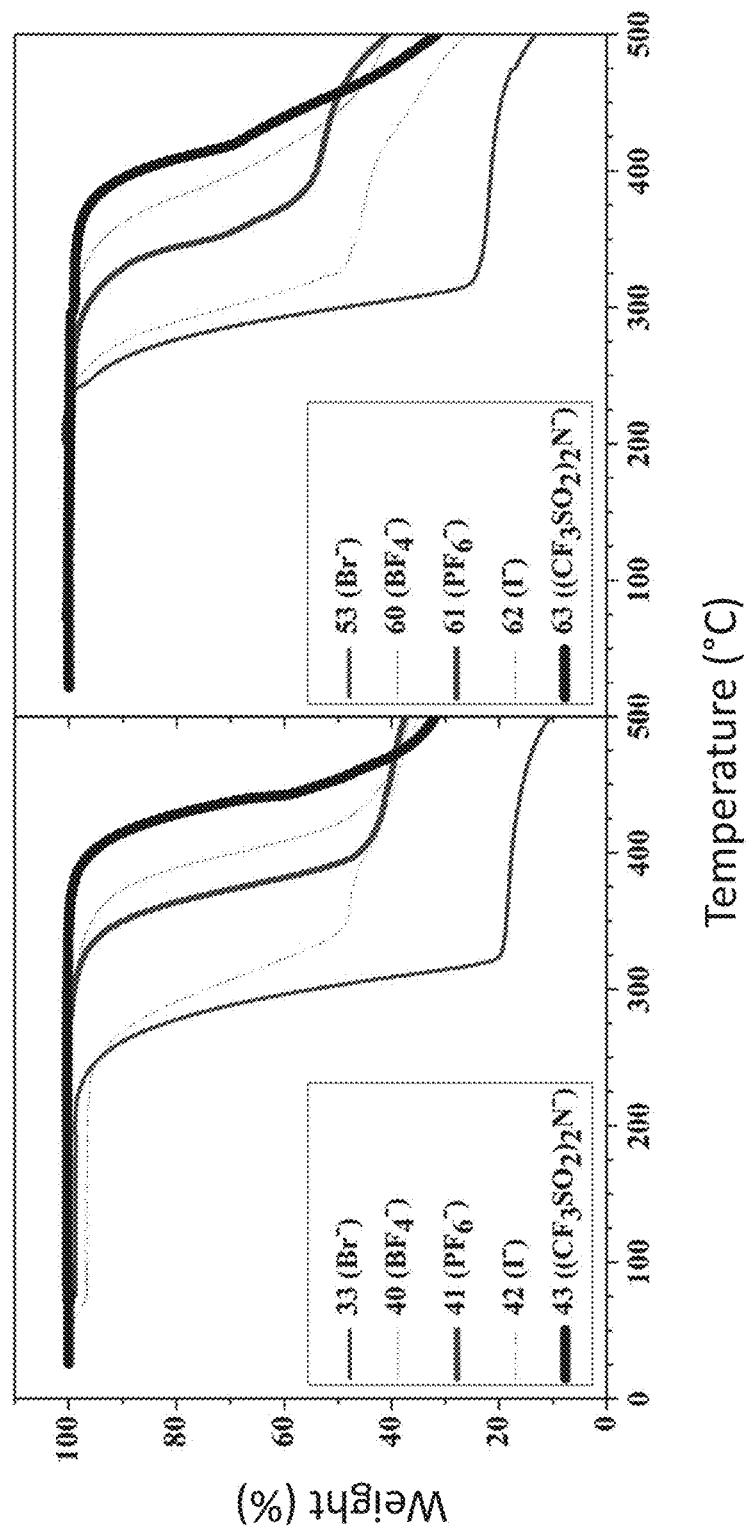

FIG. 3: Thermogravimetric analysis of compounds 33, 40 to 43, 53 and 60 to 63. Note: concerning the X-axis (temperature): 500 in the left-hand graph corresponds to 0 in the right-hand graph.

Figure 4:
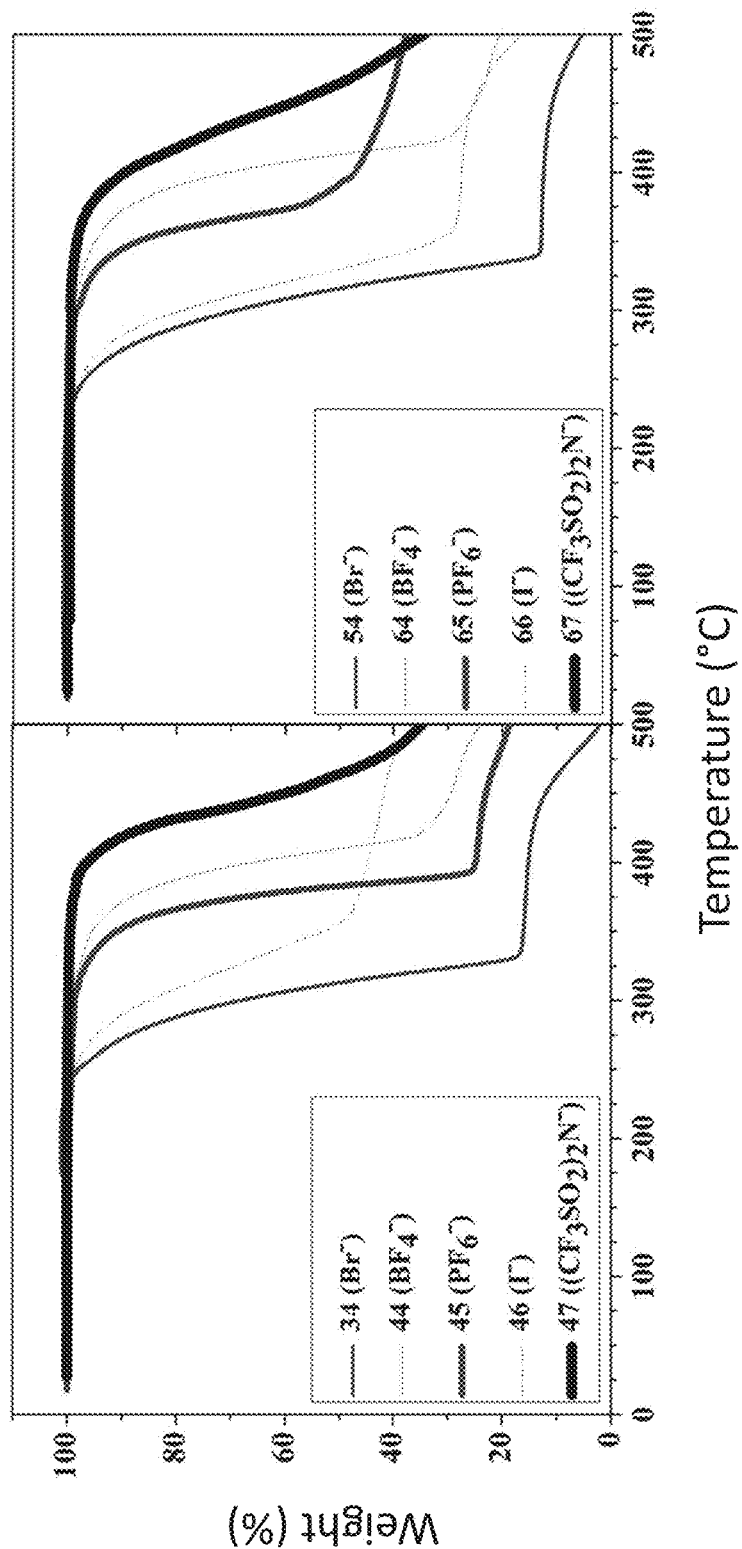

FIG. 4: Thermogravimetric analysis of compounds 34, 44 to 47, 54 and 64 to 67. Note: concerning the X-axis (temperature): 500 in the left-hand graph corresponds to 0 in the right-hand graph.

Figure 5:
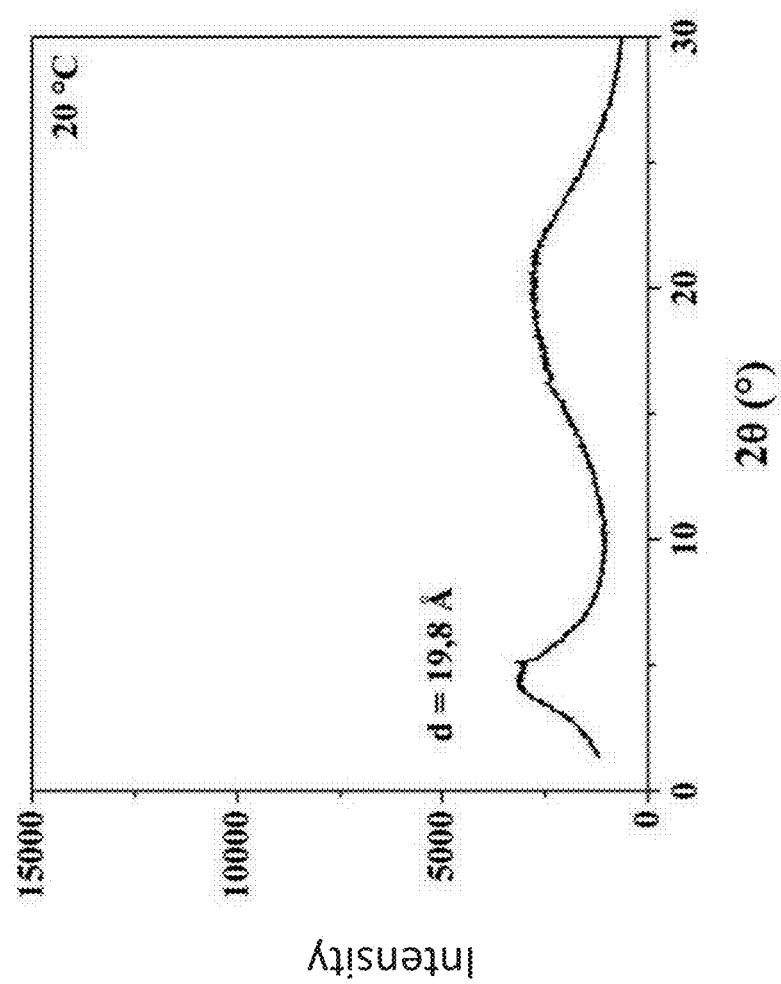

FIG. 5: Picture of X-ray diffraction of compound 45 recorded in the amorphous state (T=20° C.).

Figure 6:
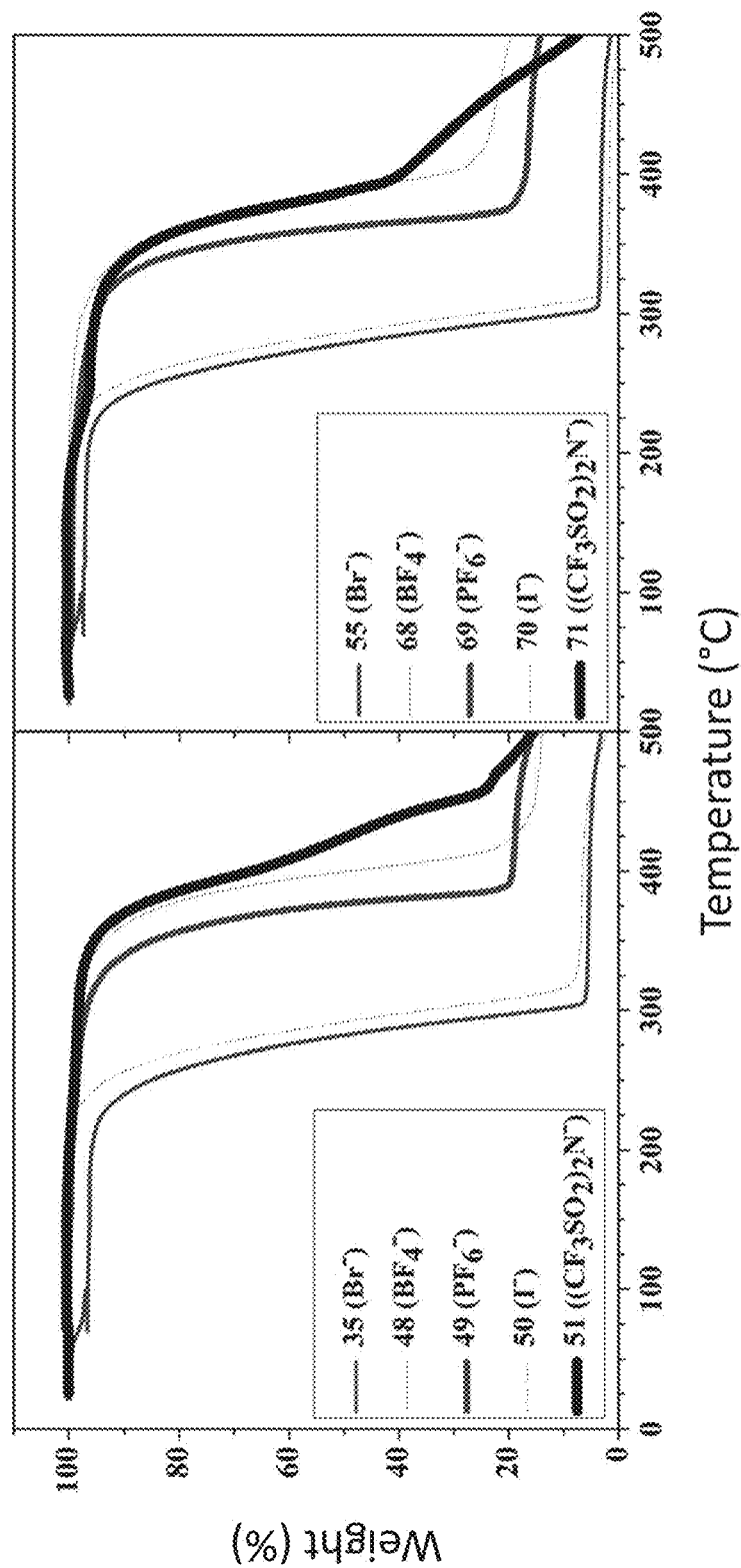

FIG. 6: Thermogravimetric analysis of compounds 35, 48 to 51, 55 and 68 to 71. Note concerning the X-axis (temperature): 500 in the left-hand graph corresponds to 0 in the right-hand graph.

Figure 7:
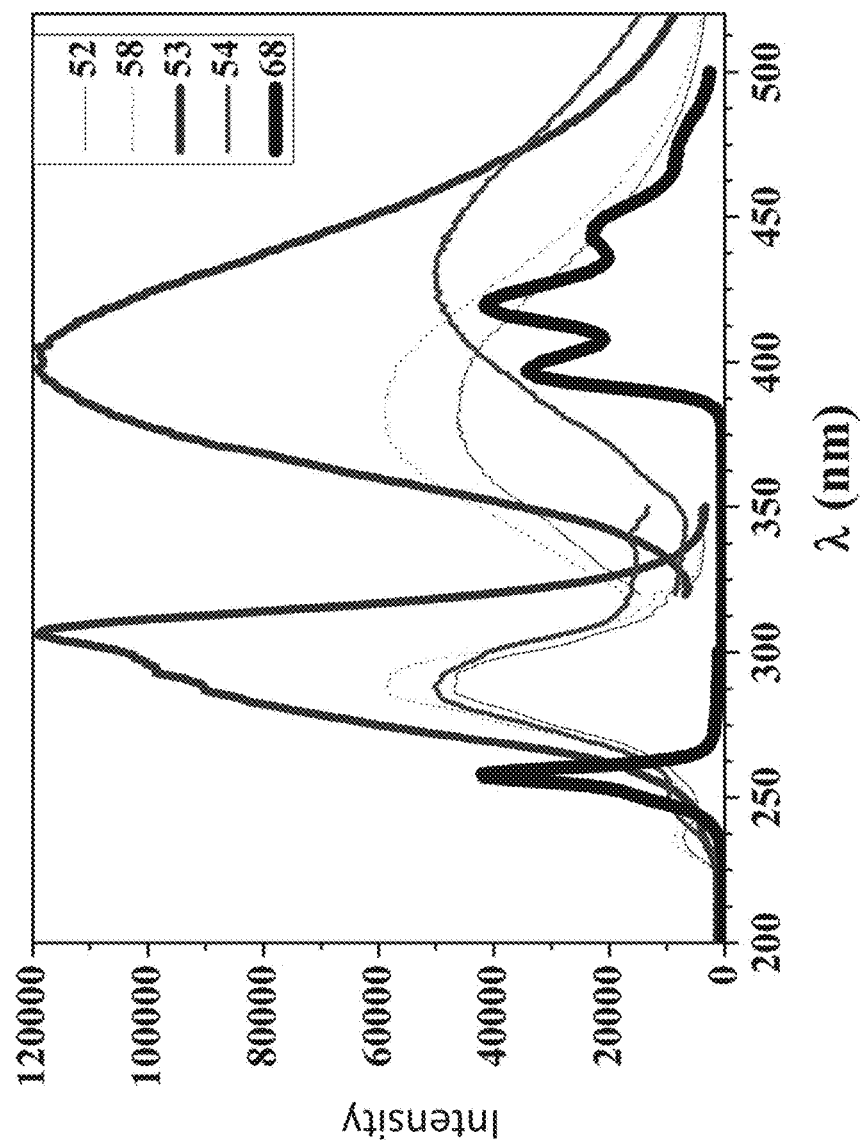

FIG. 7: Luminescence spectra of compounds 52, 53, 54, 58 and 68.

Figure 8:
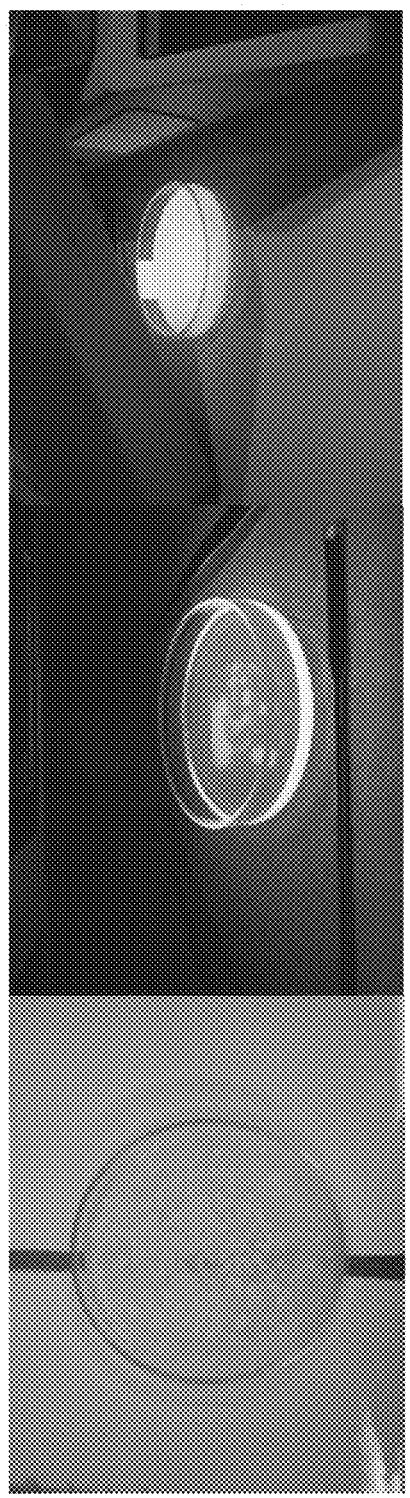

FIG. 8: Photos of material 60 in the solid state (left), illuminated with a UV lamp in the liquid state with onset of crystallisation (centre) and solid (right).

Figure 9:
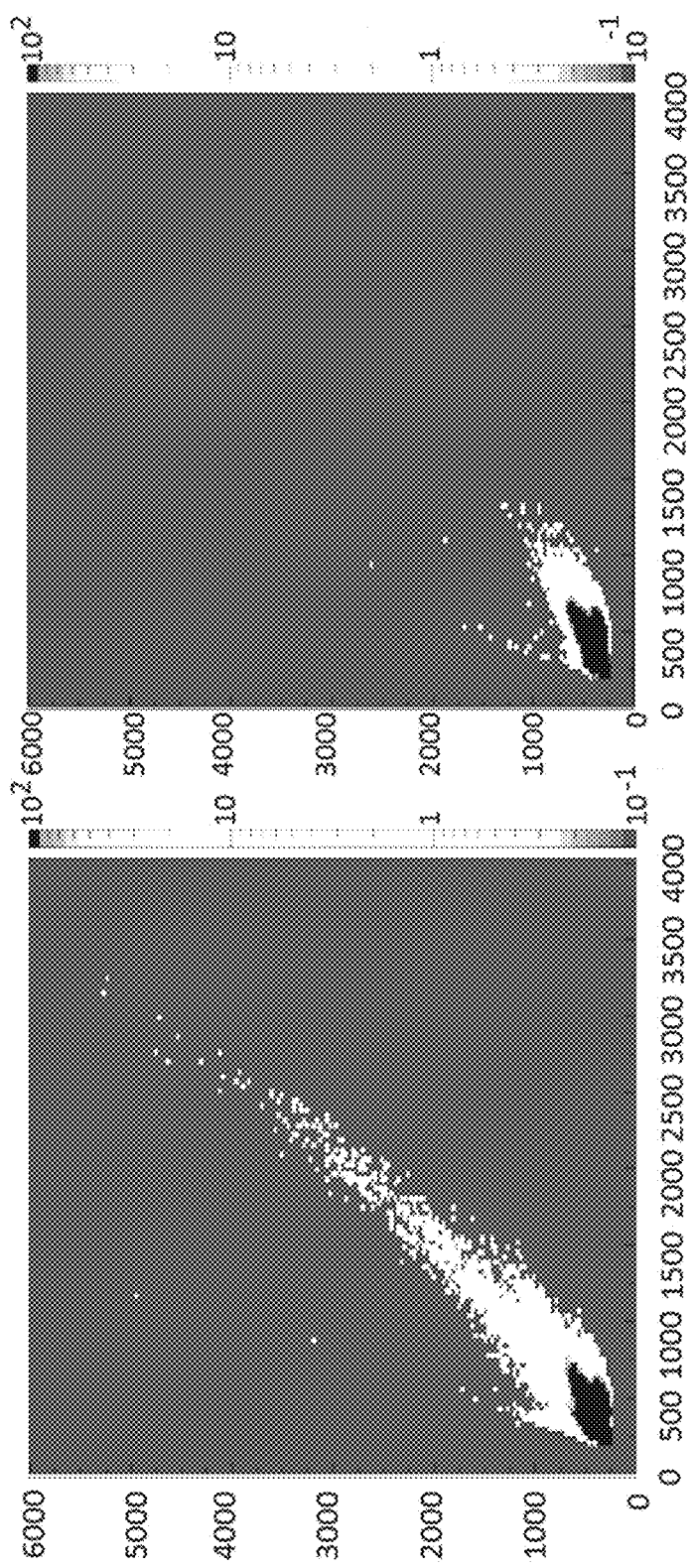

FIG. 9: Left-hand picture clearly shows two components corresponding to neutrons and gamma rays during irradiation by a $^{241}Am^9Be$ source. In the right-hand picture only the component corresponding to the gamma rays is seen when the compound is irradiated with $^{137}Cs$ and $^{22}Na$ sources.

Figure 10:
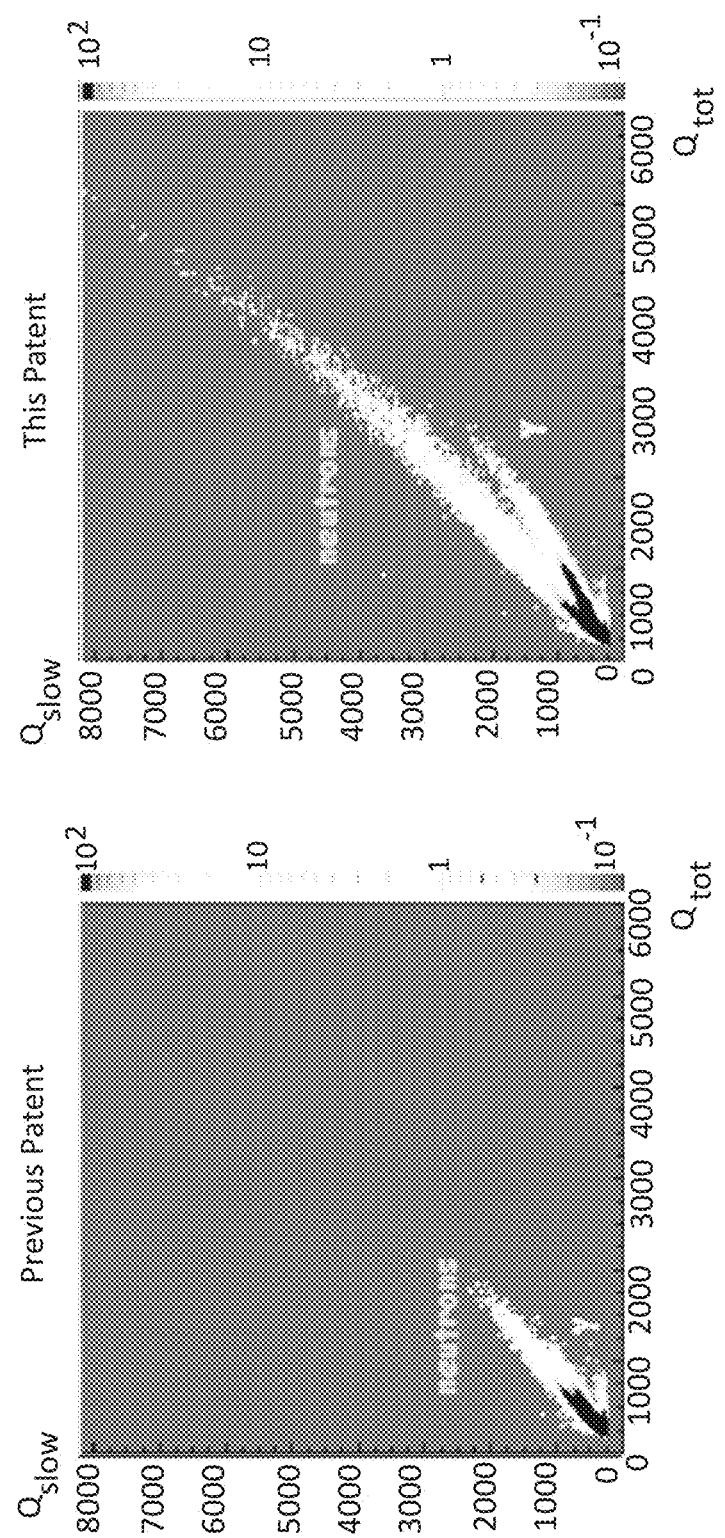

FIG. 10: Right-hand picture (referenced «this patent») corresponds to compound 60 and the left-hand picture to the oxazole imidazolium compound (patent application WO 2010/004228, referenced «Previous patent»). The graphs show a comparison between the two components corresponding to the neutrons and gamma rays when irradiated by a $^{241}Am^9Be$ source measured under the same conditions. In the right-hand picture (compound 60) the 2 components (neutron-gamma) are more intense and better separated than in the left-hand picture (referenced «Previous patent»— patent application WO 2010/004228). This evidences better discrimination and detection of neutron-gamma radiation.

Figure 11:
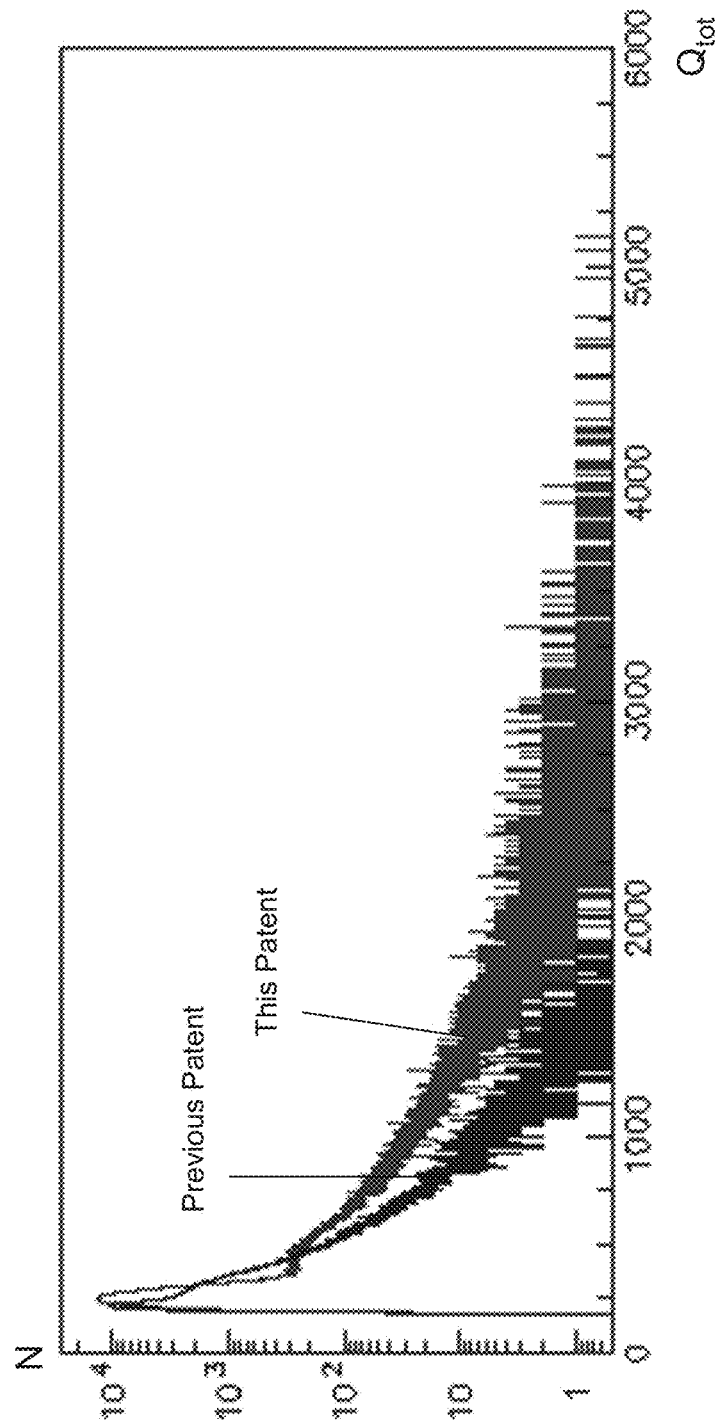

FIG. 11: The graph gives the projection of the total charge (Qtot) as compared between compound 60 and the oxazole imidazolium compound of the previous patent («Previous patent»—patent application WO 2010/004228). The total charge of compound 60 reaches much higher values than the compound of the previous patent application.

Figure 12:
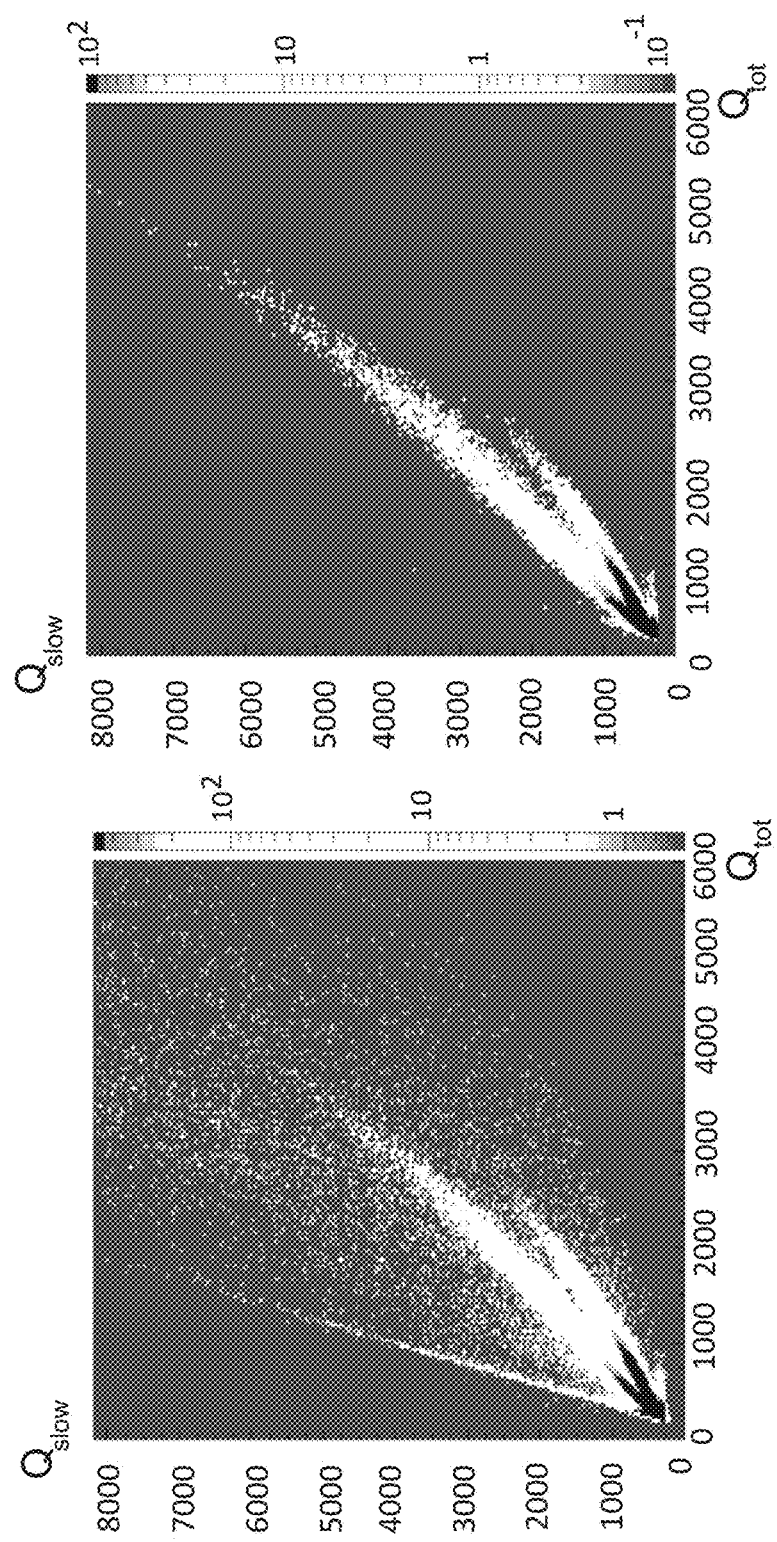

FIG. 12: The two images show the slow charge (Qslow) as a function of total charge (Qtot) of compound 60 irradiated with an AmBe source at an interval of about one year.

Figure 13:
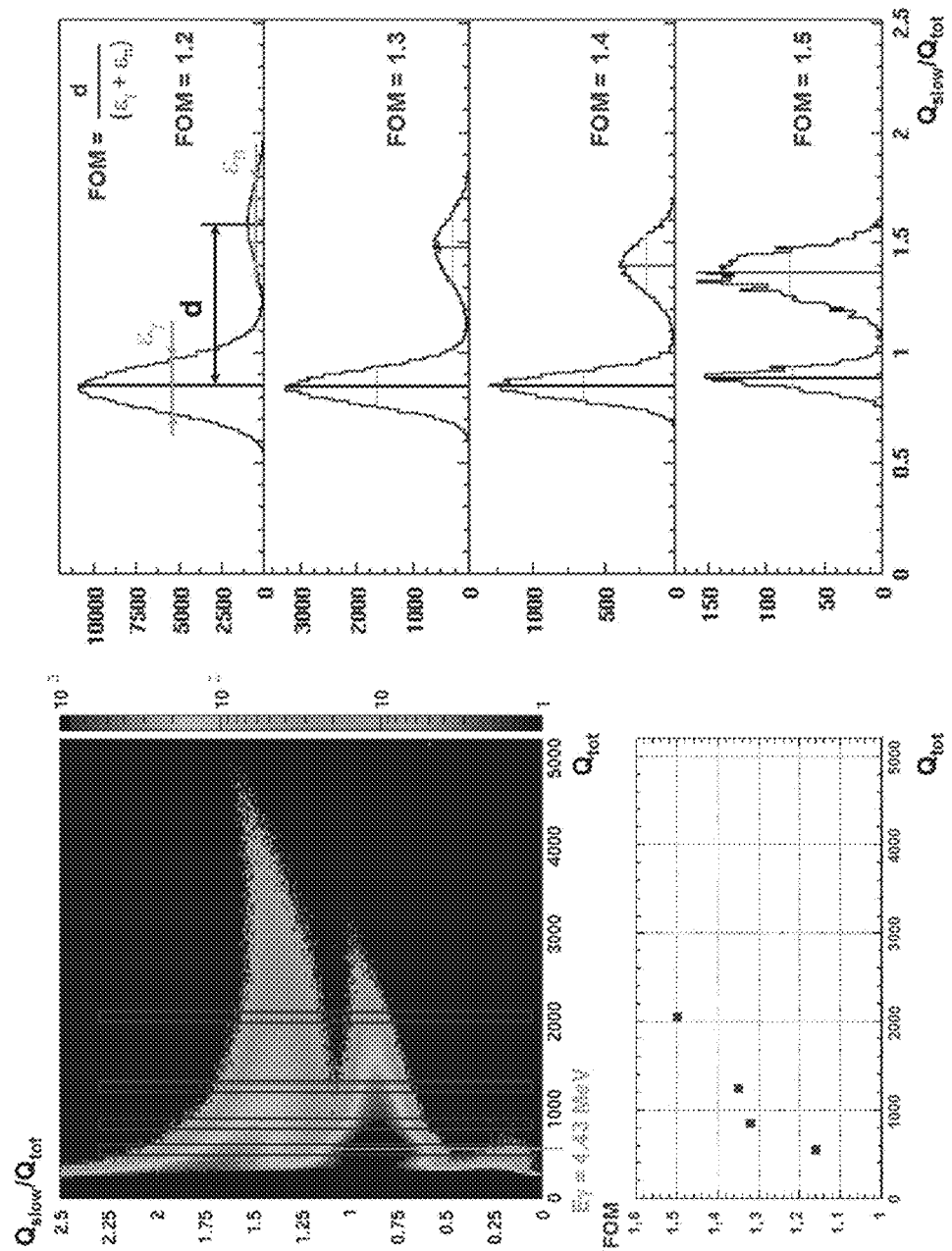

FIG. 13: The graphs show the discriminating power of compound 60 irradiated with an AmBe source. On the left side, the two-dimensional spectra show the ratio between slow charge and total charge (R=Qslow/Qtot) as a function of total charge (Qtot). Four sections indicated in the top left of the Figure were selected from the top left of FIG. 13 and the ratios are projected on the right side of FIG. 13. The bottom left of the Figure represents the trend in Figure of Merit (FOM) with increasing deposited energy. These values are comparable with the values obtained using a plastic scintillator developed by Zaitseva et al. (Zaitseva N., B. L. Rupert, I. Pawelczak, A. Glenn, H. P. Martinez, L. Carman, M. Faust, N. Cherepy, and S. Payne. 2012. Plastic Scintillators with Efficient Neutron/Gamma Pulse Shape Discrimination. Nuclear Instruments and Methods in Physics Research A, 668 88-93.)

EXAMPLES

The following examples illustrate the invention but are non-limiting. The starting products used were known products or prepared using known operating modes.

The percentages are expressed by weight unless otherwise indicated.

Synthesis of Luminescent Imidazolium Compounds: Applications to Neutron/Gamma Ray Discrimination Solvent-free Ullmann-type coupling was performed between a halide of a fluorophore group and an imidazole to prepare compounds of the invention having luminescent properties. These materials or scintillators emit light after absorbing ionising radiation. Scintillation is a fluorescence phenomenon whereby de-excitation leads to the emission of photons (most often in the visible range).

The following fluorophores were used: naphthalene, fluorene, 9-methylcarbazole and anthracene. The coupling reaction was carried out between imidazole and the bromine-containing fluorophore (1-bromonaphthalene, 2-bromofluorene, 3-bromo-9-methylcarbazole, 9-bromoanthracene) to obtain compounds 28 to 31 (Scheme 1 and Table 1). (see publication by M. B. Ponce, F. M. Cabrerizo, S. M. Bonesi, R. Erra-Balsells, Helvetica Chimica Acta, 2006, 89, 1123-1139. doi: 10.1002/hlca.200690110)

Scheme 1: Ullmann-type coupling reaction.

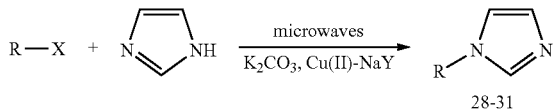

The coupling operations were performed using a microwave oven at 180° C. for 140 minutes in the presence of a base (potassium carbonate) and Cu(II)-NaY (catalyst, copper-impregnated zeolite).

These conditions allowed the rapid preparation of compounds 28 to 30 with satisfactory yields. It was also possible to obtain the imidazole derivative 31 rapidly but with low yield (30%). To recover the reaction product it is sufficient to re-dissolve in dichloromethane followed by filtration to remove the zeolite and potassium carbonate. The imidazole derivative thus obtained was purified by column chromatography.

TABLE 1

Yield of the synthesis of compounds 28 to 31. Reaction time: 140 minutes.

| Aryl used | Reaction temperature | Imidazole obtained | Yield |
|---|---|---|---|
| (1-bromonaphthalene structure) | 180° C. | (compound 28 structure) | 67% |
| (2-bromofluorene structure) | 180° C. | (compound 29 structure) | 62% |

TABLE 1-continued

Yield of the synthesis of compounds 28 to 31. Reaction time: 140 minutes.

| Aryl used | Reaction temperature | Imidazole obtained | Yield |
|---|---|---|---|
| (3-bromo-9-methylcarbazole) | 180° C. | 30 | 52% |
| (9-bromoanthracene) | 180° C. | 31 | 30% |

The imidazole derivatives 28 to 31 were then alkylated without solvent in the presence of a bromoalkane (1-bromooctane and 1-bromododecane) heating to 110° C. to obtain the corresponding imidazolium compounds (Scheme 2). Throughout this alkylation step, the reaction mixture has a tendency to cake. Two bromoalkanes were selected of different chain length (1-bromooctane and 1-bromododecane) to have materials with different melt temperatures (the anion and chain length both have an influence on melt temperatures). Finally the bromide anion was exchanged via anion metathesis in a biphasic medium (dichloromethane/water) using the lithium or potassium salt of the desired anion to obtain compounds 32 to 71 after purification (column chromatography).

Scheme 2 Synthesis of compounds 32 to 71.

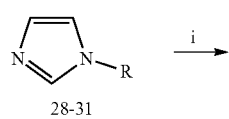

28-31

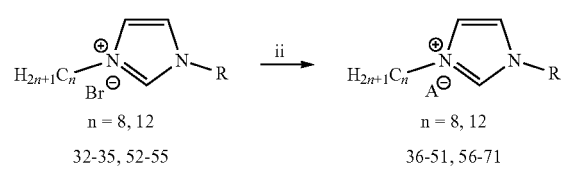

n = 8, 12
32-35, 52-55 n = 8, 12
36-51, 56-71

-continued i: BrC$_n$H$_{2n+1}$, 110° C. ii: corresponding salt, CH$_2$Cl$_2$/H$_2$O 28: R = naphthalene
29: R = fluorene
30: R = 9-methyl-carbazole
31: R = anthracene n = 8: 32-51
n = 12: 52-71

| | | | |
|---|---|---|---|
| 32, 52: Br | 33, 53: Br | 34, 54: Br | 35, 55: Br |
| 36, 56: BF$_4$ | 40, 60: BF$_4$ | 44, 64: BF$_4$ | 48, 68: BF$_4$ |
| 37, 57: PF$_6$ | 41, 61: PF$_6$ | 45, 65: PF$_6$ | 49, 69: PF$_6$ |
| 38, 58: I | 42, 62: I | 46, 66: I | 50, 70: I |
| 39, 59: N(SO$_2$CF$_3$)$_2$ | 43, 63: N(SO$_2$CF$_3$)$_2$ | 47, 67: N(SO$_2$CF$_3$)$_2$ | 51, 71: N(SO$_2$CF$_3$)$_2$ |

A$^-$ was selected from among Br$^-$, I$^-$, PF$_6^-$, (CF$_3$SO$_2$)$_2$N$^-$, as indicated above.

The imidazoliums having an eight-carbon chain are numbered 32 to 51 and those with a twelve-carbon chain are numbered 52 to 71. All the imidazoles (28 to 31) and imidazoliums (32 to 71) were characterized by NMR ($^1$H, $^{13}$C{$^1$H}), IR, UV/Visible spectroscopy and elementary analysis (C, H, N). POM observations and heat measurements (ATG, DSC) were performed on compounds 32 to 71. For reasons of clarity, the analysis results are grouped together and presented per type of fluorophore. Measurements of luminescence and discrimination are also given in different parts further to characterizations.

On the same principle compounds 72 and 73 were prepared, with n=6, R is a fluorene and A$^-$ is Br$^-$ and BF$_4^-$ respectively.

Example 1—Imidazolium Having One Naphthalene Unit (Compounds n° 32, 36 to 39, 52 and 56 to 59)

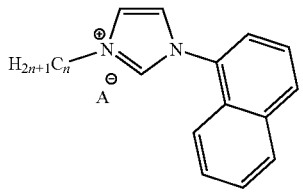

1.1 Characterizations

Tables 2 and 3 group together the synthesis yields, the N—CH—N hydrogen chemical shift of imidazolium, the characteristic absorption bands of the tetrafluoroborate, hexafluorophosphate and bis(trifluoromethylsulfonyl)amide anions, and the UV/Visible absorption bands for the imidazoliums containing a naphthalene unit. The imidazoliums 32 and 36 to 39 have an eight-carbon alkyl chain and the imidazoliums 52 and 56 to 59 have a twelve-carbon alkyl chain.

All the elementary analyses gave good results proving the purity of the synthesised compounds, with the exception of imidazolium 38.

TABLE 2

N-alkylation and anion metathesis of compounds 32, 36 to 39, 52 and 56 to 59.

| Compound | Yield | Shift ($\delta$, in ppm/anion) | IR band [a] |
|---|---|---|---|
| 32 | 82% | 10.69/Br$^-$ | |
| 36 | 92% | 9.11/BF$_4^-$ | 1053 cm$^{-1}$ |
| 37 | 86% | 8.78/PF$_6^-$ | 843 cm$^{-1}$ |
| 38 | 94% | 10.26/I$^-$ | |
| 39 | 87% | 9.01/(CF$_3$SO$_2$)$_2$N$^-$ | 1350 cm$^{-1}$ |
| | | | 1140 cm$^{-1}$ |
| 52 | 86% | 10.68/Br$^-$ | |
| 56 | 53% | 9.10/BF$_4^-$ | 1053 cm$^{-1}$ |
| 57 | 71% | 8.77/PF$_6^-$ | 820 cm$^{-1}$ |
| 58 | 76% | 10.43/I$^-$ | |
| 59 | 92% | 9.01/(CF$_3$SO$_2$)$_2$N$^-$ | 1350 cm$^{-1}$ |
| | | | 1196 cm$^{-1}$ |

[a] characteristic vibration band of anions BF$_4^-$, PF$_6^-$ and (CF$_3$SO$_2$)$_2$N$^-$.

TABLE 3

UV/Visible spectroscopy of imidazoliums 32, 36 to 39, 52 and 56 to 59.

| Compound | UV/Visible band [a] | | |
|---|---|---|---|
| 32 | | 283 nm (7200) | 228 nm (37300) |
| 36 | | 282 nm (7200) | 228 nm (33000) |
| 37 | | 282 nm (6900) | 228 nm (31300) |
| 38 | 364 nm (500) | 283 nm (8500) | 228 nm (41400) |
| 39 | | 283 nm (7600) | 228 nm (33000) |
| 52 | | 283 nm (7100) | 228 nm (35700) |
| 56 | | 283 nm (7100) | 229 nm (26700) |
| 57 | | 283 nm (7100) | 229 nm (27300) |
| 58 | | 283 nm (8100) | 230 nm (25300) |
| 59 | | 283 nm (7400) | 228 nm (33800) |

[a] UV/Visible absorption band: $\lambda_{max}$ ($\varepsilon$, L.mol$^{-1}$.cm$^{-1}$).

1.2 Thermal Analyses

Thermogravimetric analyses were carried out to determine the stability of the imidazoliums containing a naphthalene fluorophore (FIG. 3).

The imidazoliums (32, 36 to 39, 52 and 56 to 59) do not exhibit any mesomorphous property (POM observation), which was confirmed by DSC. The corresponding transition temperatures and enthalpies were determined by DSC. Except for compounds 32 and 52, the other imidazoliums are ionic liquids (melt temperature below 100° C.). Compounds 36, 39, 56 and 59 are liquid at ambient temperature, their melt temperatures were unable to be determined (amorphous solid/isotropic liquid transition). All the imidazoliums showed vitrification (except imidazolium 57): on cooling they did not crystallize but solidified to an amorphous state

TABLE 4

Enthalpies and transition temperatures of compounds 32, 36 to 39, 52 and 56 to 59.

| Compound | Heating | T (° C.) | H (kJ.mol$^{-1}$) | Cooling | T (° C.) | H (kJ.mol$^{-1}$) |
|---|---|---|---|---|---|---|
| 32, Br$^-$ | Cr—Iso | 138.0 | 25.88 | vitrification: Tg = 11.6 ° C. | | |
| 36, BF$_4^-$ | Liquide à TA | | | vitrification: Tg = −29.7 ° C. | | |
| 37, PF$_6^-$ | Cr—Iso | 79.4 | 23.17 | vitrification: Tg non-measurable | | |
| 38, I$^-$ | Cr—Iso | 91.7 | 16.96 | vitrification: Tg = −3.5 ° C. | | |
| 39, (CF$_3$SO$_2$)$_2$N$^-$ | Liquid at AT | | | vitrification: Tg = −52.4 ° C. | | |
| 52, Br$^-$ | Cr—Iso | 112.0 | 36.70 | vitrification: Tg = 8.2 ° C. | | |
| 56, BF$_4^-$ | Liquid at AT | | | vitrification: Tg = 4.1 ° C. | | |
| 57, PF$_6^-$ | Cr—Iso | 45.8 | 25.79 | Iso—Cr partial crystallisation | | |
| 58, I$^-$ | Cr—Iso | 63.3 | 24.85 | vitrification: Tg = −2.3 ° C. | | |
| 59, (CF$_3$SO$_2$)$_2$N$^-$ | Liquid at AT | | | vitrification: Tg = −54.7 ° C. | | |

Key: Cr: Crystal; Iso: isotropic liquid; T: temperature; H: enthalpy; Tg: glass transition; AT: ambient temperature.

The imidazoliums having a $C_{12}$ chain showed a lower melt temperature (by about 30° C.) than those with a $C_8$ chain. The lowest melt temperatures were obtained with chain lengths of twelve carbons.

Example 2—Imidazolium Having One Fluorene Unit (33, 40 to 43, 53 and 60 to 63)

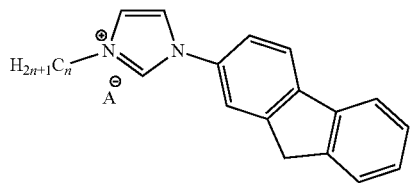

2.1 Characterizations

Tables 5 and 6 group together the synthesis yields, N—CH—N hydrogen chemical shift of imidazolium, the characteristic absorption bands of the tetrafluoroborate, hexafluorophosphate and bis(trifluoromethylsulfonyl)amide anions and the UV/Visible absorption bands of the imidazoliums containing one naphthalene unit. The imidazoliums 33 and 40 to 43 have an eight-carbon alkyl chain and the imidazoliums 53 and 60 to 63 have a twelve-carbon alkyl chain.

TABLE 5

N-alkylation and anion metathesis of compounds 33, 40 to 43, 53 and 60 to 63.

| Compound | Yield | Shift (δ, in ppm/anion) | IR band [a] |
|---|---|---|---|
| 33 | 88% | 11.29/Br⁻ | |
| 40 | 75% | 9.35/BF₄⁻ | 1030 cm⁻¹ |
| 41 | 85% | 9.04/PF₆⁻ | 820 cm⁻¹ |
| 42 | 89% | 10.80/I⁻ | |
| 43 | 89% | 9.24/(CF₃SO₂)₂N⁻ | 1343 cm⁻¹ 1130 cm⁻¹ |
| 53 | 86% | 11.29/Br⁻ | |
| 60 | 84% | 9.34/BF₄⁻ | 1067 cm⁻¹ |
| 61 | 68% | 8.98/PF₆⁻ | 828 cm⁻¹ |
| 62 | 62% | 10.82/I⁻ | |

TABLE 5-continued

N-alkylation and anion metathesis of compounds 33, 40 to 43, 53 and 60 to 63.

| Compound | Yield | Shift (δ, in ppm/anion) | IR band [a] |
|---|---|---|---|
| 63 | 89% | 9.26/(CF₃SO₂)₂N⁻ | 1349 cm⁻¹ 1121 cm⁻¹ |

[a] characteristic vibration band of anions $BF_4^-$, $PF_6^-$ et $(CF_3SO_2)_2N^-$.

TABLE 6

UV/Visible spectroscopy of imidazoliums 33, 40 to 43, 53 and 60 to 63.

| Compound | UV/Visible band [a] | | | |
|---|---|---|---|---|
| 33 | | 304 nm (19900) | 281 nm (22600) | 227 nm (12700) |
| 40 | | 304 nm (19300) | 281 nm (21900) | 227 nm (9300) |
| 41 | | 304 nm (19100) | 281 nm (21400) | 228 nm (11500) |
| 42 | 363 nm (1000) | 303 nm (21400) | 281 nm (23800) | 228 nm (21100) |
| 43 | | 304 nm (19900) | 281 nm (22600) | 227 nm (12700) |
| 53 | | 304 nm (19700) | 281 nm (22300) | 227 nm (15600) |
| 60 | | 304 nm (18800) | 280 nm (21500) | 229 nm (10200) |
| 61 | | 304 nm (18700) | 281 nm (20600) | 229 nm (10300) |
| 62 | | 304 nm (20400) | 282 nm (22500) | 230 nm (19300) |
| 63 | | 304 nm (19900) | 281 nm (21800) | 227 nm (13200) |

[a] UV/Visible absorption band: $\lambda_{max}$ ($\varepsilon$, L.mol⁻¹.cm⁻¹).

2.2 Thermal Analyses

Thermogravimetric measurements were conducted to determine the stability of the compounds having one fluorene unit (FIG. 4). The imidazolium bromides and iodides (33, 42, 53 and 62) have lesser thermal stability (about 240° C.) than the other compounds. The compounds with highest thermal stability were those having a bis(trifluoromethylsulfonyl)amide anion: 387° C. for imidazolium 43 and 358° C. for imidazolium 63.

The imidazoliums having one fluorene unit (33, 40 to 43, 53 and 60 to 63) do not exhibit any mesomorphous property (POM observation), confirmed by DSC. The corresponding transition temperatures and enthalpies were determined by DSC (Table 7 and FIG. 3). Most of the compounds have a single crystalline phase. Compounds 53 and 62 show two crystalline phases. Products 43 and 63 also exhibit two crystalline phases: the first ($Cr_1$) is solely visible on the first temperature rise, the second is only observed at following heatings.

TABLE 7

Enthalpies and transition temperatures of compounds 33, 40 to 43, 53 and 60 to 63.

| Compound | Heating | T (° C.) | H (kJ · mol⁻¹) | Cooling | T (° C.) | H (kJ · mol⁻¹) |
|---|---|---|---|---|---|---|
| 33, Br⁻ | Cr-Iso | 196.9 | 27.25 | Iso-Cr | 177.9 | 23.09 |
| 40, BF₄⁻ | Cr-Iso | 79.9 | 17.14 | vitrification Tg = 2.8° C. | | |
| 41, PF₆⁻ | Cr-Iso | 110.1 | 45.11 | Iso-Cr | 47.8 | 15.5 |
| 42, I⁻ | Cr-Iso | 160.2 | 18.35 | Iso-Cr | 115.1 | 17.17 |
| 43, (CF₃SO₂)₂N⁻ | Cr₁-Iso | 80.6 | 27.97 | Iso-Cr₂ | 42.6 | 14.17 |
| | Cr₂-Iso* | 49.3* | 12.52* | | | |
| 53, Br⁻ | Cr₁-Cr₂ | 61.8 | 18.17 | Iso-Cr₂ | 172.8 | 24.09 |
| | Cr₂-Iso | 200.6 | 27.01 | Cr₂-Cr₁ | 62.4 | 15.71 |
| 60, BF₄⁻ | Cr-Iso | 79.4 | 18.70 | vitrification: Tg = 2.0° C. | | |
| 61, PF₆⁻ | Cr-Iso | 111.7 | 30.54 | Iso-Cr | 97.6 | 34.16 |
| 62, I⁻ | Cr₁-Cr₂ | 69.8 | 10.47 | Iso-Cr₂ | 129.7 | 19.85 |
| | Cr₂-Iso | 163.2 | 19.75 | Cr₂-Cr₁ | 48.4 | 11.86 |

TABLE 7-continued

Enthalpies and transition temperatures of compounds 33, 40 to 43, 53 and 60 to 63.

| Compound | Heating | T (° C.) | H (kJ · mol$^{-1}$) | Cooling | T (° C.) | H (kJ · mol$^{-1}$) |
|---|---|---|---|---|---|---|
| 63, (CF$_3$SO$_2$)$_2$N$^-$ | Cr$_1$-Iso Cr$_2$-Iso* | 79.3 68.7* | 40.13 33.12* | Iso-Cr$_2$ | 45.1 | 11.77 |

Key:
Cr: Crystal;
Cr$_1$: crystal 1;
Cr$_2$: crystal2;
Iso: isotropic liquid;
T: temperature;
H: enthalpy;
Tg: glass transition.
*2nd temperature rise.

The melt temperatures (changeover to isotrope) were substantially the same for the imidazoliums having the eight-carbon alkyl chain (33, 40 to 43) and those having a twelve-carbon chain (53, 60 to 63).

The bromide of 1-(9H-fluoren-2-yl)-3-Hexyl-1H-imidazol-3-ium (72) was prepared:

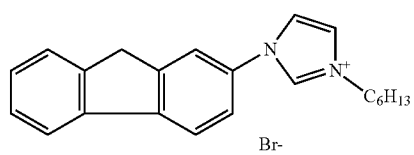

(72)

The tetrafluoroborate of 1-(9H-fluoren-2-yl)-3-Hexyl-1H-imidazol-3-ium (73) was prepared:

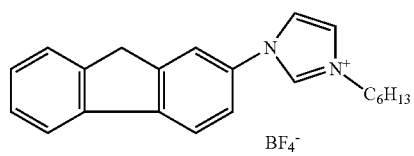

(73)

Compounds 72 and 73 were characterized by NMR spectroscopy and their melting point measured. These compounds exhibit radiation discrimination properties.

Example 3—Imidazoliums Having One Methylcarbazole Unit (34, 44 to 47, 54 and 64 to 67)

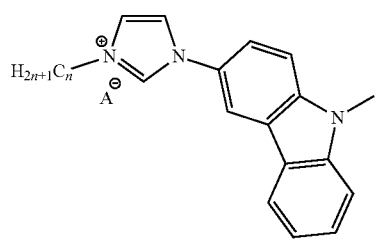

3.1 Characterizations

Tables 8 and 9 group together the synthesis yields, N—CH—N hydrogen chemical shift of imidazolium, the characteristic absorption bands of the tetrafluoroborate, hexafluorophosphate and bis(trifluoromethylsulfonyl)amide anions and the UV/Visible absorption bands for the imidazoliums having one methylcarbazole unit. Imidazoliums 34 and 44 to 47 have an eight-carbon alkyl chain and imidazoliums 54 and 64 to 67 have a twelve-carbon alkyl chain.

TABLE 8

N-alkylation and anion metathesis of compounds 34, 44 to 47, 54 and 64 to 67.

| Compound | Yield | Shift (δ, in ppm/anion) | IR band [a] |
|---|---|---|---|
| 34 | 85% | 11.12/Br$^-$ | |
| 44 | 85% | 9.30/BF$_4^-$ | 1024 cm$^{-1}$ |
| 45 | 95% | 8.93/PF$_6^-$ | 847 cm$^{-1}$ |
| 46 | 72% | 10.70/I$^-$ | |
| 47 | 94% | 9.15/(CF$_3$SO$_2$)$_2$N$^-$ | 1354 cm$^{-1}$ 1134 cm$^{-1}$ |
| 54 | 77% | 11.15/Br$^-$ | |
| 64 | 65% | 9.32/BF$_4^-$ | 1056 cm$^{-1}$ |
| 65 | 72% | 8.95/PF$_6^-$ | 816 cm$^{-1}$ |
| 66 | 56% | 10.77/I$^-$ | |
| 67 | 90% | 9.16/(CF$_3$SO$_2$)$_2$N$^-$ | 1350 cm$^{-1}$ 1197 cm$^{-1}$ |

[a] characteristic vibration band of anions BF$_4^-$, PF$_6^-$ et (CF$_3$SO$_2$)$_2$N$^-$.

Table 9 groups together the UV/Visible spectroscopy analyses of the imidazoliums having one methylcarbazole unit.

TABLE 9

UV/Visible spectroscopy of imidazoliums 34, 44 to 47, 54 and 64 to 67.

| Compound | UV/Visible band [a] | | | | |
|---|---|---|---|---|---|
| 34 | 350 nm (3100) | 335 nm (4100) | 279 nm (31700) | 239 nm (31300) | |
| 44 | 350 nm (2700) | 334 nm (3700) | 278 nm (29500) | 239 nm (29200) | |
| 45 | 350 nm (2700) | 335 nm (3800) | 280 nm (28700) | 239 nm (29100) | |
| 46 | 352 nm (3300) | 335 nm (4200) | 281 nm (31500) | 239 nm (41700) | |
| 47 | 350 nm (2800) | 335 nm (4000) | 280 nm (28700) | 239 nm (29500) | |
| 54 | 352 nm (3000) | 335 nm (4000) | 280 nm (31900) | 239 nm (31700) | 229 nm (28600) |
| 64 | 351 nm (2500) | 334 nm (3500) | 279 nm (29600) | 239 nm (29700) | |
| 65 | 350 nm (2200) | 334 nm (3200) | 280 nm (28600) | 238 nm (29300) | |
| 66 | 352 nm (3700) | 336 nm (4500) | 281 nm (32200) | 239 nm (42900) | |
| 67 | 351 nm (3000) | 337 nm (4000) | 281 nm (28100) | 238 nm (28900) | |

[a] UV/Visible absorption band: $\lambda_{max}$ (ε, L · mol$^{-1}$ · cm$^{-1}$).

3.2 Thermal Analyses

FIG. 6 groups together the thermogravimetric analyses of compounds 34, 44 to 47, 54 and 64 to 67. The imidazolium salts having a bromide anion (34 and 54) and iodide anion (46 and 66) show lower thermal stability (about 250° C.) than the other imidazoliums in the series. The most stable are those having a bis(trifluoromethylsulfonyl)amide anion (385° C. for compound 47 and 355° C. for compound 67).

The imidazoliums having one methylcarbazole unit (34, 44 to 47, 54 and 64 to 67) do not exhibit any mesomorphous property (POM observation), confirmed by DSC. The corresponding transition temperatures and enthalpies were determined by DSC (Table 10 and FIG. 4). Aside from compound 67 which is liquid at ambient temperature, the other compounds are solids. At a temperature lower than 100° C., the imidazoliums 44, 47, 64, 65, and 67 are ionic liquids. Some compounds have several crystalline phases in particular imidazolium iodide 66 which has three crystalline phases. It was not possible to determine the melt temperature of compound 45 since it proved to be amorphous at ambient temperature, which was confirmed by POM observation and DRX imaging (FIG. 5). The thermograms (DSC) of compound 45 suggest an amorphous solid/isotropic liquid transition (or the reverse on cooling) without passing through a crystallization step. Compound 67, liquid at ambient temperature, vitrifies on cooling; when it is heated it changes directly from an amorphous state to a liquid state which means that it is not possible to determine its melt temperature.

Overall, the melt temperatures differ little in relation to the length of the alkyl chain.

3.3 X-Ray Diffraction

POM observation revealed that compound 45 is amorphous at ambient temperature. The DRX image confirmed this amorphous state of imidazolium 45

Example 4—Imidazoliums Having One Anthracene Unit (35, 48 to 51, 55 and 68 to 71)

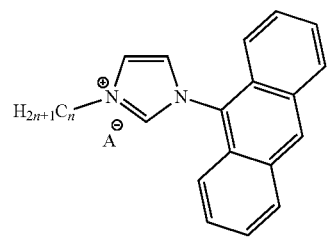

4.1 Characterizations

Tables 11 and 12 group together the synthesis yields, N—CH—N hydrogen chemical shift of imidazolium, the characteristic absorption bands of the tetrafluoroborate, hexafluorophosphate and bis(trifluoromethylsulfonyl)amide anions and the UV/Visible absorption bands for the imidazoliums containing one anthracene unit. Imizadoliums 35

TABLE 10

Enthalpies and transition temperatures of compounds 34, 44 to 47, 54 and 64 to 67.

| Compound | Heating | T (° C.) | H (kJ · mol$_{-1}$) | Cooling | T (° C.) | H (kJ · mol$^{-1}$) |
|---|---|---|---|---|---|---|
| 34, Br$^-$ | Cr-Iso | 171.6 | 11.95 | Iso-Cr | Partial crystallization | |
| 44, BF$_4^-$ | Cr-Iso | 75.1 | 19.65 | Vitrification: Tg = 12.6° C. | | |
| 45, PF$_6^-$ | amorphous at AT * | | | vitrification: Tg = 1.7° C. | | |
| 46, I$^-$ | Cr$_1$-Cr$_2$ | 111.3 | 0.87 | Partial crystallization | | |
| | Cr$_2$-Iso | 137.6 | 23.16 | | | |
| 47, (CF$_3$SO$_2$)$_2$N$^-$ | Cr$_1$-Cr2 | 38.7 | 3.59 | vitrification: Tg non-measurable | | |
| | Cr$_2$-Iso | 57.4 | 27.86 | | | |
| 54, Br$^-$ | Cr$_1$-Cr$_2$ | 111.9 | 24.28 | Iso-Cr$_2$ | 164.9 | 27.15 |
| | Cr$_2$-Iso | 186.1 | 28.39 | Cr$_2$-Cr$_1$ | 97.2 | 12.95 |
| 64, BF$_4^-$ | Cr$_1$-Cr$_2$ | 61.4 | 1.10 | vitrification: Tg = 14.0° C. | | |
| | Cr$_2$-Iso | 79.9 | 21.40 | | | |
| 65, PF$_6^-$ | Cr-Iso | 85.8 | 24.17 | vitrification: Tg = 16.1° C. | | |
| 66, I$^-$ | Cr$_1$-Cr$_2$ | 129.7 | 9.11 | Iso-Cr | 105.8 | 41.18 |
| | Cr$_2$-Cr$_3$ | 137.2 | 4.81 | | | |
| | Cr$_3$-Iso | 140.8 | 9.57 | | | |
| 67, (CF$_3$SO$_2$)$_2$N$^-$ | liquid at AT | | | vitrification: Tg = −26.1° C. | | |

Key:
Cr: Crystal;
Cr$_1$: crystal 1;
Cr$_2$: crystal 2;
Cr3: crystal 3;
Iso: isotropic liquid;
T: temperature;
H: enthalpy;
Tg: glass transition;
AT: ambient temperature.
* determined by POM and DRX of the mesophase.

and 48 to 51 have an eight-carbon alkyl chain and imidazoliums 55 and 68 to 71 have a twelve-carbon alkyl chain. Elementary analysis of compound 51 showed the presence of traces of imidazolium bromide (35) which were not detected by thin layer chromatography or by NMR ($^1$H, $^{13}$C{$^1$H}).

TABLE 1

N-alkylation and anion metathesis of compounds 35, 48 to 51, 55 and 68 to 71.

| Compound | Yield | Shift (δ, in ppm/anion) | IR band $^a$ |
|---|---|---|---|
| 35 | 93% | 10.41/Br$^-$ | |
| 48 | 75% | 9.02/BF$_4^-$ | 1071 cm$^{-1}$ |
| 49 | 63% | 8.69/PF$_6^-$ | 878 cm$^{-1}$ |
| 50 | 71% | 10.09/I$^-$ | |
| 51 | 65% | 8.90/(CF$_3$SO$_2$)$_2$N$^-$ | 1354 cm$^{-1}$ |
| | | | 1134 cm$^{-1}$ |
| 55 | 95% | 10.43/Br$^-$ | |
| 68 | 88% | 9.02/BF$_4^-$ | 1140 cm$^{-1}$ |
| 69 | 91% | 8.69/PF$_6^-$ | 845 cm$^{-1}$ |
| 70 | 91% | 10.05/I$^-$ | |
| 71 | 91% | 8.90/(CF$_3$SO$_2$)$_2$N$^-$ | 1350 cm$^{-1}$ |
| | | | 1138 cm$^{-1}$ |

$^a$ characteristic vibration band of anions BF$_4^-$, PF$_6^-$ et (CF$_3$SO$_2$)$_2$N$^-$.

TABLE 12

UV/Visible spectroscopy of imidazoliums 35, 48 to 51, 55 and 68 to 71.

| Compound | UV/Visible band $^a$ | | | | |
|---|---|---|---|---|---|
| 35 | 387 nm (6000) | 370 nm (6900) | 354 nm (5300) | | 254 nm (149700) |
| 48 | 387 nm (6600) | 370 nm (8200) | 353 nm (6200) | 305 nm (1500) | 254 nm (163500) |
| 49 | 387 nm (5300) | 369 nm (7000) | 352 nm (5400) | | 254 nm (163600) |
| 50 | 387 nm (6100) | 370 nm (7700) | 353 nm (6000) | 322 nm (2100) | 254 nm (159100) |
| 51 | 387 nm (5900) | 370 nm (7700) | 351 nm (5900) | | 254 nm (165600) |
| 55 | 387 nm (6500) | 369 nm (7500) | 352 nm (6000) | | 255 nm (161300) |
| 68 | 387 nm (5400) | 371 nm (6700) | 351 nm (5300) | 308 nm (8500) | 254 nm (185400) |
| 69 | 387 nm (5500) | 370 nm (6800) | 354 nm (5100) | | 254 nm (160900) |
| 70 | 387 nm (6700) | 369 nm (8300) | 354 nm (6700) | 289 nm (3500) | 254 nm (165900) |
| 71 | 387 nm (4900) | 370 nm (6000) | 354 nm (4900) | | 254 nm (156800) |

$^a$ UV/Visible absorption band: $\lambda_{max}$ (ε, L · mol$^{-1}$ · cm$^{-1}$).

4.2 Thermal Analyses

Thermogravimetric analyses were performed and showed that the imidazolium halides (35, 50, 55 and 70) have the least thermal stability (about 220° C.) in the series (FIG. 6). The most stable (about 310° C.) are those having a bis (trifluoromethylsulfonyl)amide anion (51 and 71).

Table 1 and FIG. 10 group together the corresponding transition temperatures and enthalpies. Solely imidazolium 71 is liquid at ambient temperature: it was not possible to determine its melt temperature by DSC (amorphous solid/isotropic liquid transition). All the others are solid at ambient temperatures and have a melt temperature lying between 74 and 134° C. according to anion.

TABLE 13

Enthalpies and transition temperatures of compounds 35, 48 to 51, 55 and 68 to 71.

| Compound | Heating | T (° C.) | H (kJ · mol$^{-1}$) | Cooling | T (° C.) | H (kJ · mol$^{-1}$) |
|---|---|---|---|---|---|---|
| 35, Br$^-$ | Cr-Iso | 92.2 | 24.56 | vitrification: Tg non-measurable | | |
| 48, BF$_4^-$ | Cr-Iso | 100.8 | 21.39 | vitrification: Tg = 7.1° C. | | |
| 49, PF$_6^-$ | Cr-Iso | 114.9 | 23.72 | vitrification: Tg = 10.9° C. | | |
| 50, I$^-$ | Cr$_2$-Iso | 74.3 | 21.30 | vitrification: Tg non-measurable | | |
| 51, (CF$_3$SO$_2$)$_2$N$^-$ | Cr$_1$-Cr$_2$ | 71.7 | 1.55 | vitrification: Tg = 14.7° C. | | |
| | Cr-Iso | 108.6 | 20.46 | | | |
| 55, Br$^-$ | Cr$_1$-Cr$_2$ | 109.3 | 22.52 | Iso-Cr$_1$ | 75.3 | 12.54 |
| | Cr$_2$-Iso | 114.3 | 9.45 | | | |
| 68, BF$_4^-$ | Cr$_1$-Cr$_2$ | 77.8 | 22.97 | vitrification: Tg = 14.0° C. | | |
| | Cr$_2$-Iso | 100.7 | 2.85 | | | |
| 69, PF$_6^-$ | Cr-Iso | 99.1 | 13.95 | vitrification: Tg = 6.0° C. | | |
| 70, I$^-$ | Cr$_1$-Cr$_2$ | 79.4 | 8.62 | vitrification: Tg = 22.9° C. | | |
| | Cr$_2$-Iso | 133.6 | 12.51 | | | |
| 71, (CF$_3$SO$_2$)$_2$N$^-$ | liquid at AT | | | vitrification: Tg = −35.3° C. | | |

Key:
Cr: Crystal; Cr$_1$: crystal 1; Cr$_2$: crystal 2; Iso: isotropic liquid; T: temperature; H: enthalpy; Tg: glass transition; AT ambient temperature.

The presence of an eight-carbon chain does not allow a substantial drop in melt temperature of compounds (35, 48 to 51). In addition, the only liquid compound at ambient temperature was an imidazolium having a twelve-carbon alkyl chain.

Conclusions on Examples 1 to 4—Imidazolium/Fluorophores

The imidazoliums containing a fluorophore (naphthalene, fluorene, methylcarbazole and anthracene) were synthesized and overall gave good yields. All these compounds were characterized using usual methods. Thermal analyses showed that all the imidazoliums have good thermal stability. UV/Visible spectroscopy allowed determination of the absorption bands of the different imidazolium salts so that luminescence measurements could be carried out.

Example 5—Luminescence and Neutron and Gamma Ray Discrimination 5.1 Characterization To characterize luminescence properties, the excitation and emission spectra of compounds 52, 58 (imidazolium/naphthalene), 53 (imidazolium/fluorene), 54 (imidazolium/methylcarbazole) and 68 (imidazolium/anthracene) were recorded (Table 14 and FIG. 7).

TABLE 14

UV/Visible spectroscopy and luminescence analyses 52, 53, 54 and 58.

| Compnd | UV/Visible | | | | | Luminescence Excitation (nm) | Emission (nm) |
|---|---|---|---|---|---|---|---|
| 52 | $\lambda_{max}$ (nm) | 228 | 283 | | | 289 | 384 |
| | $\varepsilon$ (L · mol$^{-1}$ · cm$^{-1}$) | 35700 | 7100 | | | | |
| 58 | $\lambda_{max}$ (nm) | 230 | 283 | | | 289 | 384 |
| | $\varepsilon$ (L · mol$^{-1}$ · cm$^{-1}$) | 25300 | 8100 | | | | |
| 53 | $\lambda_{max}$ (nm) | 227 | 281 | 304 | | 306 | 401 |
| | $\varepsilon$ (L · mol$^{-1}$ · cm$^{-1}$) | 15600 | 2230 | 1970 | | | |
| 54 | $\lambda_{max}$ (nm) | 229 | 239 | 280 | 335 352 | 288 | 429 |
| | $\varepsilon$ (L · mol$^{-1}$ · cm$^{-1}$) | 28600 | 3170 | 3190 | 400 300 | | |
| 68 | $\lambda_{max}$ (nm) | 254 | 308 | 351 | 371 387 | 258 | 397, 419, 444 |
| | $\varepsilon$ (L · mol$^{-1}$ · cm$^{-1}$) | 185400 | 8500 | 5300 | 670 540 | | |

Luminescence spectra were obtained in dichloromethane and at low concentration: $2.45 \cdot 10^{-6}$ (52), $2.50 \cdot 10^{-6}$ (58), $2.52 \cdot 10^{-7}$ (53), $2.52 \cdot 10^{-7}$ (54) and $2.88 \cdot 10^{-7}$ mol·L$^{-1}$ (68). All these imidazoliums absorb in the ultraviolet between 258 (68) and 288 nm (54) and re-emit in the violet (visible) between 384 (52 and 58) and 444 nm (68). Compound 68 shows three emission bands when irradiated at 258 nm whereas the other imidazoliums only have one emission band when irradiated.

The compounds containing a fluorene, easy to prepare in large quantity (yield of Ullmann-type coupling higher than 50%), are good candidates to prepare a scintillator. The materials containing a tetrafluoroborate anion give better discrimination results than the other anions. A sample of about ten grams of compound 60 was prepared and placed in a Petri dish. To form this material, the compound was melted therein and left to crystallize at ambient temperature. The imidazolium was used pure without the addition of other solid or liquid compounds, or of a solvent. The material maintained its luminescence properties in the liquid and solid state (FIG. 8).

Preliminary results showed that imidazolium 60 allows the detection and discrimination between neutron and gamma rays (FIG. 9). This discriminating property was evidenced by irradiating the material with a $^{241}$Am$^9$Be source which emits neutrons and gamma rays, and with sources solely emitting gamma rays ($^{137}$Cs, $^{22}$Na, $^{60}$Co). Analysis of the shape of the signal was carried out and the two components corresponding to the neutrons and gamma rays could be very clearly distinguished.

5.2 Conclusion

Imidazoliums were prepared containing a fluorophore (naphthalene, fluorene, methylcarbazole, anthracene) to obtain materials having properties of luminescence and neutron/gamma ray discrimination. All the compounds were characterized and their luminescence measured; however none of these materials showed liquid crystal properties. Preliminary detection measurements performed on the imidazolium containing a fluorene unit evidenced the discrimination properties thereof between gamma rays and neutrons.

The couplings of homo- and heterocyclic aromatics having luminescence properties were examined. Fluorophores (naphthalene, fluorene, methylcarbazole, anthracene) were coupled with the imidazoliums and allowed the preparation of compounds having applications to the detection and discrimination of ionising radiation. Preliminary detection measurements performed on these compounds containing a fluorene evidenced their discriminating properties between neutron/gamma rays. For discrimination, the transparency of the scintillator is an important parameter since it is based on measurement of the luminescence of the materials: the more transparent the material the better its detection response. This parameter remains to be adjusted for these types of material. However, crystal engineering (mirror oven . . . ) or zone fusion techniques should allow the transparency of these compounds to be obtained.

Example 6—Transparency Properties

The transparency of the samples was evaluated by examining the transmission of direct light which represents the minimum performance level of a material irrespective of the characteristics of the detector in which it is to be integrated, in particular the photomultiplier's solid collection angle. Measurement was performed using an optical microscope and digital camera and by varying the exposure time between a first configuration in which the sample (cover glass with product, recipient with crystallizate) was inserted in the optical pathway, and a second configuration without product (cover glass of same thickness or recipient with the same amount of water). The time ratio for one same count was considered to be similar to transmission.

The results were the following:

Compound of application WO 2010/004228 (oxazole, imidazolium, PF6): 0.07% Compound 60: 0.16%

Compound 60 is about 2.3 (=16/7) times more transparent than the oxazole imidazolium compound, PF6 (patent WO 2010/004228) under the same preparation conditions (heating and crystallization).

Example 7—Experimental Section

All the reagents and solvents were commercially available and used without additional purification unless otherwise indicated.

Syntheses in microwave oven were performed using a Monowave 300 (Anton Paar) microwave oven for synthesis.

Separations by chromatography were conducted using Merck Si 60 silica (40-63 mm) or with standardised Merck 90 aluminium oxide. For flash chromatography CombiFlash Companion apparatus was used (Teledyne ISCO, Serlabo Technologies). Thin layer chromatography was performed using Merck Si 60 F254 silica-coated aluminium foil.

The spectra of proton and carbon nuclear magnetic resonance were recorded using a Brucker Avance 300 spectrometer. Chemical shifts (δ) are expressed in ppm and the abbreviations s, s broad, d, dd, t, t broad, qua, qui, m and broad m are used to designate multiplicity of signals respectively: singlet, broad singlet, doublet, doublet of doublets, triplet, broad triplet, quadruplet, quintuplet, multiplet and broad multiplet. The coupling constants J are expressed in Hz. Unless otherwise indicated the spectra were recorded at 300 MHz for the proton and at 75 MHz for carbon in deuterated chloroform at 25° C.

Infrared spectra were recorded on an IR Digital FTS 3000 spectrophotometer (KBr pellet). The frequencies ($v_{max}$) are expressed in $cm^{-1}$.

UV/Visible spectra were recorded on a U-3000 spectrophotometer and the solvent used, unless otherwise indicated, was dichloromethane. Wavelengths ($\lambda_{max}$) are expressed in nm and the molar absorption coefficients (ε) in $L \cdot mol^{-1} \cdot cm^{-1}$. Luminescence spectra were recorded on a spectrophotometer made by Photon Technology International (Motor Driver 5020, Lamp Power Supply 220B, Photomultiplier Detection System 814, Felix software). Elementary analyses were conducted by the analytical department at Institut Charles Sadron and by the analytical department of the University of Strasbourg (Strasbourg, France). Phase and metaphase observations were carried out using a Leitz Orthoplan polarised light microscope equipped with Mettler FP82 hot plate driven by a FP80 control unit. Thermogravimetric analyses were performed on SDT Q600 equipment ($10° C.min^{-1}$). The corresponding transition temperatures and enthalpies were measured by differential scanning calorimetry on DSC Q1000 apparatus (TA Instruments) ($5° C.min^{-1}$, $2° C.min^{-1}$). X-ray diffraction measurements were performed under transmission on powder samples contained in Lindeman capillaries or in sealed cells using a $CuK_{\alpha 1}$ beam delivered by a sealed tube generator equipped with focusing quartz blade monochromator and Inel CPS120 curved detector, temperature being controlled with accuracy to within 0.03° C.

7.1 Preparation of Compounds 28 to 71.
Procedures for the Synthesis of Compounds 28 to 71.
General Procedure for Ullmann-Type Coupling (Forming of C—N Bond).

A mixture of aryl halide, imidazole, potassium carbonate and Cu(II)-NaY was heated in a microwave oven at 180° C. for 140 minutes in a sealed tube. The reaction product was re-dissolved in dichloromethane and filtered to remove the catalyst. The filtrate was purified by flash chromatography (silica gel, ethyl acetate/cyclohexane: 30:70) or by column chromatography (silica gel, ethyl acetate) to obtain the corresponding pure product.

1-(naphtalen-1-yl)-2H-imidazole (28)

The general procedure with 1-bromo-naphthalene (2.534 g; 12.24 mmol), imidazole (1.088 g; 15.98 mmol), potassium carbonate (1.902 g; 13.76 mmol) and Cu(II)-NaY (1.227 g) allowed 28 to be obtained with a yield of 67% (1.584 g; 8.16 mmol). $^1H$ NMR (300 MHz, $CDCl_3$): δ=7.31 (s, 1H, CH naphthalene or imidazole); 7.34 (s, 1H, CH naphthalene or imidazole); 7.49 (d, 1H, J=6.57 Hz, CH naphthalene or imidazole) 7.55-7.64 (m, 4H, CH naphthalene or imidazole); 7.92 (s, 1H, N—CH—N), 7.99 (t, 2H, J=7.44 Hz, CH naphthalene or imidazole). $^{13}C$ NMR (75 MHz, $CDCl_3$): δ=121.61; 122.27; 123.59; 125.13; 126.91; 127.54; 128.25; 129.18 (CH naphthalene or imidazole); 129.49 (quaternary C); 129.53 (CH naphthalene or imidazole); 134.06; 134.16 (quaternary C); 138.34 (CH naphthalene or imidazole). $v_{max}/cm^{-1}$ 3056 (aromatic C—H); 1595 (aromatic C=C; 1279 (C—N). UV/Vis ($CH_2Cl_2$): $\lambda_{max}$ (εL $mol^{-1}$ $cm^{-1}$)=282 nm (7600); 231 nm (15900). Elementary analysis for $C_{13}H_{10}N_{2-0.04}H_2O$; Calculated: C, 80.09; H, 5.21; N, 14.37%. Found: C, 80.09; H, 5.33; N, 14.32%.

1-(9H-fluoren-2-yl)-2H-imidazole (29)

The general procedure with 2-bromo-9H-fluorene (1.972 g; 8.05 mmol), imidazole (0.951 g; 13.97 mmol), potassium carbonate (1.496 g; 10.82 mmol) and Cu(II)-NaY (0.924 g) allowed 29 to be obtained with a yield of 62% (1.151 g; 4.96 mmol). $^1H$ NMR (300 MHz, $CDCl_3$): δ=3.99 (s, 2H, $CH_2$ fluorene); 7.24 (s, 1H, CH fluorene or imidazole); 7.35-7.45 (m, 4H, CH fluorene or imidazole); 7.58-7.60 (m, 2H, CH fluorene or imidazole); 7.91-7.92 (m, 3H, CH fluorene or imidazole). $^{13}C$ NMR (75 MHz, $CDCl_3$): δ=36.87 ($CH_2$ fluorene); 118.31; 119.95; 120.33; 120.67; 125.01; 126.97; 127.12; 130.28 (CH fluorene or imidazole); 135.71 (quaternary C); 135.93 (fluorene or imidazole); 140.38; 141.07; 143.10; 144.83 (quaternary C). $v_{max}/cm^{-1}$ 3051 (aromatic C—H); 2917 (aliphatic C—H); 1587 (aromatic C=C); 1259 (C—N). UV/Vis ($CH_2Cl_2$): $\lambda_{max}$ (ε $L \cdot mol^{-1} \cdot cm^{-1}$)=278 nm (24400); 218 nm (9500). Elementary analysis for $C_{16}H_{12}N_{2-0.35}H_2O$; Calculated: C, 82.35; H, 5.23; N, 12.00%. Found: C, 82.36; H, 5.57; N, 11.57%.

1-(9-methyl-carbazol-3-yl)-2H-imidazole (30)

The general procedure with 3-bromo-9-methyl-carbazole (0.647 g; 2.49 mmol), imidazole (0.349 g; 5.13 mmol), potassium carbonate (0.691 g; 5.00 mmol) and Cu(II)-NaY (0.324 g) allowed 30 to be obtained with a yield of 52% (0.321 g; 1.30 mmol). $^1H$ NMR (300 MHz, $CDCl_3$): δ=3.92 (s, 3H, $CH_3$ carbazole); 7.25 (s, 1H, CH carbazole or imidazole); 7.30-7.37 (m, 2H, CH carbazole or imidazole); 7.45-7.59 (m, 4H, CH carbazole or imidazole); 7.91 (s, 1H, N—CH—N); 8.08-8.13 (m, 2H, CH carbazole or imidazole). $^{13}C$ NMR (75 MHz, $CDCl_3$): δ=29.12 ($CH_3$ carbazole); 108.79; 109.03; 113.90; 119.33; 120.07; 120.42 (CH carbazole or imidazole); 122.06; 123.17 (quaternary C); 126.57 (CH carbazole or imidazole); 129.55 (quaternary C); 129.90; 136.31 (CH carbazole or imidazole); 139.81; 141.64 (quaternary C). $v_{max}/cm^{-1}$ 3113 (aromatic C—H); 2928 (aliphatic C—H); 1503 (aromatic C=C); 1228 (C—N). UV/Vis ($CH_2Cl_2$): $\lambda_{max}$ (ε $L \cdot mol^{-1} \cdot cm^{-1}$)=352 nm (3200); 340 nm (3300); 299 nm (13300); 270 nm (31600); 242 nm (38800). Elementary analysis for $C_{16}H_{13}N_{3-0.12}H_2O$; Calculated: C, 77.04; H, 5.35; N, 16.84%. Found: C, 77.04; H, 5.50; N, 16.54%.

1-(anthracen-9-yl)-2H-imidazole (31)

The general procedure with 9-bromoanthracene (0.506 g; 1.97 mmol), imidazole (0.328 g; 4.81 mmol), potassium carbonate (0.482 g; 3.49 mmol) and Cu(II)-NaY (0.286 g) allowed 31 to be obtained with a yield of 30% (0.143 g; 0.59 mmol). $^1$H NMR (300 MHz, CDCl$_3$): δ=7.30 (s, 1H, CH anthracene or imidazole); 7.44-7.57 (m, 7H, CH anthracene or imidazole); 7.83 (s, 1H, CH anthracene or imidazole); 8.10 and 8.12 (dd, 2H, J=1.92 and 6.84 Hz, CH anthracene or imidazole); 8.63 (s, 1H, N—CH—N). $^{13}$C NMR (75 MHz, CDCl$_3$): δ=122.29; 122.61; 125.79; 127.47; 128.25; 128.36 (CH anthracene or imidazole); 128.67 (quaternary C); 129.61 (CH anthracene or imidazole); 131.12 (quaternary C); 139.50 (CH anthracene or imidazole). $v_{max}$/cm$^{-1}$ 3053 (aromatic C—H); 2923 and 2851 (aliphatic C—H); 1487 (aromatic C=C). UV/Vis (CH$_2$Cl$_2$): $\lambda_{max}$ (εL·mol$^{-1}$.cm$^{-1}$)=385 nm (8300); 366 nm (8300); 348 nm (5300); 332 nm (2500); 255 nm (168100). Elementary analysis for $C_{17}H_{12}N_{2-0.06}H_2O$; Calculated: C, 83.21; H, 4.98; N, 11.42%. Found: C, 83.22; H, 5.12; N, 11.24%.

Imidazoliums 32 to 51 with $C_8$ Carbon Chain

General Procedure for the Synthesis of Imidazoliums (N-Alkylation).

A mixture of imidazole derivative and 1-bromooctane was heated in a microwave oven for 140 minutes at 110° C. in a sealed tube. The corresponding imidazolium salt was purified by flash chromatography (silica gel, dichloromethane to dichloromethane/methanol: 95:5) or column chromatography (silica gel, dichloromethane/methanol: 95:5).

1-(napthalen-1-yl)-3-octyl-2H-imidazol-3-ium Bromide (32)

The general procedure with 28 (2.676 g; 13.78 mmol) and 1-bromooctane (11.34 g; 58.70 mmol) allowed 32 to be obtained with a yield of 82% (4.385 g; 11.32 mmol). $^1$H NMR (300 MHz, CDCl$_3$): δ=0.89 (t, 3H, J=6.60 Hz, CH$_3$ aliphatic chain); 1.30-1.46 (broad m, 10H, CH$_2$ aliphatic chain and N—CH$_2$—CH$_2$—CH$_2$); 2.07 (qui, 2H, J=7.41 Hz, N—CH$_2$—CH$_2$); 4.79 (t, 2H, J=7.68 Hz, N—CH$_2$); 7.49-7.67 (m, 6H, CH naphthalene or imidazolium); 7.92 and 7.94 (dd, 1H, J=1.08 and 7.41 Hz, CH naphthalene or imidazolium); 8.01-8.11 (m, 2H, CH naphthalene or imidazolium); 10.69 (s, 1H, N—CH—N). $^{13}$C NMR (75 MHz, CDCl$_3$): δ=13.72 (C—CH$_3$ aliphatic chain); 22.23; 25.93; 28.67; 28.71; 30.12; 31.33 (CH$_2$ aliphatic chain); 50.16 (N—CH$_2$); 120.34; 123.17; 123.87; 124.34; 124.94; 127.27 (CH naphthalene or imidazolium); 127.36 (quaternary C); 128.43; 128.50 (CH naphthalene or imidazolium); 130.32 (quaternary C); 131.19 (CH naphthalene or imidazolium); 133.79 (quaternary C); 137.27 (CH naphthalene or imidazolium). $v_{max}$/cm$^{-1}$ 3059 (aromatic C—H); 2924 and 2851 (aliphatic C—H); 1545 (aromatic C=C). UV/Vis (CH$_2$Cl$_2$): $\lambda_{max}$ (εL·mol$^{-1}$.cm$^{-1}$)=283 nm (7200); 228 nm (37300). Elementary analysis for $C_{21}H_{27}BrN_2$; Calculated: C, 65.11; H, 7.03; N, 7.23%. Found: C, 64.95; H, 7.01; N, 7.33%.

1-(9H-fluoren-2-yl)-3-octyl-2H-imidazol-3-ium Bromide (33)

The general procedure with 29 (2.896 g; 12.47 mmol) and 1-bromooctane (25.09 g; 129.93 mmol) allowed 33 to be obtained with a yield of 88% (4.642 g; 10.91 mmol). $^1$H NMR (300 MHz, CDCl$_3$): δ=0.88 (t, 3H, J=6.30 Hz, CH$_3$ aliphatic chain); 1.27-1.44 (broad m, 10H, CH$_2$ aliphatic chain and N—CH$_2$—CH$_2$—CH$_2$); 2.02 (qui, 2H, J=7.68 Hz, N—CH$_2$—CH$_2$); 4.04 (s, 2H, CH$_2$ fluorene); 4.64 (t, 2H, J=7.41 Hz, N—CH$_2$) 7.37-7.46 (m, 3H, CH fluorene or imidazolium); 7.59-7.61 (m, 2H, CH fluorene or imidazolium); 7.73 and 7.75 (dd, 1H, J=2.19 et 8.22 Hz, CH fluorene or imidazolium); 7.83 (d, 1H, J=6.87 Hz, CH fluorene or imidazolium); 7.94 (d, 1H, J=8.22 Hz, CH fluorene or imidazolium); 8.05 (s, 1H, CH fluorene or imidazolium); 11.29 (s, 1H, N—CH—N). $^{13}$C NMR (75 MHz, CDCl$_3$): δ=13.51 (C—CH$_3$ aliphatic chain); 22.00; 25.74; 28.47; 28.49; 29.91; 31.12 (CH$_2$ aliphatic chain); 36.43 (CH$_2$ fluorene; 49.83 (N—CH$_2$); 118.04; 119.93; 120.00; 120.54; 120.79; 122.83; 124.59; 126.57; 127.31 (CH fluorene or imidazolium); 132.18 (quaternary C); 134.74 (CH fluorene or imidazolium); 139.05; 142.85; 142.97; 144.76 (quaternary C). $v_{max}$/cm$^{-1}$ 3038 (aromatic C—H); 2923 and 2854 (aliphatic C—H); 1556 (aromatic C=C). UV/Vis (CH$_2$Cl$_2$): $\lambda_{max}$ (ε L·mol$^{-1}$.cm$^{-1}$)=304 nm (19900); 281 nm (22600); 227 nm (12700). Elementary analysis for $C_{24}H_{29}BrN_2$; Calculated: C, 67.76; H, 6.87; N, 6.59%. Found: C, 67.52; H, 6.93; N, 6.31%.

1-(9-methyl-carbazol-3-yl)-3-octyl-2H-imidazol-3-ium Bromide (34)

The general procedure with 30 (1.554 g 6.28 mmol) and 1-bromooctane (13.09 g; 67.78 mmol) allowed 34 to be obtained with a yield of 85% (2.357 g; 5.35 mmol). $^1$H NMR (300 MHz, CDCl$_3$): δ=0.88 (t, 3H, J=6.33 Hz, CH$_3$ aliphatic chain); 1.27-1.40 broad m, 10H, CH$_2$ aliphatic chain and N—CH$_2$—CH$_2$—CH$_2$); 2.02 (qui, 2H, J=7.68 Hz, N—CH$_2$—CH$_2$); 3.87 (s, 3H, CH$_3$ carbazole); 4.61 (t, 2H, J=7.50 Hz, N—CH$_2$); 7.30-7.62 (m, 5H, CH carbazole or imidazolium); 7.68 (broad s, 1H, CH carbazole or imidazolium); 7.86 (d, 1H, J=9.06 Hz; CH carbazole or imidazolium); 8.20 (d, 1H, J=7.95 Hz, CH carbazole or imidazolium); 8.47 (d, 1H, J=2.19 Hz, CH carbazole or imidazolium); 11.12 (s, 1H, N—CH—N). $^{13}$C NMR (75 MHz, CDCl$_3$): δ=13.79 (C—CH$_3$ aliphatic chain); 22.31; 26.05; 28.75; 28.79 (CH$_2$ aliphatic chain); 29.01 (CH$_3$ carbazole); 30.17; 31.43 (CH$_2$ aliphatic chain); 49.97 (N—CH$_2$); 108.65; 109.08; 113.46; 118.29; 119.30; 120.91; 121.19 (CH carbazole or imidazolium); 121.61 (quaternary C); 122.43 (CH carbazole or imidazolium); 122.75; 125.87 (quaternary C); 126.70; 134.79 (CH carbazole or imidazolium); 140.13; 141.29 (quaternary C). $v_{max}$/cm$^{-1}$ 3069 (aromatic C—H); 2922 and 2853 (aliphatic C—H); 1560 (aromatic C=C). UV/Vis (CH$_2$Cl$_2$): $\lambda_{max}$ (ε L·mol$^{-1}$.cm$^{-1}$)=350 nm (3100); 335 nm (4100); 279 nm (31700); 239 nm (31300). Elementary analysis for $C_{24}H_{30}BrN_{3-0.11}H_2O$; Calculated C, 65.16; H, 6.89; N, 9.50%. Found: C, 65.15; H, 6.83; N, 9.47%.

1-(anthracen-9-yl)-3-octyl-2H-imidazol-3-ium Bromide (35)

The general procedure with 31 (0.473 g; 1.94 mmol) and 1-bromooctane (3.487 g; 18.06 mmol) allowed 35 to be obtained with a yield of 93% (0.790 g; 1.81 mmol). $^1$H NMR (300 MHz, CDCl$_3$): δ=0.91 (t, 3H, J=6.57 Hz, CH$_3$ aliphatic chain); 1.31-1.53 (broad m, 10H, CH$_2$ aliphatic chain and N—CH$_2$—CH$_2$—CH$_2$); 2.13 (qui, 2H, J=7.41 Hz, N—CH$_2$—CH$_2$); 4.97 (t, 2H, J=7.41 Hz, N—CH$_2$); 7.36-7.39 (m, 2H, CH anthracene or imidazolium); 7.47 (t, 1H, J=1.65 Hz, CH anthracene or imidazolium), 7.58-7.67 (m, 4H, CH anthracene or imidazolium); 7.92 (t, 1H, J=1.62 Hz, CH anthracene or imidazolium); 8.14-8.17 (m, 2H, CH anthracene or imidazolium); 8.77 (s, 1H, CH anthracene or imidazolium); 10.41 (s, 1H, N—CH—N). $^{13}$C NMR (75 MHz, CDCl$_3$): δ=13.88 (C—CH$_3$ aliphatic chain); 22.40; 26.03; 28.82; 28.90; 30.37; 31.47 (CH$_2$ aliphatic chain); 50.50 (N—CH$_2$); 120.27; 123.95 (CH anthracene or imidazolium); 124.51 (quaternary C); 125.12; 126.11 (CH anthracene or imidazolium); 127.44 (quaternary C); 128.67; 129.07 (CH anthracene or imidazolium); 130.71 (quaternary C); 130.93; 138.58 (CH anthracene or imidazolium). $v_{max}$/cm$^{-1}$ 3042 (aromatic C—H), 2918 and 2852 (aliphatic C—H); 1449 (aromatic C=C). UV/Vis (CH$_2$Cl$_2$): $\lambda_{max}$ (ε L·mol$^{-1}$.cm$^{-1}$)=387 nm (6000); 370 nm (6900); 354 nm (5300); 254 nm (149700). Elementary analysis for C$_{25}$H$_{29}$BrN$_{3-0.9}$H$_2$O; Calculated: C, 66.19; H, 6.84; N, 6.18%. Found: C, 66.19; H, 6.77; N, 6.19%.

General Procedure for Anion Metathesis—Anion Exchange

A mixture of imidazolium bromide dissolved in dichloromethane and a mixture of the corresponding salt in water were left under agitation together for 48 hours. The organic phase was extracted with dichloromethane, dried over calcium chloride and filtered. The filtrate was purified by flash chromatography (silica gel, dichloromethane to dichloromethane/methanol: 95:5) to obtain a pure product.

1-(naphtalen-1-yl)-3-octyl-2H-imidazol-3-ium Tetrafluoroborate (36)

The general procedure with 32 (0.826 g; 2.13 mmol) and potassium tetrafluoroborate (0.589 g; 4.68 mmol) allowed 36 to be obtained with a yield of 92% (0.771 g; 1.96 mmol). $^1$H NMR (300 MHz, CDCl$_3$): δ=0.89 (t, 3H, J=7.14 Hz, CH$_3$ aliphatic chain); 1.28-1.40 (broad m, 10H, CH$_2$ aliphatic chain and N—CH$_2$—CH$_2$—CH$_2$); 2.02 (qui, 2H, J=7.68 Hz, N—CH$_2$—CH$_2$); 4.49 (t, 2H, J=7.68 Hz, N—CH$_2$); 7.47-7.52 (m, 2H, CH naphthalene or imidazolium); 7.57-7.67 (m, 4H, CH naphthalene or imidazolium); 7.79 and 7.82 (dd, 1H, J=1.08 and 7.41 Hz, CH naphthalene or imidazolium); 8.01-8.04 (m, 1H, CH naphthalene or imidazolium); 8.10 (d, 1H, J=8.52 Hz, CH naphthalene or imidazolium); 9.11 (s, 1H, N—CH—N). $^{13}$C NMR (75 MHz, CDCl$_3$): δ=13.94 (C—CH$_3$ aliphatic chain); 22.47; 26.12; 28.80; 28.92; 29.95; 31.56 (CH$_2$ aliphatic chain); 50.47 (N—CH$_2$); 120.51; 123.05; 124.38; 124.54; 125.17; 127.50 (CH naphthalene or imidazolium); 127.53 (quaternary C); 128.67; 128.70 (CH naphthalene or imidazolium); 130.51 (quaternary C); 131.46 (CH naphthalene or imidazolium); 133.99 (quaternary C); 136.41 (CH naphthalene or imidazolium). $v_{max}$/cm$^{-1}$ 3055 (aromatic C—H); 1423 (aromatic C=C); 1053 (BF$_4^-$). UV/Vis (CH$_2$Cl$_2$): $\lambda_{max}$ (ε L·mol$^{-1}$.cm$^{-1}$)=282 nm (7200); 228 nm (33000). Elementary analysis for C$_{21}$H$_{27}$BF$_4$N$_{2-0.12}$H$_2$O; Calculated: C, 63.63; H, 6.93; N, 7.07%. Found: C, 63.62; H, 6.85; N, 7.15%.

1-(naphtalen-1-yl)-3-octyl-2H-imidazol-3-ium Hexafluorophosphate (37)

The general procedure with 32 (0.829 g; 2.14 mmol) and potassium hexafluorophosphate (0.498 g; 2.70 mmol) allowed 37 to be obtained with a yield of 86% (0.829 g; 1.83 mmol). $^1$H NMR (300 MHz, CDCl$_3$): δ=0.89 (t, 3H, J=7.11 Hz, CH$_3$ aliphatic chain); 1.28-1.39 (broad m, 10H, CH$_2$ aliphatic chain and N—CH$_2$—CH$_2$—CH$_2$); 2.01 (qui, 2H, J=7.68 Hz, N—CH$_2$—CH$_2$); 4.42 (t, 2H, J=7.68 Hz, N—CH$_2$); 7.45-7.51 (m, 2H, CH naphthalene or imidazolium); 7.56-7.68 (m, 4H, CH naphthalene or imidazolium); 7.73 and 7.76 (dd, 1H, J=1.11 and 7.41 Hz, CH naphthalene or imidazolium); 7.99-8.03 (m, 1H, CH naphthalene or imidazolium); 8.10 (d, 1H, J=8.25 Hz, CH naphthalene or imidazolium); 8.78 (s, 1H, N—CH—N). $^{13}$C NMR (75 MHz, CDCl$_3$): δ=13.96 (C—CH$_3$ aliphatic chain); 22.50; 26.15; 28.79; 28.93; 29.77; 31.58 (CH$_2$ aliphatic chain); 50.59 (N—CH$_2$); 120.51; 122.91; 124.47; 124.55; 125.18; 127.61 (CH naphthalene or imidazolium); 127.61 (quaternary C); 128.69; 128.86 (CH naphthalene or imidazolium); 130.43 (quaternary C); 131.63 (CH naphthalene or imidazolium); 134.03 (quaternary C); 135.89 (CH naphthalene or imidazolium). $v_{max}$/cm$^{-1}$ 3073 (aromatic C—H); 2928 and 2855 (aliphatic C—H); 1552 (aromatic C=C), 843 (PF$_6^-$). UV/Vis (CH$_2$Cl$_2$): $\lambda_{max}$ (ε L·mol$^{-1}$.cm$^{-1}$)=282 nm (6900); 228 nm (31300). Elementary analysis for C$_{21}$H$_{27}$F$_6$N$_2$P; Calculated: C, 55.75; H, 6.02; N, 6.19%. Found: C, 55.73; H, 6.07; N, 5.82%.

1-(naphtalen-1-yl)-3-octyl-2H-imidazol-3-ium Iodide (38)

The general procedure with 32 (0.831 g; 2.15 mmol) and potassium iodide (0.687 g; 4.14 mmol) allowed 38 to be obtained with a yield of 94% (0.873 g; 2.01 mmol). $^1$H NMR (300 MHz, CDCl$_3$): δ=0.89 (t, 3H, J=7.14 Hz, CH$_3$ aliphatic chain); 1.29-1.51 (broad m, 10H, CH$_2$ aliphatic chain and N—CH$_2$—CH$_2$—CH$_2$); 2.08 (qui, 2H, J=7.68 Hz, N—CH$_2$—CH$_2$); 4.73 (t, 2H, J=7.68 Hz, N—CH$_2$); 7.51-7.55 (m, 2H, CH naphthalene or imidazolium); 7.60-7.68 (m, 4H, CH naphthalene or imidazolium); 7.99-8.05 (m, 2H, CH naphthalene or imidazolium); 8.11 (d, 1H, J=8.52 Hz, CH naphthalene or imidazolium); 10.26 (s, 1H, N—CH—N). $^{13}$C NMR (75 MHz, CDCl$_3$): δ=13.83 (C—CH$_3$ aliphatic chain); 22.34; 26.02; 28.76; 28.81; 30.08; 31.43 (CH$_2$ aliphatic chain); 50.57 (N—CH$_2$); 120.51; 123.26; 124.03; 124.65; 125.10 (CH naphthalene or imidazolium); 127.34 (quaternary C); 127.44; 128.63; 128.66 (CH naphthalene or imidazolium); 130.28 (quaternary C); 131.41 (CH naphthalene or imidazolium); 133.90 (quaternary C); 136.80 (CH naphthalene or imidazolium). $v_{max}$/cm$^{-1}$ 3054 (aromatic C—H); 1422 (aromatic C=C). UV/Vis (CH$_2$Cl$_2$): $\lambda_{max}$ (ε L·mol$^{-1}$.cm$^{-1}$)=364 nm (500); 283 nm (8500); 228 nm (41400). Elementary analysis for C$_{21}$H$_{27}$I$_{0.93}$N$_{2-0.07}$Br; Calculated: C, 58.51; H, 6.31; N, 6.50%. Found: C, 58.52; H, 6.38; N, 6.27%.

1-(naphtalen-1-yl)-3-octyl-2H-imidazol-3-ium bis(trifluoromethylsulfonyl)amide (39)

The general procedure with 32 (0.833 g; 2.15 mmol) and lithium bis(trifluoromethylsulfonyl)amide (1.121 g; 3.91 mmol) allowed 39 to be obtained with a yield of 87% (1.103 g; 1.88 mmol). $^1$H NMR (300 MHz, CDCl$_3$): δ=0.90 (t, 3H, J=6.57 Hz, CH$_3$ aliphatic chain); 1.27-1.42 (broad m, 10H, CH$_2$ aliphatic chain and N—CH$_2$—CH$_2$—CH$_2$); 2.04 (qui, 2H, J=7.68 Hz, N—CH$_2$—CH$_2$); 4.46 (t, 2H, J=7.68 Hz, N—CH$_2$); 7.44-7.47 (m, 1H, CH naphthalene or imidazolium); 7.55-7.70 (m, 5H, CH naphthalene or imidazolium); 7.75 and 7.77 (dd, 1H, J=1.08 and 7.41 Hz, CH naphthalene or imidazolium); 8.03-8.06 (m, 1H, CH naphthalene or imidazolium); 8.13 (d, 1H, J=8.22 Hz, CH naphthalene or imidazolium); 9.01 (s, 1H, N—CH—N). $^{13}$C NMR (75 MHz, CDCl$_3$): δ=13.91 (C—CH$_3$ aliphatic chain); 22.45; 26.07; 28.72; 28.87; 28.87; 29.87; 31.53 (CH$_2$ aliphatic chain); 50.65 (N—CH$_2$); 119.70 (qua, J=319.65 Hz, (CF₃SO₂)₂N⁻); 120.32; 123.02; 124.54; 124.62; 125.12 (CH naphthalene or imidazolium); 127.61 (quaternary C); 127.63; 128.75; 128.86 (CH naphthalene or imidazolium); 130.33 (quaternary C); 131.73 (CH naphthalene or imidazolium); 134.09 (quaternary C); 136.09 (CH naphthalene or imidazolium). $v_{max}$/cm⁻¹ 3054 (aromatic C—H); 1422 (aromatic C═C); 1350 and 1140 ((CF₃SO₂)₂N⁻). UV/Vis (CH₂Cl₂): $\lambda_{max}$ (ε L·mol⁻¹·cm⁻¹)=283 nm (7600); 228 nm (33000). Elementary analysis for $C_{23}H_{27}F_6N_3O_4S_2$; Calculated: C, 47.01; H, 4.63; N, 7.15%. Found: C, 46.99; H, 4.67; N, 7.17%.

1-(9H-fluoren-2-yl)-3-octyl-2H-imidazol-3-ium Tetrafluoroborate (40)

The general procedure with 33 (0.825 g; 1.94 mmol) and potassium tetrafluoroborate (0.817 g; 6.49 mmol) allowed 40 to be obtained with a yield of 75% (0.631 g; 1.46 mmol). ¹H NMR (300 MHz, CDCl₃): δ=0.88 (t, 3H, J=6.30 Hz, CH₃ aliphatic chain); 1.27-1.35 (broad m, 10H, CH₂ aliphatic chain and N—CH₂—CH₂—CH₂); 1.95 (qui, 2H, J=7.68 Hz, N—CH₂—CH₂); 3.99 (s, 2H, CH₂ fluorene) 4.38 (t, 2H, J=7.41 Hz, N—CH₂); 7.36-7.45 (m, 3H, CH fluorene or imidazolium); 7.56-7.61 (m, 3H, CH fluorene or imidazolium); 7.78-7.90 (m, 3H, CH fluorene or imidazolium); 9.35 (s, 1H, N—CH—N). ¹³C NMR (75 MHz, CDCl₃): δ=13.96 (C—CH₃ aliphatic chain); 22.50; 26.18; 28.86; 28.95; 30.07; 31.62 (CH₂ aliphatic chain); 36.85 (CH₂ fluorene); 50.45 (N—CH₂); 118.59; 120.41; 120.45; 121.03; 121.41; 123.07; 125.10; 127.08; 127.85 (CH fluorene or imidazolium); 132.61 (quaternary C); 133.94 (CH fluorene or imidazolium); 139.51; 143.56; 145.44 (quaternary C). $v_{max}$/cm⁻¹ 3042 (aromatic C—H); 2926 and 2856 (aliphatic C—H); 1558 (aromatic C═C), 1030 (BF₄⁻). UV/Vis (CH₂Cl₂): $\lambda_{max}$ (εL·mol⁻¹·cm⁻¹)=304 nm (19300); 281 nm (21900); 227 nm (9300). Elementary analysis for $C_{24}H_{29}BF_4N_2$; Calculated: C, 66.68; H, 6.76; N, 6.48%. Found: C, 66.47; H, 6.71; N, 6.51%.

1-(9H-fluoren-2-yl)-3-octyl-2H-imidazol-3-ium Hexafluorophosphate (41)

The general procedure with 33 (0.829 g; 1.95 mmol) and potassium hexafluorophosphate (0.558 g; 3.03 mmol) allowed 41 to be obtained with a yield of 85% (0.812 g; 1.66 mmol). ¹H NMR (300 MHz, CDCl₃): δ=0.82 (t, 3H, J=6.87 Hz, CH₃ aliphatic chain); 1.21-1.31 (broad m, 10H, CH₂ aliphatic chain and N—CH₂—CH₂—CH₂); 1.92 (qui, 2H, J=7.41 Hz, N—CH₂—CH₂); 3.94 (s, 2H, CH₂ fluorene); 4.30 (t, 2H, J=7.68 Hz, N—CH₂); 7.31-7.40 (m, 2H, CH fluorene or imidazolium); 7.48-7.54 (m, 3H, CH fluorene or imidazolium); 7.64 (t, 1H, J=1.65 Hz, CH fluorene or imidazolium); 7.75-7.78 (m, 2H, CH fluorene or imidazolium); 7.86 (d, 1H, J=8.25 Hz, CH fluorene or imidazolium); 9.04 (s, 1H, N—CH—N). ¹³C NMR (75 MHz, CD₂Cl₂): δ=14.19 (C—CH₃ aliphatic chain); 22.97; 26.60; 29.25; 29.37; 30.38; 32.05 (CH₂ aliphatic chain); 37.41 (CH₂ fluorene); 51.20 (N—CH₂); 119.58; 121.01; 121.40; 121.65; 122.36; 123.39; 125.66; 127.58; 128.51 (CH fluorene or imidazolium); 133.04 (quaternary C); 134.13 (CH fluorene or imidazolium); 140.00; 144.26; 144.57; 146.20 (quaternary C). $v_{max}$/cm⁻¹ 3051 (aromatic C—H); 2926 and 2859 (aliphatic C—H); 1553 (aromatic C═C), 820 (PF₆⁻). UV/Vis (CH₂Cl₂): $\lambda_{max}$ (ε L·mol⁻¹·cm⁻¹)=304 nm (19100); 281 nm (21400); 228 nm (11500). Elementary analysis $C_{24}H_{29}F_6N_2P$; Calculated: C, 58.77; H, 5.96; N, 5.71%. Found: C, 58.58; H, 5.95; N, 5.74%.

1-(9H-fluoren-2-yl)-3-octyl-2H-imidazol-3-ium Iodide (42)

The general procedure with 33 (0.827 g; 1.94 mmol) and potassium iodide (0.608 g; 3.66 mmol) allowed 42 to be obtained with a yield of 82% (0.745 g; 1.58 mmol). ¹H NMR (300 MHz, CDCl₃): δ=0.88 (t, 3H, J=6.60 Hz, CH₃ aliphatic chain); 1.27-1.44 (broad m, 10H, CH₂ aliphatic chain and N—CH₂—CH₂—CH₂); 2.02 (qui, 2H, J=6.84 Hz, N—CH₂—CH₂); 4.03 (s, 2H, CH₂ fluorene); 4.59 (t, 2H, J=7.41 Hz, N—CH₂); 7.34-7.46 (m, 3H, CH fluorene or imidazolium); 7.58-7.63 (m, 2H, CH fluorene or imidazolium); 7.73 and 7.76 (dd, 1H, J=2.19 and 7.89 Hz, CH fluorene or imidazolium); 7.81 and 7.83 (dd, 1H, J=1.65 et 6.03 Hz, CH fluorene or imidazolium); 7.93 (d, 1H, J=8.22 Hz, CH fluorene or imidazolium); 8.06 (d, 1H, J=1.92 Hz, CH fluorene or imidazolium); 10.80 (s, 1H, N—CH—N). ¹³C NMR (75 MHz, CDCl₃): δ=13.83 (C—CH₃ aliphatic chain); 22.35; 26.05; 28.77; 28.82; 30.15; 31.46 (CH₂ aliphatic chain); 36.82 (CH₂ fluorene); 50.41 (N—CH₂); 118.74; 120.36; 120.57; 120.96; 121.13; 123.10; 124.99; 126.95; 127.75 (CH fluorene or imidazolium); 132.33 (quaternary C); 134.55 (CH fluorene or imidazolium); 139.37; 143.40; 143.43; 145.19 (quaternary C). $v_{max}$/cm⁻¹ 3067 (aromatic C—H); 2923 and 2854 (aliphatic C—H); 1556 (aromatic C═C). UV/Vis (CH₂Cl₂): $\lambda_{max}$ (ε L·mol⁻¹·cm⁻¹)=363 nm (1000); 303 nm (21400); 281 nm (23800); 228 nm (21100). Elementary analysis for $C_{24}H_{29}IN_2$; Calculated: C, 61.02; H, 6.19; N, 5.93%. Found: C, 60.99; H, 6.25; N, 5.74%.

1-(9H-fluoren-2-yl)-3-octyl-2H-imidazol-3-ium bis(trifluoromethylsulfonyl)amide (43)

The general procedure with 33 (0.870 g; 2.05 mmol) and lithium bis(trifluoromethylsulfonyl)amide (0.851 g; 2.96 mmol) allowed 43 to be obtained with a yield of 89% (1.141 g; 1.82 mmol). ¹H NMR (300 MHz, CDCl₃): δ=0.89 (t, 3H, J=6.33 Hz, CH₃ aliphatic chain); 1.29-1.38 (broad m, 10H, CH₂ aliphatic chain and N—CH₂—CH₂—CH₂); 1.97 (qui, 2H, J=7.95 Hz, N—CH₂—CH₂); 4.03 (s, 2H, CH₂ fluorene), 4.37 (t, 2H, J=7.71 Hz, N—CH₂); 7.38-7.47 (m, 3H, CH fluorene or imidazolium) 7.53-7.63 (m, 3H, CH fluorene or imidazolium); 7.82-7.86 (m, 2H, CH fluorene or imidazolium); 7.94 (d, 1H, J=8.22 Hz, CH fluorene or imidazolium); 9.24 (s, 1H, N—CH—N). ¹³C NMR (75 MHz, CDCl₃): δ=13.91 (C—CH₃ aliphatic chain); 22.46; 26.07; 28.75; 28.86; 30.01; 31.54 (CH₂ aliphatic chain); 36.84 (CH₂ fluorene); 50.60 (N—CH₂); 119.85 (qua, J=319.10 Hz, (CF₃SO₂)₂N⁻); 118.82; 120.52; 120.67; 121.17; 121.79; 123.12; 125.18; 127.14; 128.01 (CH fluorene or imidazolium); 132.49 (quaternary C); 133.68 (CH fluorene or imidazolium); 139.54; 143.65; 143.96; 145.61 (quaternary C). $v_{max}$/cm⁻¹ 3024 (aromatic C—H); 2931 and 2861 (aliphatic C—H); 1548 (aromatic C═C); 1343 and 1130 ((CF₃SO₂)₂N⁻). UV/Vis (CH₂Cl₂): $\lambda_{max}$ (ε L·mol⁻¹·cm⁻¹)=303 nm (19700); 281 nm (21500); 227 nm (10400). Elementary analysis for $C_{26}H_{29}F_6N_3O_4S_2$; Calculated: C, 49.91; H, 4.67; N, 6.72%. Found: C, 49.95; H, 4.77; N, 6.71%.

1-(9-methyl-carbazol-3-yl)-3-octyl-2H-imidazol-3-ium tetrafluoroborate (44)

The general procedure with 34 (0.459 g; 1.04 mmol) and potassium tetrafluoroborate (0.255 g; 2.03 mmol) allowed 44 to be obtained with a yield of 85% (0.396 g; 8.85 mmol). ¹H NMR (300 MHz, CDCl₃): δ=0.88 (t, 3H, J=6.57 Hz, CH₃ aliphatic chain); 1.27-1; 36 (broad m, 10H, CH₂ aliphatic chain and N—CH₂—CH₂—CH₂); 1.94 (qui, 2H, J=7.68 Hz, N—CH₂—CH₂); 3.79 (s, 3H, CH₃ carbazole); 4.36 (t, 2H, J=7.41 Hz, N—CH₂); 7.29-7.34 (m, 1H, CH carbazole or imidazolium); 7.39-7.44 (m, 3H, CH carbazole or imidazolium); 7.53-7.62 (m, 3H, CH carbazole or imidazolium); 8.16 (d, 1H, J=7.68 Hz, CH carbazole or imidazolium); 8.25 (d, 1H, J=2.22 Hz, CH carbazole or imidazolium); 9.30 (s, 1H, N—CH—N). ¹³C NMR (75 MHz, CDCl₃): δ=13.96 (C—CH₃ aliphatic chain); 22.49; 26.17; 28.81 (CH₂ aliphatic chain); 28.84 (CH₃ carbazole); 28.95; 30.06; 31.60 (CH₂ aliphatic chain); 50.21 (N—CH₂); 108.80; 109.32; 113.28; 118.38; 119.53; 120.79; 121.55 (CH carbazole or imidazolium); 121.65 (quaternary C); 122.65 (CH carbazole or imidazolium); 122.59; 125.93 (quaternary C); 126.8; 133.59 (CH carbazole or imidazolium); 140.37; 141.44 (quaternary C). $v_{max}$/cm⁻¹ 3053 (aromatic C—H); 2924 and 2856 (aliphatic CH); 1560 (aromatic C=C); 1024 (BF₄⁻). UV/Vis (CH₂Cl₂): $\lambda_{max}$ (ε L·mol⁻¹·cm⁻¹)=350 nm (2700); 334 nm (3700); 278 nm (29500); 239 nm (29200). Elementary analysis for $C_{24}H_{30}BF_4N_3$; Calculated: C, 64.44; H, 6.76; N, 9.39%. Found: C, 64.41; H, 6.87; N, 8.91%.

1-(9-methyl-carbazol-3-yl)-3-octyl-2H-imidazol-3-ium Hexafluorophosphate (45)

The general procedure with 34 (0.456 g; 1.04 mmol) and potassium hexafluorophosphate (0.383 g; 2.08 mmol) allowed 45 to be obtained with a yield of 95% (0.465 g; 0.98 mmol). ¹H NMR (300 MHz, CDCl₃): δ=0.88 (t, 3H, J=6.87 Hz, CH₃ aliphatic chain); 1.27-1.34 (broad m, 10H, CH₂ aliphatic chain and N—CH₂—CH₂—CH₂); 1.93 (qui, 2H, J=6.84 Hz, N—CH₂—CH₂); 3.76 (s, 3H, CH₃ carbazole); 4.29 (t, 2H, J=7.41 Hz, N—CH₂); 7.25-7.30 (m, 1H, CH carbazole or imidazolium); 7.38-7.41 (m, 3H, CH carbazole or imidazolium); 7.49-7.57 (m, 3H, CH carbazole or imidazolium); 8.12 (d, 1H, J=7.68 Hz, CH carbazole or imidazolium); 8.18 (d, 1H, J=2.19 Hz, CH carbazole or imidazolium); 8.93 (broad s, 1H, N—CH—N). ¹³C NMR (75 MHz, CDCl₃): δ=13.97 (C—CH₃ aliphatic chain); 22.50; 26.16; 28.79 (CH₂ aliphatic chain); 28.81 (CH₃ carbazole); 28.94; 29.91; 31.60 (CH₂ aliphatic chain); 50.30 (N—CH₂); 108.86; 109.33; 113.39; 118.43; 119.59; 120.65 (CH carbazole or imidazolium); 121.57 (quaternary C); 121.67; 122.53 (CH carbazole or imidazolium); 122.88; 125.82 (quaternary C); 126.94; 133.20; 133.20 (CH carbazole or imidazolium); 140.42; 141.45 (quaternary C). $v_{max}$/cm⁻¹ 3055 (aromatic C—H); 1423 (aromatic C=C); 847 (PF₆⁻). UV/Vis (CH₂Cl₂): $\lambda_{max}$ (ε L·mol⁻¹·cm⁻¹)=350 nm (2700); 335 nm (3800); 280 nm (28700); 239 nm (29100). Elementary analysis for $C_{24}H_{30}F_6N_3P$; Calculated: C, 57.03; H, 5.98; N, 8.31%. Found: C, 57.02; H, 5.94; N, 8.37%.

1-(9-methyl-carbazol-3-yl)-3-octyl-2H-imidazol-3-ium Iodide (46)

The general procedure with 34 (0.454 g; 1.03 mmol) and potassium iodide (0.403 g; 2.43 mmol) allowed 46 to be obtained with a yield of 72% (0.363 g; 0.74 mmol). ¹H NMR (300 MHz, CDCl₃): δ=0.89 (t, 3H, J=6.87 Hz, CH₃ aliphatic chain); 1.28-1.44 (broad m, 10H, CH₂ aliphatic chain and N—CH₂—CH₂—CH₂); 2.02 (qui, 2H, J=7.11 Hz, N—CH₂—CH₂); 3.87 (s, 3H, CH₃ carbazole); 4.57 (t, 2H, J=7.41 Hz, N—CH₂); 7.31-7.60 (m, 4H, CH carbazole or imidazolium); 7.68 (t, 1H, J=1.92 Hz, CH carbazole or imidazolium); 7.84 ad 7.87 (dd, 1H, J=2.19 and 8.79 Hz, CH carbazole or imidazolium); 8.23 (d, 1H, J=7.95 Hz, CH carbazole or imidazolium); 8.49 (d, 1H, J=2.19 Hz, CH carbazole or imidazolium); 10.70 (s, 1H, N—CH—N). ¹³C NMR (75 MHz, CDCl₃): δ=13.86 (C—CH₃ aliphatic chain); 22.38; 26.08; 28.79; 28.85 (CH₂ aliphatic chain); 29.28 (CH₃ carbazole); 30.18; 31.49 (CH₂ aliphatic chain); 50.21 (N—CH₂); 108.78; 109.30; 113.78; 118.51; 119.47; 121.19; 121.37 (CH carbazole or imidazolium); 121.65 (quaternary C); 122.59 (CH carbazole or imidazolium); 122.84; 125.79 (quaternary C); 126.84; 134.24 (CH carbazole or imidazolium); 140.28; 141.37 (quaternary C). $v_{max}$/cm⁻¹ 3049 (aromatic C—H); 2923 and 2853 (aliphatic C—H); 1556 (aromatic C=C). UV/Vis (CH₂Cl₂): $\lambda_{max}$ (ε L·mol⁻¹·cm⁻¹)=352 nm (3300); 335 nm (4200); 281 nm (31500); 239 nm (41700). Elementary analysis for $C_{24}H_{30}IN_3$; Calculated: C, 59.14; H, 6.20; N, 8.62%. Found: C, 59.20; H, 6.25; N, 8.37%.

1-(9-methyl-carbazol-3-yl)-3-octyl-2H-imidazol-3-ium bis(trifluoromethylsulfonyl) Amide (47)

The general procedure with 34 (0.455 g; 1.03 mmol) and lithium bis(trifluoromethylsulfonyl)amide (0.517 g; 1.80 mmol) allowed 47 to be obtained with a yield of 94% (0.621 g; 0.97 mmol). ¹H NMR (300 MHz, CDCl₃): δ=0.89 (t, 3H, J=6.87 Hz, CH₃ aliphatic chain); 1.29-1.38 (broad m, 10H, CH₂ aliphatic chain and N—CH₂—CH₂—CH₂); 1.98 (qui, 2H, J=7.68 Hz, N—CH₂—CH₂); 3.90 (s, 3H, CH₃ carbazole); 4.37 (t, 2H, J=7.68 Hz, N—CH₂); 7.30-7.38 (m, 1H, CH carbazole or imidazolium); 7.43-7.65 (m, 6H, CH carbazole or imidazolium); 8.15 (d, 1H, J=7.95 Hz, CH carbazole or imidazolium); 8.24 (d, 1H, J=2.19 Hz, CH carbazole or imidazolium); 9.15 (s, 1H, N—CH—N). ¹³C NMR (75 MHz, CDCl₃): δ=13.93 (C—CH₃ aliphatic chain); 22.47; 26.10; 28.77; 28.89 (CH₂ aliphatic chain); 29.08 (CH₃ carbazole); 30.05; 31.57 (CH₂ aliphatic chain); 50.45 (N—CH₂); 109.01; 109.64; 113.78; 118.97; 119.82 (CH carbazole or imidazolium); 119.91 (qua, J=319.65 Hz, (CF₃SO₂)₂N⁻); 120.82 (CH carbazole or imidazolium); 121.74 (quaternary C); 122.14; 122.75 (CH carbazole or imidazolium); 123.22; 125.93 (quaternary C); 127.15; 133.48 (CH carbazole or imidazolium); 140.82; 141.71 (quaternary C). $v_{max}$/cm⁻¹ 3082 (aromatic C—H); 2933 and 2859 (aliphatic C—H); 1553 (aromatic C=C); 1354 and 1134 ((CF₃SO₂)₂N⁻). UV/Vis (CH₂Cl₂): $\lambda_{max}$ (ε L·mol⁻¹·cm⁻¹)=350 nm (2800); 335 nm (4000); 280 nm (28700); 239 nm (29500). Elementary analysis for $C_{26}H_{30}F_6N_4O_4S_2$; Calculated: C, 48.74; H, 4.72; N, 8.75%. Found: C, 48.58; H, 4.74; N, 8.64%.

1-(anthracen-9-yl)-3-octyl-2H-imidazol-3-ium Tetrafluoroborate (48)

The general procedure with 35 (0.166 g; 0.38 mmol) and potassium tetrafluoroborate (0.195 g; 1.55 mmol) allowed 48 to be obtained with a yield of 75% (0.126 g; 0.28 mmol). ¹H NMR (300 MHz, CDCl₃): δ=0.90 (t, 3H, J=6.57 Hz, CH₃ aliphatic chain); 1.30-1.43 (broad m, 10H, CH₂ aliphatic chain and N—CH₂—CH₂—CH₂); 2.08 (qui, 2H, J=7.41 Hz, N—CH₂—CH₂); 4.62 (t, 2H, J=7.41 Hz, N—CH₂); 7.37 (d, 2H, J=8.49 Hz, CH anthracene or imidazolium); 7.49 (t, 1H, J=1.65 Hz, CH anthracene or imidazolium); 7.57-7.68 (m, 4H, CH anthracene or imidazolium); 7.83 (t, 1H, J=1.65 Hz, CH anthracene or imidazolium); 8.13-8.16 (m, 2H, CH anthracene or imidazolium); 8.75 (s, 1H, CH anthracene or imidazolium); 9.02 (s, 1H, N—CH—N). ¹³C NMR (75

MHz, CDCl$_3$): δ=14.00 (C—CH$_3$ aliphatic chain); 22.53; 26.14; 28.85; 29.01; 30.07; 31.59 (CH$_2$ aliphatic chain); 50.69 (N—CH$_2$); 120.30; 123.74 (CH anthracene or imidazolium); 124.50 (quaternary C); 125.50; 126.25 (CH anthracene or imidazolium); 127.54 (quaternary C); 128.73; 129.26 (CH anthracene or imidazolium); 130.78 (quaternary C); 131.10; 137.66 (CH anthracene or imidazolium). ν$_{max}$/cm$^{-1}$ 3067 (aromatic C—H); 2927 and 2856 (aliphatic C—H); 1543 (aromatic C=C); 1071 (BF$_4^-$). UV/Vis (CH$_2$Cl$_2$): λ$_{max}$ (ε L·mol$^{-1}$·cm$^{-1}$)=387 nm (6600); 370 nm (8200); 353 nm (6200); 305 nm (1500); 254 nm (163500). Elementary analysis for C$_{25}$H$_{29}$BF$_4$N$_2$; Calculated: C, 67.58; H, 6.58; N, 6.30%. Found: C, 67.44; H, 6.59; N, 6.34%.

1-(anthracen-9-yl)-3-octyl-2H-imidazol-3-ium Hexafluorophosphate (49)

The general procedure with 35 (0.165 g; 0.38 mmol) and potassium hexafluorophosphate (0.171 g; 0.93 mmol) allowed 49 to be obtained with a yield of 63% (0.119 g; 0.24 mmol). $^1$H NMR (300 MHz, CDCl$_3$): δ=0.90 (t, 3H, J=6.33 Hz, CH$_3$ aliphatic chain); 1.30-1.43 (3 broad, 10H, CH$_2$ aliphatic chain N—CH$_2$—CH$_2$—CH$_2$); 2.07 (qui, 2H, J=7.68 Hz, N—CH$_2$—CH$_2$); 4.56 (t, 2H, J=7.68 Hz, N—CH$_2$); 7.37 (d, 2H, J=8.76 Hz, CH anthracene or imidazolium); 7.49 (t, 1H, J=1.65 Hz, CH anthracene or imidazolium); 7.57-7.68 (m, 4H, CH anthracene or imidazolium); 7.80 (t, 1H, J=1.65 Hz, CH anthracene or imidazolium); 8.14 (d, 2H, J=8.52 Hz, CH anthracene or imidazolium); 8.69 (s, 1H, N—CH—N); 8.75 (s, 1H, CH anthracene or imidazolium). $^{13}$C NMR (75 MHz, CDCl$_3$): δ=13.99 (C—CH$_3$ aliphatic chain); 22.53; 26.13; 28.79; 28.98; 29.81; 31.57 (CH$_2$ aliphatic chain); 50.75 (N—CH$_2$); 120.22; 123.64 (CH anthracene or imidazolium); 124.29 (quaternary C); 125.59; 126.28 (CH anthracene or imidazolium); 127.50 (quaternary C); 128.70; 129.37 (CH anthracene or imidazolium); 130.73 (quaternary C); 131.19; 136.89 (CH anthracene or imidazolium). ν$_{max}$/cm$^{-1}$ 3063 (aromatic C—H); 2925 and 2857 (aliphatic C—H); 1548 (aromatic C=C); 878 (PF$_6^-$). UV/Vis (CH$_2$Cl$_2$): λ$_{max}$ (ε L·mol$^{-1}$·cm$^{-1}$)=387 nm (5300); 370 nm (7000); 352 nm (5400); 254 nm (163600). Elementary analysis for C$_{25}$H$_{29}$F$_6$N$_2$P; Calculated: C, 59.76; H, 5.82; N, 5.58%. Found: C, 59.93; H, 5.92; N, 5.49%.

1-(anthracen-9-yl)-3-octyl-2H-imidazol-3-ium Iodide (50)

The general procedure with 35 (0.167 g; 0.38 mmol) and potassium iodide (0.150 g; 0.91 mmol) allowed 50 to be obtained with a yield of 71% (0.131 g; 0.27 mmol). $^1$H NMR (300 MHz, CDCl$_3$): δ=0.90 (t, 3H, J=6.30 Hz, CH$_3$ aliphatic chain); 1.31-1.50 (broad m, 10H, CH$_2$ aliphatic chain and N—CH$_2$—CH$_2$—CH$_2$); 2.14 (qui, 2H, J=7.68 Hz, N—CH$_2$—CH$_2$); 4.93 (t, 2H, J=7.41 Hz, N—CH$_2$); 7.42 (d, 2H, J=8.52 Hz, CH anthracene or imidazolium); 7.50 (t, 1H, J=1.65 Hz, CH anthracene or imidazolium); 7.59-7.69 (m, 4H, CH anthracene or imidazolium); 7.94 (t, 1H, J=1.65 Hz, CH anthracene or imidazolium); 8.15-8.18 (m, 2H, CH anthracene or imidazolium); 8.77 (s, 1H, CH anthracene or imidazolium); 10.09 (s, 1H, N—CH—N). $^{13}$C NMR (75 MHz, CDCl$_3$): δ=13.91 (C—CH$_3$ aliphatic chain); 22.42; 26.02; 28.83; 28.92; 30.31; 31.49 (CH$_2$ aliphatic chain); 50.85 (N—CH$_2$); 120.41; 124.18 (CH anthracene or imidazolium); 124.33 (quaternary C); 125.21; 126.20 (CH anthracene or imidazolium); 127.42 (quaternary C); 128.70; 129.26 (CH anthracene or imidazolium); 130.73 (quaternary C); 131.07; 137.89 (CH anthracene or imidazolium). ν$_{max}$/cm$^{-1}$ 3051 (aromatic C—H); 2924 and 2852 (aliphatic C—H); 1543 (aromatic C=C). UV/Vis (CH$_2$Cl$_2$): λ$_{max}$ (ε L·mol$^{-1}$·cm$^{-1}$)=387 nm (6100); 370 nm (7700); 353 nm (6000); 322 nm (2100); 254 nm (159100). Elementary analysis for C$_{25}$H$_{29}$IN$_2$; Calculated: C, 61.99; H, 6.03; N, 5.78%. Found: C, 61.97; H, 6.20; N, 5.51%.

1-(anthracen-9-yl)-3-octyl-2H-imidazol-3-ium bis(trifluoromethylsulfonyl)amide (51)

The general procedure with 35 (0.165 g; 0.38 mmol) and lithium bis(trifluoromethylsulfonyl)amide (0.192 g; 0.67 mmol) allowed 51 to be obtained with a yield of 65% (0.155 g; 0.24 mmol). $^1$H NMR (300 MHz, CDCl$_3$): δ=0.90 (t, 3H, J=6.57 Hz, CH$_3$ aliphatic chain); 1.31-1.49 (broad m, 10H, CH$_2$ aliphatic chain and N—CH$_2$—CH$_2$—CH$_2$); 2.10 (qui, 2H, J=7.14 Hz, N—CH$_2$—CH$_2$); 4.58 (t, 2H, J=7.41 Hz, N—CH$_2$); 7.36 (d, 2H, J=8.76 Hz, CH anthracene or imidazolium); 7.54 (t, 1H, J=1.65 Hz, CH anthracene or imidazolium); 7.60-7.70 (m, 4H, CH anthracene or imidazolium); 7.83 (t, 1H, J=1.65 Hz, CH anthracene or imidazolium); 8.16-8.19 (m, 2H, CH anthracene or imidazolium); 8.78 (s, 1H, CH anthracene or imidazolium); 8.90 (s, 1H, N—CH—N). $^{13}$C NMR (75 MHz, CDCl$_3$): δ=13.98 (C—CH$_3$ aliphatic chain); 22.53; 26.14; 28.78; 28.98; 29.98; 31.56 (CH$_2$ aliphatic chain); 50.96 (N—CH$_2$); 119.69 (qua, J=319.65 Hz, (CF$_3$SO$_2$)$_2$N$^-$); 120.09; 123.68 (CH anthracene or imidazolium); 124.27 (quaternary C); 125.74; 126.40 (CH anthracene or imidazolium); 127.63 (quaternary C); 128.86; 129.50 (CH anthracene or imidazolium); 130.89 (quaternary C); 131.36; 137.42 (CH anthracene or imidazolium). ν$_{max}$/cm$^{-1}$ 3073 (aromatic C—H); 2928 and 2858 (aliphatic C—H); 1549 (aromatic C=C); 1347 and 1138 (N(SO$_2$CF$_3$)$_2^-$). UV/Vis (CH$_2$Cl$_2$): λ$_{max}$ (ε L·mol$^{-1}$·cm$^{-1}$)=387 nm (5900); 370 nm (7700); 351 nm (5900); 254 nm (165600). Elementary analysis for C$_{25}$H$_{29}$N$_2$·(N(SO$_2$CF$_3$)$_2$)$_{0.975-0.025}$Br; Calculated: C, 51.16; H, 4.62; N, 6.59%. Found: C, 51.18; H, 4.77; N, 6.40%.

Imidazolium 52 to 71 with C$_{12}$ Carbon Chain

General Procedure for Imidazolium Synthesis (N-Alkylation).

A mixture of imidazole derivative and 1-bromododecane was heated to 110° C. in a round-bottom flask under static vacuum for 12 hours or in a microwave oven for 140 minutes in a sealed tube. The corresponding imidazolium salt was purified by flash chromatography (silica gel, dichloromethane to dichloromethane/methanol: 95:5).

3-dodecyl-1-(naphtalen-1-yl)-2H-imidazol-3-ium Bromide (52)

The general procedure with 28 (1.288 g; 6.63 mmol) and 1-bromododecane (1.999 g; 8.02 mmol) allowed 52 to be obtained with a yield of 86% (2.516 g; 5.67 mmol). $^1$H NMR (300 MHz, CDCl$_3$): δ=0.89 (t, 3H, J=6.33 Hz, CH$_3$ aliphatic chain); 1.27-1.50 (broad m, 18H, CH$_2$ aliphatic chain and N—CH$_2$—CH$_2$—CH$_2$); 2.07 (qui, 2H, J=7.11 Hz, N—CH$_2$—CH$_2$); 4.78 (t, 2H, J=7.11 Hz, N—CH$_2$); 7.49-7.68 (m, 6H, CH naphthalene or imidazolium); 7.93 (d, 1H, J=7.41 Hz, CH naphthalene or imidazolium); 8.01-8.04 (m, 1H, CH naphthalene or imidazolium); 8.10 (d, 1H, J=8.52 Hz, CH naphthalene or imidazolium); 10.68 (s, 1H, N—CH—N). $^{13}$C NMR (75 MHz, CDCl$_3$): δ=13.94 (C—CH$_3$ aliphatic chain); 22.50; 26.18; 28.95; 29.16; 29.28; 29.38; 29.44; 29.46; 30.29; 31.74 (CH$_2$ aliphatic chain);

50.48 (N—CH$_2$); 120.52; 123.00 (CH naphthalene or imidazolium); 123.03 (quaternary C); 123.94; 124.66; 125.21; 127.47; 128.65; 128.73 (CH naphthalene or imidazolium); 130.52 (quaternary C); 131.42 (CH naphthalene or imidazolium); 134.03 (quaternary C); 137.72 (CH naphthalene or imidazolium). $v_{max}$/cm$^{-1}$ 3059 (aromatic C—H); 2921 and 2849 (aliphatic C—H); 1510 (aromatic C=C). UV/Vis (CH$_2$Cl$_2$): $\lambda_{max}$ ($\epsilon$ L·mol$^{-1}$·cm$^{-1}$)=283 nm (7100); 228 nm (35700). Elementary analysis for C$_{25}$H$_{35}$BrN$_2$; Calculated: C, 67.71; H, 7.96; N, 6.32%. Found: C, 67.73; H, 8.06; N, 6.40%.

3-dodecyl-1-(9H-fluoren-2-yl)-2H-imidazol-3-ium Bromide (53)

The general procedure with 29 (10.686 g; 46.00 mmol) and 1-bromododecane (44.979 g; 180.47 mmol) allowed 53 to be obtained with a yield of 86% (18.948 g; 39.35 mmol). $^1$H NMR (300 MHz, CDCl$_3$): δ=0.89 (t, 3H, J=6.30 Hz, CH$_3$ aliphatic chain); 1.26-1.44 (broad m, 18H, CH$_2$ aliphatic chain and N—CH$_2$—CH$_2$—CH$_2$); 2.02 (qui, 2H, J=7.41 Hz, N—CH$_2$—CH$_2$); 4.02 (s, 2H, CH$_2$ fluorene); 4.64 (t, 2H, J=7.41 Hz, N—CH$_2$); 7.37-7.46 (m, 3H, CH fluorene or imidazolium); 7.59-7.61 (m, 2H, CH fluorene or imidazolium); 7.73 and 7.76 (dd, 1H, J=2.19 and 8.22 Hz, CH fluorene or imidazolium); 7.83 (d, 1H, J=7.14 Hz, CH fluorene or imidazolium); 7.93 (d, 1H, J=8.22 Hz, CH fluorene or imidazolium); 8.05 (s, 1H, CH fluorene or imidazolium); 11.29 (s, 1H, N—CH—N). $^{13}$C NMR (75 MHz, CDCl$_3$): δ=13.86 (C—CH$_3$ aliphatic chain); 22.42; 26.10; 28.87; 29.08; 29.19; 29.30; 29.35; 29.37; 30.23; 31.65 (CH$_2$ aliphatic chain); 36.79 (CH$_2$ fluorene); 50.22 (N—CH$_2$); 118.43; 120.28; 120.37; 120.91; 120.98; 122.94; 124.94; 126.91; 127.68 (CH fluorene or imidazolium); 132.51 (quaternary C); 135.29 (CH fluorene or imidazolium); 139.40; 143.31; 143.34; 145.16 (quaternary C). $v_{max}$/cm$^{-1}$ 3041 (aromatic C—H); 2919 and 2851 (aliphatic C—H); 1556 (aromatic C=C). UV/Vis (CH$_2$Cl$_2$): $\lambda_{max}$ ($\epsilon$ L·mol$^{-1}$·cm$^{-1}$)=304 nm (19700); 281 nm (22300); 227 nm (15600). Elementary analysis for C$_{28}$H$_{37}$BrN$_2$; Calculated: C, 69.84; H, 7.75; N, 5.82%. Found: C, 69.87; H, 7.82; N, 5.89%.

3-dodecyl-1-(9-methylcarbazol-3-yl)-2H-imidazol-3-ium Bromide (54)

The general procedure with 30 (0.297 g; 1.20 mmol) and 1-bromododecane (1.708 g; 6.85 mmol) allowed 54 to be obtained with a yield of 77% (0.458 g; 0.92 mmol). $^1$H NMR (300 MHz, CDCl$_3$): δ=0.88 (t, 3H, J=6.60 Hz, CH$_3$ aliphatic chain); 1.26-1.40 (m broad, 18H, CH$_2$ aliphatic chain and N—CH$_2$—CH$_2$—CH$_2$); 2.02 (qui, 2H, J=7.14 Hz, N—CH$_2$—CH$_2$); 3.88 (s, 3H, CH$_3$ carbazole); 4.62 (t, 2H, J=7.14 Hz, N—CH$_2$); 7.31-7.33 (m, 1H, CH carbazole or imidazolium); 7.39-7.67 (m, 5H, CH carbazole or imidazolium); 7.88 (d, 1H, J=9.06 Hz, CH carbazole or imidazolium); 8.21 (d, 1H, J=7.68 Hz, CH carbazole or imidazolium); 8.47 (d, 1H, J=2.22 Hz, CH carbazole or imidazolium); 11.15 (s, 1H, N—CH—N). $^{13}$C NMR (75 MHz, CDCl$_3$): δ=13.92 (C—CH$_3$ aliphatic chain); 22.48; 26.16; 28.91 (CH$_2$ aliphatic chain); 29.11 (CH$_3$ carbazole); 29.14; 29.25; 29.36; 29.41; 29.43; 30.26; 31.71 (CH$_2$ aliphatic chain); 50.10 (N—CH$_2$); 108.74; 109.23; 113.56; 118.46; 119.45; 121.03; 121.23 (CH carbazole or imidazolium); 121.72 (quaternary C); 122.41 (CH carbazole or imidazolium); 122.89; 125.98 (quaternary C); 126.81; 135.02 (CH carbazole or imidazolium); 140.28; 141.42 (quaternary C). $v_{max}$/cm$^{-1}$ 3073 (aromatic C—H); 2917 and 2851 (aliphatic C—H); 1561 (aromatic C=C). UV/Vis (CH$_2$Cl$_2$): $\lambda_{max}$ ($\epsilon$ L·mol$^{-1}$·cm$^{-1}$)=352 nm (3000); 335 nm (4000); 280 nm (31900); 239 nm (31700); 229 nm (28600). Elementary analysis for C$_{28}$H$_{38}$BrN$_3$; Calculated: C, 67.73; H, 7.71; N, 8.46%. Found: C, 67.54; H, 7.77; N, 8.54%.

1-(anthracen-9-yl)-3-dodecyl-2H-imidazol-3-ium Bromide (55)

The general procedure with 31 (0.417 g, 1.71 mmol) and 1-bromododecane (2.969 g, 11.91 mmol) allowed 55 to be obtained with a yield of 95% (0.796 g; 1.61 mmol). $^1$H NMR (300 MHz, CDCl$_3$): δ=0.89 (t, 3H, J=6.87 Hz, CH$_3$ aliphatic chain); 1.28-1.53 (broad m, 18H, CH$_2$ aliphatic chain and N—CH$_2$—CH$_2$—CH$_2$); 2.13 (qui, 2H, J=7.41 Hz, N—CH$_2$—CH$_2$); 4.97 (t, 2H, J=7.41 Hz, N—CH$_2$); 7.36-7.40 (m, 2H, CH anthracene or imidazolium); 7.47 (t, 1H, J=1.65 Hz, CH anthracene or imidazolium); 7.58-7.68 (m, 4H, CH anthracene or imidazolium); 7.92 (s, 1H, CH anthracene or imidazolium); 8.14-8.17 (m, 2H, CH anthracene or imidazolium); 8.77 (s, 1H, CH anthracene or imidazolium); 10.43 (s, 1H, N—CH—N). $^{13}$C NMR (75 MHz, CDCl$_3$): δ=13.96 (C—CH$_3$ aliphatic chain); 22.52; 26.13; 28.95; 29.18; 29.33; 29.38; 29.46; 29.49; 30.40; 31.75 (CH$_2$ aliphatic chain); 50.63 (N—CH$_2$); 120.35; 123.87 (CH anthracene or imidazolium); 124.55 (quaternary C); 125.15; 126.17 (CH anthracene or imidazolium); 127.50 (quaternary C); 128.72; 129.15 (CH anthracene or imidazolium); 130.77 (quaternary C); 131.00; 138.62 (CH anthracene or imidazolium). $v_{max}$/cm$^{-1}$ 3043 (aromatic C—H); 2916 and 2849 (aliphatic C—H); 1466 (aromatic C=C). UV/Vis (CH$_2$Cl$_2$): $\lambda_{max}$ ($\epsilon$ L·mol$^{-1}$·cm$^{-1}$)=387 nm (6500); 369 nm (7500); 352 nm (6000); 255 nm (161300). Elementary analysis for C$_{29}$H$_{37}$BrN$_{2-1.02}$H$_2$O; Calculated: C, 68.04; H, 7.69; N, 5.47%. Found: C, 68.04; H, 7.59; N, 5.51%.

General Procedure for Anion Metathesis—Anion Exchange

A mixture of imidazolium bromide dissolved in dichloromethane and a mixture of the corresponding salt in water were left under agitation together for 48 hours. The organic phase was extracted with dichloromethane, dried over calcium chloride and filtered. The filtrate was purified by flash chromatography (silica gel, dichloromethane to dichloromethane/methanol: 95:5) to obtain a pure product.

3-dodecyl-1-(naphtalen-1-yl)-2H-imidazol-3-ium Tetrafluoroborate (56)

The general procedure with 52 (0.819 g; 1.85 mmol) and potassium tetrafluoroborate (0.630 g; 5.00 mmol) allowed 56 to be obtained with a yield of 53% (0.437 g; 0.97 mmol). $^1$H NMR (300 MHz, CDCl$_3$): δ=0.89 (t, 3H, J=6.84 Hz, CH$_3$ aliphatic chain); 1.27-1.40 (broad m, 18H, CH$_2$ aliphatic chain and N—CH$_2$—CH$_2$—CH$_2$); 2.02 (qui, 2H, J=7.41 Hz, N—CH$_2$—CH$_2$); 4.49 (t, 2H, J=7.41 Hz, N—CH$_2$); 7.47-7.51 (m, 2H, CH naphthalene or imidazolium); 7.57-7.67 (m, 4H, CH naphthalene or imidazolium); 7.80 (d, 1H, J=7.41, CH naphthalene or imidazolium); 8.01-8.04 (m, 1H, CH naphthalene or imidazolium); 8.10 (d, 1H, J=8.22 Hz, CH naphthalene or imidazolium); 9.10 (s, 1H, N—CH—N). $^{13}$C NMR (75 MHz, CDCl$_3$): δ=14.00 (C—CH$_3$ aliphatic chain); 22.58; 26.18; 28.91; 29.24; 29.33; 29.44; 29.53; 29.54; 29.98; 31.81 (CH$_2$ aliphatic chain); 50.50 (N—CH$_2$) 120.54; 123.04; 124.38; 124.57; 125.19; 127.51 (CH naphthalene or imidazolium); 127.56 (quaternary C); 128.68; 128.73 (CH naphthalene or imidazolium); 130.54 (quaternary C); 131.47 (CH naphthalene or imidazolium); 134.01 (quaternary C); 136.46 (CH naphthalene or imidazolium). $v_{max}/cm^{-1}$ 3055 (aromatic C—H); 2929 and 2857 (aliphatic C—H); 1422 (aromatic C═C); 1053 ($BF_4^-$). UV/Vis ($CH_2Cl_2$): $\lambda_{max}$ (ε L·mol$^{-1}$·cm$^{-1}$)=283 nm (7100); 229 nm (26700). Elementary analysis for $C_{25}H_{35}BF_4N_2$; Calculated: C, 66.67; H, 7.83; N, 6.22%. Found: C, 66.50; H, 7.98; N, 6.28%.

3-dodecyl-1-(naphtalen-1-yl)-2H-imidazol-3-ium Hexafluorophosphate (57)

The general procedure with 52 (0.833 g; 1.88 mmol) and potassium hexafluorophosphate (0.812 g; 4.41 mmol) allowed 57 to be obtained with a yield of 71% (0.676 g; 1.51 mmol). $^1$H NMR (300 MHz, CDCl$_3$): δ=0.89 (t, 3H, J=6.33 Hz, CH$_3$ aliphatic chain); 1.27-1.39 (broad m, 18H, CH$_2$ aliphatic chain and N—CH$_2$—CH$_2$—CH$_2$); 2.01 (qui, 2H, J=7.41 Hz, N—CH$_2$—CH$_2$); 4.42 (t, 2H, J=7.41 Hz, N—CH$_2$); 7.45-7.50 (m, 2H, CH naphthalene or imidazolium); 7.56-7.68 (m, 4H, CH naphthalene or imidazolium); 7.74 (d, 1H, J=7.41 Hz, CH naphthalene or imidazolium); 7.99-8.04 (m, 1H, CH naphthalene or imidazolium); 8.10 (d, 1H, J=8.49 Hz, CH naphthalene or imidazolium); 8.77 (s, 1H, N—CH—N). $^{13}$C NMR (75 MHz, CDCl$_3$): δ=14.05 (C—CH$_3$ aliphatic chain); 22.63; 26.22; 28.91; 29.28; 29.35; 29.47; 29.57; 29.81; 31.86 (CH$_2$ aliphatic chain); 50.63 (N—CH$_2$); 120.54; 122.91; 124.47; 124.61; 125.22; 127.63 (CH naphthalene or imidazolium); 127.65 (quaternary C); 128.70; 128.89 (CH naphthalene or imidazolium); 130.46 (quaternary C); 131.65 (CH naphthalene or imidazolium); 134.05 (quaternary C); 135.92 (CH naphthalene or imidazolium). $v_{max}/cm^{-1}$ 3163 (aromatic C—H); 2919 and 2852 (aliphatic C—H); 1514 (aromatic C═C); 820 ($PF_6^-$). UV/Vis ($CH_2Cl_2$): $\lambda_{max}$ (ε L·mol$^{-1}$·cm$^{-1}$)=283 nm (7100); 229 nm (27300). Elementary analysis for $C_{25}H_{35}F_6N_2P_{0.1}H_2O$; Calculated: C, 58.84; H, 6.95; N, 5.49%. Found: C, 58.83; H, 7.07; N, 5.54%.

3-dodecyl-1-(naphtalen-1-yl)-2H-imidazol-3-ium Iodide (58)

The general procedure with 52 (1.056 g; 2.38 mmol) and potassium iodide (0.878 g; 5.29 mmol) allowed 58 to be obtained with a yield of 76% (0.893 g; 1.82 mmol). $^1$H NMR (300 MHz, CDCl$_3$): δ=0.89 (t, 3H, J=6.30 Hz, CH$_3$ aliphatic chain); 1.27-1.51 (broad m, 18H, CH$_2$ aliphatic chain and N—CH$_2$—CH$_2$—CH$_2$); 2.09 (qui, 2H, J=7.68 Hz, N—CH$_2$—CH$_2$); 4.73 (t, 2H, J=7.68 Hz, N—CH$_2$); 7.50-7.53 (m, 2H, CH naphthalene or imidazolium); 7.60-7.68 (m, 4H, CH naphthalene or imidazolium); 7.89 (d, 1H, J=7.41 Hz, CH naphthalene or imidazolium); 8.02-8.05 (m, 1H, CH naphthalene or imidazolium); 8.11 (d, 1H, J=8.22 Hz, CH naphthalene or imidazolium); 10.43 (s, 1H, N—CH—N). $^{13}$C NMR (75 MHz, CDCl$_3$): δ=13.92 (C—CH$_3$ aliphatic chain); 22.47; 26.11; 29.13; 29.25; 29.35; 29.41; 29.43; 30.13; 31.70 (CH$_2$ aliphatic chain); 50.72 (N—CH$_2$); 120.58; 123.25; 124.06; 124.76; 125.18 (CH naphthalene or imidazolium); 127.42 (quaternary C); 127.50; 128.70; 128.73 (CH naphthalene or imidazolium); 130.34 (quaternary C); 131.48 (CH naphthalene or imidazolium); 133.98 (quaternary C); 136.84 (CH naphthalene or imidazolium). $v_{max}/cm^{-1}$ 3054 (aromatic C—H); 2929 and 2856 (aliphatic C—H); 1422 (aromatic C═C). UV/Vis ($CH_2Cl_2$): $\lambda_{max}$ (ε L·mol$^{-1}$·cm$^{-1}$)=283 nm (8100); 230 nm (25300). Elementary analysis for $C_{25}H_{35}IN_{2\text{-}0.3}H_2O$; Calculated: C, 60.55; H, 7.24; N, 5.65%. Found: C, 60.56; H, 7.23; N, 5.55%.

3-dodecyl-1-(naphtalen-1-yl)-2H-imidazol-3-ium bis(trifluoromethylsulfonyl)amide (59)

The general procedure with 52 (1.185 g; 2.67 mmol) and lithium bis(trifluoromethylsulfonyl)amide (1.229 g; 4.28 mmol) allowed 59 to be obtained with a yield of 74% (1.274 g; 1.98 mmol). $^1$H NMR (300 MHz, CDCl$_3$): δ=0.89 (t, 3H, J=6.30 Hz, CH$_3$ aliphatic chain); 1.27-1.42 (broad m, 18H, CH$_2$ aliphatic chain and N—CH$_2$—CH$_2$—CH$_2$); 2.04 (qui, 2H, J=7.95 Hz, N—CH$_2$—CH$_2$); 4.47 (t, 2H, J=7.68 Hz, N—CH$_2$); 7.44-7.47 (m, 1H, CH naphthalene or imidazolium); 7.57 (d, 1H, J=8.22 Hz, CH naphthalene or imidazolium); 7.62-7.71 (m, 1H, CH naphthalene or imidazolium); 7.76 (d, 1H, J=7.41 Hz, CH naphthalene or imidazolium); 8.03-8.06 (m, 1H, CH naphthalene or imidazolium); 8.13 (d, 1H, J=8.49 Hz, CH naphthalene or imidazolium); 9.01 (s, 1H, N—CH—N). $^{13}$C NMR (75 MHz, CDCl$_3$): δ=14.00 (C—CH$_3$ aliphatic chain); 22.59; 26.12; 28.82; 29.25; 29.27; 29.39; 29.51; 29.90; 31.82 (CH$_2$ aliphatic chain); 50.69 (N—CH$_2$); 119.72 (qua, J=319.65 Hz, (CF$_3$SO$_2$)$_2$N$^-$); 120.33; 123.02; 124.57; 124.63; 125.14 (CH naphthalene or imidazolium); 127.63 (quaternary C); 127.65; 128.77; 128.89 (CH naphthalene or imidazolium); 130.35 (quaternary C); 131.75 (CH naphthalene or imidazolium); 134.11 (quaternary C); 136.13 (CH naphthalene or imidazolium). $v_{max}/cm^{-1}$ 3055 (aromatic C—H); 2930 and 2857 (aliphatic C—H); 1422 (aromatic C═C); 1350 ad 1196 ((CF$_3$SO$_2$)$_2$N$^-$). UV/Vis ($CH_2Cl_2$): $\lambda_{max}$ (ε L·mol$^{-1}$·cm$^{-1}$)=283 nm (7400); 228 nm (33800). Elementary analysis for $C_{27}H_{35}F_6N_3O_4S_2$; Calculated: C, 50.38; H, 5.48; N, 6.53%. Found: C, 50.56; H, 5.55; N, 6.67%.

3-dodecyl-1-(9H-fluoren-2-yl)-2H-imidazol-3-ium Tetrafluoroborate (60)

The general procedure with 53 (18.948 g; 39.35 mmol) and potassium tetrafluoroborate (7.634 g; 60.63 mmol) allowed 60 to be obtained with a yield of 84% (16.095 g; 32.95 mmol). $^1$H NMR (300 MHz, CDCl$_3$): δ=0.88 (t, 3H, J=6.33 Hz, CH$_3$ aliphatic chain); 1.25-1.35 (broad m, 18H, CH$_2$ aliphatic chain and N—CH$_2$—CH$_2$—CH$_2$); 1.95 (qui, 2H, J=7.68 Hz, N—CH$_2$—CH$_2$); 3.99 (s, 2H, CH$_2$ fluorene); 4.38 (t, 2H, J=7.68 Hz, N—CH$_2$); 7.36-7.45 (m, 3H, CH fluorene or imidazolium); 7.56-7.61 (m, 3H, CH fluorene or imidazolium); 7.78-7.90 (m, 3H, CH fluorene or imidazolium); 9.34 (s, 1H, N—CH—N). $^{13}$C NMR (75 MHz, CDCl$_3$): δ=14.04 (C—CH$_3$ aliphatic chain); 22.62; 26.22; 28.95; 29.27; 29.35; 29.49; 29.55; 29.57; 30.08; 31.85 (CH$_2$ aliphatic chain); 36.87 (CH$_2$ fluorene); 50.48 (N—CH$_2$); 118.65; 120.47; 121.05; 121.39; 123.01; 125.13; 127.08; 127.89 (CH fluorene or imidazolium); 132.61 (quaternary C); 134.03 (CH fluorene or imidazolium); 139.53; 143.59; 143.61; 145.48 (quaternary C). $v_{max}/cm^{-1}$ 3154 (aromatic C—H); 2924 and 2854 (aliphatic C—H); 1558 (aromatic C═C); 1067 ($BF_4^-$). UV/Vis ($CH_2Cl_2$): $\lambda_{max}$ (ε L·mol$^{-1}$·cm$^{-1}$)=304 nm (18800); 280 nm (21500); 229 nm (10200). Elementary analysis for $C_{28}H_{37}BF_4N_2$; Calculated: C, 68.86; H, 7.64; N, 5.74%. Found: C, 68.67; H, 7.77; N, 5.82%.

3-dodecyl-1-(9H-fluoren-2-yl)-2H-imidazol-3-ium Hexafluorophosphate (61)

The general procedure with 53 (0.898 g; 1.86 mmol) and potassium hexafluorophosphate (0.869 g; 4.72 mmol)

allowed 61 to be obtained with a yield of 68% (0.689 g; 1.26 mmol). $^1$H NMR (300 MHz, CDCl$_3$): δ=0.89 (t, 3H, J=6.30 Hz, CH$_3$ aliphatic chain); 1.25-1.34 (broad m, 18H, CH$_2$ aliphatic chain and N—CH$_2$—CH$_2$—CH$_2$); 1.94 (qui, 2H, J=7.14 Hz, N—CH$_2$—CH$_2$); 3.97 (s, 2H, CH$_2$ fluorene); 4.31 (t, 2H, J=7.11 Hz, N—CH$_2$); 7.36-7.45 (m, 3H, CH fluorene or imidazolium); 7.51-7.57 (m, 3H, CH fluorene or imidazolium); 7.77-7.89 (m, 3H, CH fluorene or imidazolium); 8.98 (s, 1H, N—CH—N). $^{13}$C NMR (75 MHz, CDCl$_3$): δ=14.04 (C—CH$_3$ aliphatic chain); 22.62; 26.21; 28.91; 29.28; 29.33; 29.48; 29.57; 29.91; 31.86 (CH$_2$ aliphatic chain); 36.79 (CH$_2$ fluorene); 50.54 (N—CH$_2$); 118.78; 120.47; 120.53; 121.01; 121.53; 123.00; 125.11; 127.10; 127.93 (CH fluorene or imidazolium); 132.53 (quaternary C); 133.50 (CH fluorene or imidazolium); 139.47; 143.57; 143.71; 145.47 (quaternary C). ν$_{max}$/cm$^{-1}$ 3166 (aromatic C—H); 2919 and 2851 (aliphatic C—H); 1550 (aromatic C=C); 828 (PF$_6^-$). UV/Vis (CH$_2$Cl$_2$): λ$_{max}$ (ε L·mol$^{-1}$·cm$^{-1}$)=304 nm (18700); 281 nm (20600); 229 nm (10300). Elementary analysis for C$_{28}$H$_{37}$F$_6$N$_2$P$_{·0.1}$H$_2$O; Calculated: C, 61.33; H, 6.84; N, 5.11%. Found: C, 61.30; H, 6.94; N, 5.19%.

3-dodecyl-1-(9H-fluoren-2-yl)-2H-imidazol-3-ium Iodide (62)

The general procedure with 53 (0.750 g; 1.56 mmol) and potassium iodide (0.443 g; 2.67 mmol) allowed 62 to be obtained with a yield of 62% (0.513 g; 0.97 mmol). $^1$H NMR (300 MHz, CDCl$_3$): δ=0.89 (t, 3H, J=6.57 Hz, CH$_3$ aliphatic chain); 1.26-1.40 (broad m, 18H, CH$_2$ aliphatic chain and N—CH$_2$—CH$_2$—CH$_2$); 2.03 (qui, 2H, J=7.41 Hz, N—CH$_2$—CH$_2$); 4.04 (s, 2H, CH$_2$ fluorene); 4.60 (t, 2H, J=7.41 Hz, N—CH$_2$); 7.37-7.46 (m, 3H, CH fluorene or imidazolium); 7.59-7.62 (m, 2H, CH fluorene or imidazolium); 7.73 and 7.75 (dd, 1H, J=2.19 and 8.25 Hz, CH fluorene or imidazolium); 7.83 (d, 1H, J=6.57 Hz, CH fluorene or imidazolium); 7.94 (d, 1H, J=8.22 Hz, CH fluorene or imidazolium); 8.06 (broad s, 1H, CH fluorene or imidazolium); 10.82 (s, 1H, N—CH—N). $^{13}$C NMR (75 MHz, CDCl$_3$): δ=13.96 (C—CH$_3$ aliphatic chain); 22.53; 26.15; 28.93; 29.18; 29.28; 29.40; 29.46; 29.47; 30.23; 31.75 (CH$_2$ aliphatic chain); 36.93 (CH$_2$ fluorene); 50.55 (N—CH$_2$); 118.87; 120.46; 120.68; 121.06; 121.11; 123.03; 125.10; 127.05; 127.87 (CH fluorene or imidazolium); 132.40 (quaternary C); 134.74 (CH fluorene or imidazolium); 139.46; 143.50; 143.61; 145.32 (quaternary C), ν$_{max}$/cm$^{-1}$ 3069 (aromatic C—H); 2930 and 2854 (aliphatic C—H); 1558 (aromatic C=C). UV/Vis (CH$_2$Cl$_2$): λ$_{max}$ (ε L·mol$^{-1}$·cm$^{-1}$)=304 nm (20400); 282 nm (22500); 230 nm (19300). Elementary analysis for C$_{28}$H$_{37}$IN$_2$; Calculated: C, 63.63; H, 7.06; N, 5.30%. Found: C, 63.64; H, 7.09; N, 5.14%.

3-dodecyl-1-(9H-fluoren-2-yl)-2H-imidazol-3-ium bis(trifluoromethylsulfonyl)amide (63)

The general procedure with 53 (0.330 g; 0.69 mmol) and lithium bis(trifluoromethylsulfonyl)amide (0.492 g; 1.71 mmol) allowed 63 to be obtained with a yield of 89% (0.419 g; 0.61 mmol). $^1$H NMR (300 MHz, CDCl$_3$): δ=0.88 (t, 3H, J=6.33 Hz, CH$_3$ aliphatic chain); 1.27-1.38 (broad m, 18H, CH$_2$ aliphatic chain and N—CH$_2$—CH$_2$—CH$_2$); 1.98 (qui, 2H, J=7.95 Hz, N—CH$_2$—CH$_2$); 4.04 (s, 2H, CH$_2$ fluorene); 4.37 (t, 2H, J=7.68 Hz, N—CH$_2$); 7.39-7.48 (m, 3H, CH fluorene or imidazolium); 7.53-7.62 (m, 3H, CH fluorene or imidazolium); 7.83 and 7.86 (dd, 2H, J=1.65 and 9.87 Hz, CH fluorene or imidazolium); 7.94 (d, 1H, J=8.22 Hz, CH fluorene or imidazolium); 9.26 (s, 1H, N—CH—N). $^{13}$C NMR (75 MHz, CDCl$_3$): δ=14.03 (C—CH$_3$ aliphatic chain); 22.62; 26.13; 28.85; 29.27; 29.42; 29.54; 30.05; 31.85 (CH$_2$ aliphatic chain); 36.88 (CH$_2$ fluorene); 50.66 (N—CH$_2$); 119.87 (qua, J=319.65 Hz, (CF$_3$SO$_2$)$_2$N$^-$); 118.90; 120.57; 120.72; 121.21; 121.80; 123.07; 125.24; 127.18; 128.07 (CH fluorene or imidazolium); 132.50 (quaternary C); 133.81 (CH fluorene or imidazolium); 139.56; 143.69; 144.06; 145.67 (quaternary C). ν$_{max}$/cm$^{-1}$ 3139 (aromatic C—H); 2922 and 2855 (aliphatic C—H); 1464 (aromatic C=C); 1349 and 1121 ((CF$_3$SO$_2$)$_2$N$^-$). UV/Vis (CH$_2$Cl$_2$): λ$_{max}$ (ε L·mol$^{-1}$·cm$^{-1}$)=304 nm (19900); 281 nm (21800); 227 nm (13200). Elementary analysis for C$_{30}$H$_{37}$F$_6$N$_3$O$_4$S$_2$; Calculated: C, 52.85; H, 5.47; N, 6.16%. Found: C, 53.01; H, 5.50; N, 6.37%.

3-dodecyl-1-(9-methylcarbazol-3-yl)-2H-imidazol-3-ium Tetrafluoroborate (64)

The general procedure with 54 (0.189 g; 0.38 mmol) and potassium tetrafluoroborate (0.218 g; 1.73 mmol) allowed 64 to be obtained with a yield of 65% (0.125 g; 0.25 mmol). $^1$H NMR (300 MHz, CDCl$_3$): δ=0.88 (t, 3H, J=6.30 Hz, CH$_3$ aliphatic chain); 1.26-1.36 (broad m, 18H, CH$_2$ aliphatic chain and N—CH$_2$—CH$_2$—CH$_2$); 1.95 (qui, 2H, J=7.14 Hz, N—CH$_2$—CH$_2$); 3.82 (s, 3H, CH$_3$ carbazole); 4.37 (t, 2H, J=7.14 Hz, N—CH$_2$); 7.30-7.32 (m, 1H, CH carbazole or imidazolium); 7.39-7.48 (m, 3H, CH carbazole or imidazolium); 7.54-7.65 (m, 3H, CH carbazole or imidazolium); 8.17 (d, 1H, J=7.68 Hz, CH carbazole or imidazolium); 8.27 (broad s, 1H, CH carbazole or imidazolium); 9.32 (s, 1H, N—CH—N). $^{13}$C NMR (75 MHz, CDCl$_3$): δ=14.04 (C—CH$_3$ aliphatic chain); 22.62; 26.24 (CH$_2$ aliphatic chain); 28.91 (CH$_3$ carbazole); 28.96; 29.28; 29.37; 29.49; 29.56; 29.57; 30.10; 31.85 (CH$_2$ aliphatic chain); 50.29 (N—CH$_2$); 108.82; 109.42; 113.41; 118.54; 119.65; 120.90; 121.60 (CH carbazole or imidazolium); 121.73 (quaternary C); 122.59 (CH carbazole or imidazolium); 122.99; 125.99 (quaternary C); 126.94; 133.78 (CH carbazole or imidazolium); 140.49; 141.52 (quaternary C). ν$_{max}$/cm$^{-1}$ 3164 (aromatic C—H); 2919 and 2852 (aliphatic CH); 1589 (aromatic C=C); 1056 (BF$_4^-$). UV/Vis (CH$_2$Cl$_2$): λ$_{max}$ (ε L·mol$^{-1}$·cm$^{-1}$)=351 nm (2500); 334 nm (3500); 279 nm (29600); 239 nm (29700). Elementary analysis for C$_{28}$H$_{38}$BF$_4$N$_3$; Calculated: C, 66.80; H, 7.61; N, 8.35%. Found: C, 66.65; H, 7.78; N, 8.39%.

3-dodecyl-1-(9-methylcarbazol-3-yl)-2H-imidazol-3-ium Hexafluorophosphate (65)

The general procedure with 54 (0.185 g; 0.37 mmol) and potassium hexafluorophosphate (0.288 g; 1.56 mmol) allowed 65 to be obtained with a yield of 2% (0.150 g; 0.27 mmol). $^1$H NMR (300 MHz, CDCl$_3$): δ=0.88 (t, 3H, J=6.33 Hz, CH$_3$ aliphatic chain); 1.26-1.35 (broad m, 18H, CH$_2$ aliphatic chain and N—CH$_2$—CH$_2$—CH$_2$); 1.94 (qui, 2H, J=6.87 Hz, N—CH$_2$—CH$_2$); 3.80 (s, 3H, CH$_3$ carbazole); 4.31 (t, 2H, J=6.87 Hz, N—CH$_2$); 7.39-7.34 (m, 1H, CH carbazole or imidazolium); 7.39-7.45 (m, 3H, CH carbazole or imidazolium); 7.53-7.58 (m, 3H, CH carbazole or imidazolium); 8.14 (d, 1H, J=7.95 Hz, CH carbazole or imidazolium); 8.21 (broad s, 1H, CH carbazole or imidazolium); 8.95 (s, 1H, N—CH—N). $^{13}$C NMR (75 MHz, CDCl$_3$): δ=14.06 (C—CH$_3$ aliphatic chain); 22.65; 26.23; 28.93 (CH$_2$ aliphatic chain); 28.99 (CH$_3$ carbazole); 29.30; 29.35; 29.49; 29.59; 30.04 (CH$_2$ aliphatic chain); 50.44

(N—CH$_2$); 108.94; 109.60; 113.58; 118.81; 119.81; 120.81 (CH carbazole or imidazolium); 121.73 (quaternary C); 121.84; 122.54 (CH carbazole or imidazolium); 123.13; 125.97 (quaternary C); 127.10; 133.86 (CH carbazole or imidazolium); 140.71; 141.65 (quaternary C). $v_{max}$/cm$^{-1}$ 3053 (aromatic C—H); 2922 and 2853 (aliphatic C—H); 1560 (aromatic C=C); 816 (PF$_6^-$). UV/Vis (CH$_2$Cl$_2$): $\lambda_{max}$ ($\varepsilon$ L·mol$^{-1}$.cm$^{-1}$)=350 nm (2200); 334 nm (3200); 280 nm (28600); 238 nm (29300). Elementary analysis for C$_{28}$H$_{38}$F$_6$N$_3$P; Calculated: C, 59.88; H, 6.82; N, 7.48%. Found: C, 59.83; H, 6.96; N, 7.45%.

3-dodecyl-1-(9-methylcarbazol-3-yl)-2H-imidazol-3-ium Iodide (66)

The general procedure with 54 (0.415 g; 0.84 mmol) and potassium iodide (0.416 g; 2.50 mmol) allowed 66 to be obtained with a yield of 56% (0.256 g; 0.47 mmol). $^1$H NMR (300 MHz, CDCl$_3$): $\delta$=0.88 (t, 3H, J=6.30 Hz, CH$_3$ aliphatic chain); 1.26-1.45 (broad m, 18H, CH$_2$ aliphatic chain and N—CH$_2$—CH$_2$—CH$_2$); 2.03 (qui, 2H, J=7.41 Hz, N—CH$_2$—CH$_2$); 3.87 (s, 3H, CH$_3$ carbazole); 4.56 (t, 2H, J=7.41 Hz, N—CH$_2$); 7.30-7.34 (m, 1H, CH carbazole or imidazolium); 7.41-7.62 (m, 4H, CH carbazole or imidazolium); 7.67 (t, 1H, J=1.92 Hz, CH carbazole or imidazolium); 7.81 and 7.84 (dd, 1H, J=2.19 and 8.52 Hz, CH carbazole or imidazolium); 8.20 (d, 1H, J=7.68 Hz, CH carbazole or imidazolium); 8.43 (d, 1H, J=2.19 Hz, CH carbazole or imidazolium); 10.77 (s, 1H, N—CH—N). $^{13}$C NMR (75 MHz, CDCl$_3$): $\delta$=13.98 (C—CH$_3$ aliphatic chain); 22.55; 26.19; 28.95; 29.20; 29.30 (CH$_2$ aliphatic chain); 29.35 (CH$_3$ carbazole); 29.42; 29.48; 29.49; 30.26; 31.78 (CH$_2$ aliphatic chain); 50.36 (N—CH); 108.85; 109.45; 113.90; 118.73; 119.64; 121.31; 121.40 (CH carbazole or imidazolium); 121.77 (quaternary C); 122.54 (CH carbazole or imidazolium); 123.00; 125.90 (quaternary C); 126.96; 134.49 (CH carbazole or imidazolium); 140.45; 141.51 (quaternary C). $v_{max}$/cm$^{-1}$ 3040 (aromatic C—H); 2919 and 2851 (aliphatic C—H); 1559 (aromatic C=C). UV/Vis (CH$_2$Cl$_2$): $\lambda_{max}$ ($\varepsilon$ L·mol$^{-1}$.cm$^{-1}$)=352 nm (3700); 336 nm (4500); 281 nm (32200); 239 nm (42900). Elementary analysis for C$_{28}$H$_{38}$IN$_3$; Calculated: C, 61.87; H, 7.05; N, 7.73%. Found: C, 61.93; H, 7.12; N, 7.66%.

3-dodecyl-1-(9-methylcarbazol-3-yl)-2H-imidazol-3-ium bis(trifluoromethylsulfonyl)amide (67)

The general procedure with 54 (0.367 g; 0.74 mmol) and lithium bis(trifluoromethylsulfonyl)amide (0.652 g; 2.27 mmol) allowed 67 to be obtained with a yield of 90% (0.466 g; 0.67 mmol). $^1$H NMR (300 MHz, CDCl$_3$): $\delta$=0.88 (t, 3H, J=6.84 Hz, CH$_3$ aliphatic chain); 1.27-1.38 (broad m, 18H, CH$_2$ aliphatic chain and N—CH$_2$—CH$_2$—CH$_2$); 1.98 (qui, 2H, J=7.68 Hz, N—CH$_2$—CH$_2$); 3.91 (s, 3H, CH$_3$ carbazole); 4.38 (t, 2H, J=7.68 Hz, N—CH$_2$); 7.31-7.36 (m, 1H, CH carbazole or imidazolium); 7.44-7.49 (m, 2H, CH carbazole or imidazolium); 7.53-7.66 (m, 4H, CH carbazole or imidazolium); 8.15 (d, 1H, J=7.68 Hz, CH carbazole or imidazolium); 8.25 (s, 1H, CH carbazole or imidazolium); 9.16 (s, 1H, N—CH—N). $^{13}$C NMR (75 MHz, CDCl$_3$): $\delta$=14.02 (C—CH$_3$ aliphatic chain); 22.61; 26.15; 28.86 (CH$_2$ aliphatic chain); 29.10 (CH$_3$ carbazole); 29.27; 29.29; 29.43; 29.54; 30.07; 31.84 (CH$_2$ aliphatic chain); 50.47 (N—CH$_2$); 109.02; 109.66; 113.79; 118.98; 119.84 (CH carbazole or imidazolium); 119.92 (qua, J=319.65 Hz, (CF$_3$SO$_2$)$_2$N$^-$); 120.84 (CH carbazole or imidazolium); 121.76 (quaternary C); 122.16; 122.74 (CH carbazole or imidazolium); 123.25; 125.95 (quaternary C); 127.16; 133.51 (CH carbazole or imidazolium); 140.84; 141.73 (quaternary C). $v_{max}$/cm$^{-1}$ 3055 (aromatic C—H); 2930 and 2857 (aliphatic C—H); 1423 (aromatic C=C); 1350 and 1197 ((CF$_3$SO$_2$)$_2$N$^-$). UV/Vis (CH$_2$Cl$_2$): $\lambda_{max}$ ($\varepsilon$ L·mol$^{-1}$.cm$^{-1}$)=351 nm (3000); 337 nm (4000); 281 nm (28100); 238 nm (28900). Elementary analysis for C$_{30}$H$_{38}$F$_6$N$_4$O$_4$S$_2$; Calculated: C, 51.71; H, 5.50; N, 8.04%. Found: C, 51.97; H, 5.60; N, 8.21%.

1-(anthracen-9-yl)-3-dodecyl-2H-imidazol-3-ium Tetrafluoroborate (68)

The general procedure with 55 (0.165 g; 0.33 mmol) and potassium tetrafluoroborate (0.253 g; 2.01 mmol) allowed 68 to be obtained with a yield of 88% (0.147 g; 0.29 mmol). $^1$H NMR (300 MHz, CDCl$_3$): $\delta$=0.89 (t, 3H, J=6.84 Hz, CH$_3$ aliphatic chain); 1.27-1.43 (broad m, 18H, CH$_2$ aliphatic chain and N—CH$_2$—CH$_2$—CH$_2$); 2.08 (qui, 2H, J=7.68 Hz, N—CH$_2$—CH$_2$); 4.62 (t, 2H, J=7.41 Hz, N—CH$_2$); 7.37 (d, 2H, J=8.79 Hz, CH anthracene or imidazolium); 7.49 (t, 1H, J=1.65 Hz, CH anthracene or imidazolium); 7.57-7.68 (m, 4H, CH anthracene or imidazolium); 7.83 (t, 1H, J=1.65 Hz, CH anthracene or imidazolium); 8.15 (d, 2H, J=7.68 Hz, CH anthracene or imidazolium); 8.75 (s, 1H, CH anthracene or imidazolium); 9.02 (s, 1H, N—CH—N). $^{13}$C NMR (75 MHz, CDCl$_3$): $\delta$=14.04 (C—CH$_3$ aliphatic chain); 22.61; 26.15; 28.93; 29.27; 29.40; 29.45; 29.55; 29.57; 30.07; 31.83 (CH$_2$ aliphatic chain); 50.66 (N—CH$_2$); 120.30; 123.74 (CH anthracene or imidazolium); 124.49 (quaternary C); 125.49; 126.22 (CH anthracene or imidazolium); 127.50 (quaternary C); 128.70; 129.23 (CH anthracene or imidazolium); 130.75 (quaternary C); 131.07; 137.63 (CH anthracene or imidazolium). $v_{max}$/cm$^{-1}$ 3061 (aromatic C—H); 2921 and 2852 (aliphatic C—H); 1545 (aromatic C=C); 1140 (BF$_4^-$). UV/Vis (CH$_2$Cl$_2$): $\lambda_{max}$ ($\varepsilon$ L·mol$^{-1}$.cm$^{-1}$)=387 nm (5400); 371 nm (6700); 351 nm (5300); 308 nm (8500); 254 nm (185400). Elementary analysis for C$_{29}$H$_{37}$BF$_4$N$_2$; Calculated: C, 69.60; H, 7.45; N, 5.60%. Found: C, 69.53; H, 7.43; N, 5.38%.

1-(anthracen-9-yl)-3-dodecyl-2H-imidazol-3-ium Hexafluorophosphate (69)

The general procedure with 55 (0.165 g; 0.33 mmol) and potassium hexafluorophosphate (0.151 g; 0.82 mmol) allowed 69 to be obtained with a yield of 91% (0.171 g; 0.31 mmol). $^1$H NMR (300 MHz, CDCl$_3$): $\delta$=0.89 (t, 3H, J=6.87 Hz, CH$_3$ aliphatic chain); 1.27-1.42 (broad m, 18H, CH$_2$ aliphatic chain and N—CH$_2$—CH$_2$—CH$_2$); 2.07 (qui, 2H, J=7.41 Hz, N—CH$_2$—CH$_2$); 4.57 (t, 2H, J=7.41 Hz, N—CH$_2$); 7.37 (d, 2H, J=8.76 Hz, CH anthracene or imidazolium); 7.49 (t, 1H, J=1.65 Hz, CH anthracene or imidazolium); 7.57-7.68 (m, 4H, CH anthracene or imidazolium); 7.80 (t, 1H, J=1.65 Hz, CH anthracene or imidazolium); 8.14 (d, 2H, J=8.22 Hz, CH anthracene or imidazolium); 8.69 (s, 1H, N—CH—N); 8.75 (s, 1H, CH anthracene or imidazolium). $^{13}$C NMR (75 MHz, CDCl$_3$): $\delta$=14.07 (C—CH$_3$ aliphatic chain); 22.63; 26.20; 28.91; 29.30; 29.40; 29.46; 29.58; 29.59; 29.85; 31.86 (CH$_2$ aliphatic chain); 50.79 (N—CH$_2$); 120.25; 123.66 (CH anthracene or imidazolium); 124.32 (quaternary C); 125.61; 126.30 (CH anthracene or imidazolium); 127.53 (quaternary C); 128.71; 129.39 (CH anthracene or imidazolium); 130.76 (quaternary C); 131.21; 136.92 (CH anthracene or imidazolium). $v_{max}$/cm$^{-1}$ 3061 (aromatic C—H); 2925 and 2854 (aliphatic C—H); 1549 (aromatic C=C), 845 (PF$_6^-$).

UV/Vis (CH$_2$Cl$_2$): $\lambda_{max}$ ($\epsilon$ L·mol$^{-1}$·cm$^{-1}$)=387 nm (5500); 370 nm (6800); 354 nm (5100); 254 nm (160900). Elementary analysis for C$_{29}$H$_{37}$F$_6$N$_2$P; Calculated: C, 62.36; H, 6.68; N, 5.02%. Found: C, 62.33; H, 6.72; N, 5.01%.

1-(anthracen-9-yl)-3-dodecyl-2H-imidazol-3-ium Iodide (70)

The general procedure with 55 (0.165 g; 0.33 mmol) and potassium iodide (0.225 g; 1.35 mmol) allowed 70 to be obtained with a yield of 91% (0.164 g; 0.30 mmol). $^1$H NMR (300 MHz, CDCl$_3$): δ=0.89 (t, 3H, J=6.87 Hz, CH$_3$ aliphatic chain); 1.28-1.53 (broad m, 18H, CH$_2$ aliphatic chain and N—CH$_2$—CH$_2$—CH$_2$); 2.14 (qui, 2H, J=7.68 Hz, N—CH$_2$—CH$_2$); 4.92 (t, 2H, J=7.41 Hz, N—CH$_2$); 7.42 (d, 2H, J=8.76 Hz, CH anthracene or imidazolium); 7.50 (t, 1H, J=1.65 Hz, CH anthracene or imidazolium); 7.59-7.69 (m, 4H, CH anthracene or imidazolium); 7.95 (t, 1H, J=1.65 Hz, CH anthracene or imidazolium); 8.15-8.18 (m, 2H, CH anthracene or imidazolium); 8.77 (s, 1H, CH anthracene or imidazolium); 10.05 (s, 1H, N—CH—N). $^{13}$C NMR (75 MHz, CDCl$_3$): δ=13.94 (C—CH$_3$ aliphatic chain); 22.50; 26.05; 28.92; 29.16; 29.30; 29.35; 29.43; 29.46; 30.31; 31.73 (CH$_2$ aliphatic chain); 50.89 (N—CH$_2$); 120.43; 124.19 (CH anthracene or imidazolium); 124.31 (quaternary C); 125.21; 126.20 (CH anthracene or imidazolium); 127.41 (quaternary C); 128.70; 129.26 (CH anthracene or imidazolium); 130.73 (quaternary C); 131.07; 137.83 (CH anthracene or imidazolium). $v_{max}$/cm$^{-1}$ 3044 (aromatic C—H); 2920 and 2850 (aliphatic C—H); 1544 (aromatic C=C). UV/Vis (CH$_2$Cl$_2$): $\lambda_{max}$ ($\epsilon$ L·mol$^{-1}$·cm$^{-1}$)=387 nm (6700); 369 nm (8300); 354 nm (6700); 289 nm (3500); 254 nm (165900). Elementary analysis for C$_{29}$H$_{37}$IN$_2$; Calculated: C, 64.44; H, 6.90; N, 5.18%. Found: C, 64.34; H, 6.89; N, 5.20%.

1-(anthracen-9-yl)-3-dodecyl-2H-imidazol-3-ium bis(trifluoromethylsulfonyl)amide (71)

The general procedure with 55 (0.171 g; 0.35 mmol) and lithium bis(trifluoromethylsulfonyl)amide (0.222 g, 0.77 mmol) allowed 71 to be obtained with a yield of 91% (0.219 g; 0.32 mmol). $^1$H NMR (300 MHz, CDCl$_3$): δ=0.89 (t, 3H, J=6.33 Hz, CH$_3$ aliphatic chain); 1.28-1.45 (broad m, 18H, CH$_2$ aliphatic chain and N—CH$_2$—CH$_2$—CH$_2$); 2.10 (qui, 2H, J=7.41 Hz, N—CH$_2$—CH$_2$); 4.58 (t, 2H, J=7.41 Hz, N—CH$_2$); 7.36 (d, 2H, J=8.76 Hz, CH anthracene or imidazolium); 7.54 (t, 1H, J=1.62 Hz, CH anthracene or imidazolium); 7.60-7.70 (m, 4H, CH anthracene or imidazolium); 7.83 (t, 1H, J=1.65 Hz, CH anthracene or imidazolium); 8.16-8.19 (m, 2H, CH anthracene or imidazolium); 8.78 (s, 1H, CH anthracene or imidazolium); 8.90 (s, 1H, N—CH—N). $^{13}$C NMR (75 MHz, CDCl$_3$): δ=14.04 (C—CH$_3$ aliphatic chain); 22.62; 26.15; 28.85; 29.28; 29.35; 29.41; 29.55; 29.97; 31.86 (CH$_2$ aliphatic chain); 50.92 (N—CH$_2$); 119.67 (qua, J=319.65 Hz, (CF$_3$SO$_2$)$_2$N$^-$); 120.09; 123.70 (CH anthracene or imidazolium); 124.27 (quaternary C); 125.72; 126.37 (CH anthracene or imidazolium); 127.61 (quaternary C); 128.83; 129.47 (CH anthracene or imidazolium); 130.87 (quaternary C); 131.33; 137.39 (CH anthracene or imidazolium). $v_{max}$/cm$^{-1}$ 3055 (aromatic C—H); 1423 (aromatic C=C); 1350 and 1138 (N(SO$_2$CF$_3$)$_2$$^-$). UV/Vis (CH$_2$Cl$_2$): $\lambda_{max}$ ($\epsilon$ L·mol$^{-1}$·cm$^{-1}$)= 387 nm (4900); 370 nm (6000); 354 nm (4900); 254 nm (156800). Elementary analysis for C$_{31}$H$_{37}$F$_6$N$_3$O$_4$S$_2$; Calculated: C, 53.67; H, 5.38; N, 6.06%. Found: C, 53.88; H, 5.48; N, 6.09%.

1-(9H-fluoren-2-yl)-3-Hexyl-1H-imidazol-3-ium Bromide (72)

A round-bottom flask was charged with 1-(9H-fluoren-2-yl)-1H-imidazole (2.054 g, 8.843 mmol) and 1-bromohexane (8 mL). The reaction mixture was heated to 156° C. for 48 hours. The product was recovered by precipitation in ether followed by drying under reduced pressure at ambient temperature for 24 hours. A white, slightly coloured powder was obtained (2 g, 57%).

Melting point (Mp): Mp=206.4±1° C.

NMR experiments were conducted in CDCl$_3$. CH NMR: 6 mg/0.3 mL CDCl$_3$):

$^1$H NMR (300 MHz, CDCl$_3$, 20° C.): δ 11.10 ppm (s, 1H, =aromatic CH—), 8.01 (s, 1H, =aromatic CH—), 7.87 (d, 1H, =aromatic CH—, $^3$J=8.07 Hz), 7.76 (m, 3H, =aromatic CH—), 7.55 (m, 2H, =aromatic CH—), 7.39 (m, 2H, =aromatic CH—), 4.59 (t, 2H, N—CH$_2$—CH$_2$—(CH$_2$)$_3$—CH$_3$, $^3$J=7.35 Hz), 3.97 (s, 2H, N—CH$_2$—), 1.99 (m, 2H, N—CH$_2$—CH$_2$—(CH$_2$)$_3$—CH$_3$), 1.35 (m, 6H, N—CH$_2$—CH$_2$—(CH$_2$)$_3$—CH$_3$), 0.88 (t, 3H, N—CH$_2$—CH$_2$—(CH$_2$)$_3$—CH$_3$, $^3$J=6.78 Hz).

1-(9H-fluoren-2-yl)-3-Hexyl-1H-imidazol-3-ium Tetrafluoroborate (73)

A round-bottom flask was charged with 1-(9H-fluoren-2-yl)-3-Hexyl-1H-imidazol-3-ium bromide (102 mg, 0.257 mmol) which was dissolved in a water/ethanol mixture (5 mL/4 mL) to which sodium tetrafluoroborate was added (51 mg, 0.465 mmol). The mixture was left under agitation at ambient temperature for 2 days and the reaction mixture then extracted with dichloromethane, dried and evaporated in vacuo at reduced pressure at ambient temperature for 12 hours. A slightly yellowish solid was recovered (93 mg, yield: 90%).

Melting point (Mp): Mp=112.6±1° C.

The product was characterized by NMR spectroscopy.

$^1$H NMR (300 MHz, CDCl$_3$, 20° C.): δ 9.28 ppm (s, 1H, =aromatic CH—), 7.77 (m, 3H, =aromatic CH—), 7.63 (s, 1H), 7.53 (m, 2H, =aromatic CH—), 7.38 (m, 3H, = aromatic CH—), 4.32 (t, 2H, N—CH$_2$—CH$_2$—(CH$_2$)$_3$—CH$_3$, $^3$J=7.35 Hz), 3.91 (s, 2H, N—CH$_2$—), 1.91 (m, 2H, N—CH$_2$—CH$_2$—(CH$_2$)$_3$—CH$_3$), 1.31 (m, 6H, N—CH$_2$—CH$_2$—(CH$_2$)$_3$—CH$_3$), 0.87 (t, 3H, N—CH$_2$—CH$_2$—(CH$_2$)$_3$—CH$_3$, $^3$J=6.8 Hz). $^{13}$C {$^1$H} NMR (75 MHz, CDCl3, 20° C.): δ 13.84 (N—(CH2)5—CH3) ppm, 22.31 (N—(CH2)4-CH2—CH3), 25.82 (N—(CH2)3-CH2-CH2-CH3), 30.02 (N—(CH2)2-CH2-(CH2)2-CH3), 30.98 (N—CH2-CH2-(CH2)3-CH3), 36.88 (—CH2-Fluorene), 50.46 (N—CH2-CH2-(CH2)3-CH3), 118.66 (aromatic C), 120.48 (aromatic C), 121.07 (aromatic C), 121.36 (aromatic C), 123.00 (aromatic C), 125.13 (aromatic C), 127.09 (aromatic C), 127.90 (aromatic C), 132.60 (aromatic C), 134.08 (aromatic C), 139.52 (aromatic C), 143.59 (aromatic C), 145.47 (aromatic C).

The invention claimed is:

1. An imidazolium compound of formula (Id):

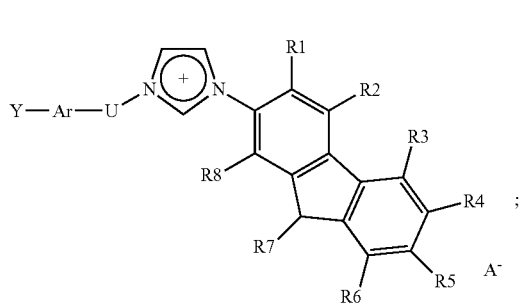

Ar and U are absent;
wherein:

represents the imidazolium cation,
Y is a group comprising at least one $sp^3$ carbon atom and represents
an alkyl or O-alky group, alkyl being defined as a saturated hydrocarbon radical optionally comprising one or more unsaturations, straight-chain or branched, having 1 to 30 carbon atoms, optionally substituted;
R1, R2, R3, R4, R5, R6, R7, and R8 are each independently:
H;
F, Cl, Br, I; or
$C_1$-$C_{30}$ alkyl group, $C_3$-$C_7$ cycloalkyls, $C_6$-$C_{10}$ aryl, heteroaryl, aralkyl, heteroarylalkyl, wherein the said alkyl or aryl groups are optionally substituted;
and wherein said compound is associated with an A counter-ion represented by $B(R^4)_4$— wherein $R^4$ on each occurrence is a group independently selected from the group consisting of a halogen atom, $C_1$-$C_6$ alkyl group, $C_6$-$C_{10}$ aryl group, and an aralkyl group.

2. The compound according to claim 1, wherein «Y» is selected from the group consisting of the following radicals: methyl, ethyl, propyl, butyl, pentyl, hexyl, octyl, nonyl, decyl, dodecyl, hexadecyl, and octadecyl.

3. The compound according to claim 1, wherein imidazolium compound of formula (Id) is 3-dodecyl-1-(9H-fluoren-2-yl)-2H-imidazol-3-ium tetrafluoroborate or 1-(9H-fluoren-2-yl)-3-octyl-2H-imidazol-3-ium tetrafluoroborate:

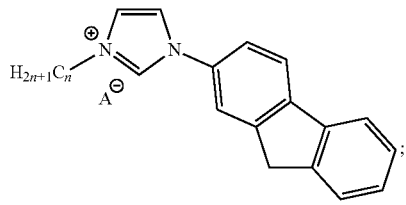

and
wherein n is 8 or 12 and $A^-$ is tetrafluoroborate.

4. The compound according to claim 1, wherein Y is a $C_nH_{2n+1}$ or O—$C_nH_{2n+1}$ alkyl group where n is a number ranging from 5 to 20.

5. The compound according to claim 1, wherein Y is selected from the group consisting of the following radicals: methyl, ethyl, propyl, butyl, pentyl, hexyl, octyl, nonyl, decyl, dodecyl, tetradecyl, pentadecyl, hexadecyl, heptadecyl, octadecyl, isopropyl, tert-butyl, 2-ethylhexyl, 2-methylbutyl, 2-methylpentyl, 1-methylpentyl and 3-methylheptyl.

6. The compound according to claim 1 wherein $A^-$ is $BF_4^-$.

7. A fluorophore solid or liquid material comprising or consisting of a fluorophore compound according to claim 1.

8. The fluorophore solid or liquid material according to claim 7, wherein the material is a transparent plastic material.

9. A method for the detection of gamma, X, neutron, or proton radiation, said method comprising detecting gamma, X, neutron, or proton radiation using at least one fluorophore compound of formula (Id) according to claim 1.

10. The method according to claim 9 for discrimination between proton/gamma, proton/X, neutron/gamma, neutron/X, alpha/gamma, alpha/X radiation.

11. A method for discrimination between proton/gamma, proton/X, neutron/gamma, neutron/X, alpha/gamma, alpha/X radiation, said method comprising discrimination between proton/gamma, proton/X, neutron/gamma, neutron/X, alpha/gamma, alpha/X radiation using at least one fluorophore compound, wherein said fluorophore compound is an imidazolium compound of formula (Id) according to claim 1.

12. An instrument for radiation detection, industrial or medical dosimetry comprising a fluorophore compound comprising an imidazolium group directly attached to an aromatic group via a covalent bond between a nitrogen atom of the imidazolium group and a $sp^2$ carbon atom of the said aromatic group, wherein said fluorophore compound is an imidazolium compound of formula (Id) according to claim 1.

13. A method to prepare a compound according to claim 1 comprising a coupling reaction of an aromatic group with an imidazole group by creating a covalent bond between a $sp^2$ carbon atom of the aromatic group and a nitrogen atom of the imidazole group in the presence of a zeolite NaY containing copper(II) and a base, wherein said fluorophore compound is an imidazolium compound according to claim 1.

14. A method to prepare a compound of formula (Id) according to claim 1, wherein said method comprises:
(i) coupling an R aromatic group and an imidazole group via a coupling reaction between said R aromatic group and said imidazole group by creating a covalent bond between a $sp^2$ carbon atom of the aromatic group and a nitrogen atom of the imidazole group, in the presence of a zeolite NaY containing copper(II) and a base; and
(ii) coupling a Y group and an imidazole group via a coupling reaction of said Y group comprising at least one $sp^3$ carbon atom with a said imidazole group by creating a covalent bond between the $sp^3$ carbon atom of said Y group and a nitrogen atom of said imidazole group, wherein R and Y are as defined in claim 1.

15. The method according to claim 14 wherein step (i) corresponds to the following reaction:

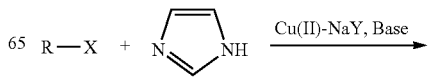

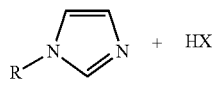 + HX

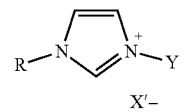

where X is a halogen atom.

16. The method according to claim 14 wherein step (ii) corresponds to the following reaction:

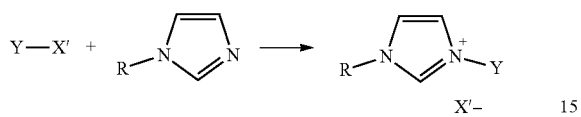

where X'— is a halogen atom and «-» is the negative charge of this atom.

17. The method according to claim 14 wherein the compound:

is caused to react with a salt of the desired A⁻ anion to obtain the compound:

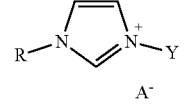

by anion metathesis.

18. The method according to claim 9, wherein said method is for the detection of slow neutrons wherein slow neutrons are neutrons whose kinetic energy is below 1 keV.

* * * * *